US012729393B2

(12) United States Patent
Kavalopoulos et al.

(10) Patent No.: US 12,729,393 B2
(45) Date of Patent: Sep. 8, 2026

(54) AGENT INTERACTION EFFECTS DETERMINATION

(71) Applicants: Nikolaos Kavalopoulos, Uppsala (SE); Roderich Römhild, Vienna (AT); Po-Cheng Tang, Uppsala (SE); Johan Kreuger, Uppsala (SE); Dan Andersson, Uppsala (SE)

(72) Inventors: Nikolaos Kavalopoulos, Uppsala (SE); Roderich Römhild, Vienna (AT); Po-Cheng Tang, Uppsala (SE); Johan Kreuger, Uppsala (SE); Dan Andersson, Uppsala (SE)

( * ) Notice: Subject to any disclaimer, the term of this patent is extended or adjusted under 35 U.S.C. 154(b) by 707 days.

(21) Appl. No.: 17/905,345

(22) PCT Filed: Mar. 19, 2021

(86) PCT No.: PCT/SE2021/050243
§ 371 (c)(1),
(2) Date: Aug. 31, 2022

(87) PCT Pub. No.: WO2021/188037
PCT Pub. Date: Sep. 23, 2021

(65) Prior Publication Data

US 2023/0111986 A1 Apr. 13, 2023

(30) Foreign Application Priority Data

Mar. 20, 2020 (SE) .................................... 2050304-1

(51) Int. Cl.
*C12Q 1/20* (2006.01)
*C12M 1/32* (2006.01)

(52) U.S. Cl.
CPC ............... *C12Q 1/20* (2013.01); *C12M 23/12* (2013.01)

(58) Field of Classification Search
None
See application file for complete search history.

(56) References Cited

U.S. PATENT DOCUMENTS 3,985,608 A 10/1976 Saxholm
4,324,859 A 4/1982 Saxholm
(Continued)

FOREIGN PATENT DOCUMENTS

CN 102740907 A 10/2012
EP 0181075 A1 5/1986
(Continued)

OTHER PUBLICATIONS

Examination Report dated Jun. 17, 2025 from corresponding Indian Application No. 2022 27056786, 8 pages.
(Continued)

*Primary Examiner* — Erin M. Bowers
(74) *Attorney, Agent, or Firm* — Porter Wright Morris & Arthur LLP

(57) ABSTRACT

A cell population (55) is cultured on a cell culture substrate (50) while agents contained in agent reservoirs (31, 33, 35) at predefined positions in a culture container (10) diffuse through the substrate (50) and form at least partly overlapping concentration gradients in the substrate (50) within combination areas (41, 43, 45) and substantially non-overlapping concentration gradients in the substrate (50) peripheral to an outer boundary of the agent reservoirs (31, 33, 35). Inhibition end points (61, 63, 65) of respective inhibition zones (60, 62, 64) substantially lacking any growth of the cell population (55) peripheral to the outer boundary of the agent reservoirs (31, 33, 35) and growth end points (71, 73, 75) of respective growth zones (70, 72, 74) comprising growth of the cell population (55) within the combination areas (41, 43, 45) are determined and used to determine
(Continued)

interaction effects between the agents on the cell population (55).

12 Claims, 29 Drawing Sheets

(56) References Cited

U.S. PATENT DOCUMENTS

| | | | |
|---|---|---|---|
| 5,028,529 | A | 7/1991 | Ericcson et al. |
| 5,639,632 | A | 6/1997 | Ericsson et al. |
| 6,153,400 | A | 11/2000 | Matsumura et al. |
| 6,251,624 | B1 | 6/2001 | Matsumura et al. |
| 7,106,889 | B1 | 9/2006 | Mahers et al. |
| 2009/0068696 | A1 | 3/2009 | Frimodt-Moller |
| 2017/0298408 | A1 | 10/2017 | Rolain et al. |
| 2018/0208958 | A1 | 7/2018 | Drazek et al. |
| 2023/0270941 | A1 | 8/2023 | Day et al. |

FOREIGN PATENT DOCUMENTS

| | | | | |
|---|---|---|---|---|
| EP | 1416042 | A1 | | 5/2004 |
| GB | 2035371 | A | | 6/1980 |
| KR | 10-2002-0034171 | A | | 5/2002 |
| WO | 87/00858 | A1 | | 2/1987 |
| WO | 99/02645 | A1 | | 1/1999 |
| WO | 00/55357 | A1 | | 9/2000 |
| WO | WO 00/55357 | | * | 9/2000 |
| WO | 01/09371 | A1 | | 2/2001 |
| WO | 2004/050675 | A1 | | 6/2004 |
| WO | 2009/026920 | A1 | | 3/2009 |
| WO | 2011/032683 | A1 | | 3/2011 |
| WO | 2015/028983 | A1 | | 3/2015 |
| WO | WO 2015/028983 | | * | 8/2015 |
| WO | 2016/210292 | A1 | | 12/2016 |
| WO | 2019/063690 | A1 | | 4/2019 |

OTHER PUBLICATIONS

Fatsis-Kavalopulos, Nikos Lumitos, Antibiotic interaction testing made easy New high-speed test shows how antibiotics combine to kill bacteria, https://www.Bionity.com/en/news/pdf/1168009.pdf, pp. 1-2 (Sep. 21, 2020).

Fatsis-Kavalopulos, Nikos et al., CombiANT: Antibiotic interaction testing made easy, PLOS Biology, pp. 1-22 (Sep. 17, 2020).

Russ, D et al., Additivity of inhibitory effects in multidrug combinations, Nature Microbiology, vol. 3, No. 12, pp. 1339-1345 (Oct. 15, 2018).

Khan, Zeeshan A. et al., "Current and Emerging Methods of Antibiotic Susceptibility Testing", Diagnostics, vol. 9, No. 2, pp. 1-17 (May 3, 2019).

Office Action dated Feb. 26, 2026 from corresponding Chinese Application No. 2021800219341, pp. 1-8, with English Translation.

Search Report dated Feb. 26, 2026 from corresponding Chinese Application No. 2021800219341, pp. 1-3.

Office Action dated Mar. 13, 2026 from corresponding Indian Application No. 202227056786, pp. 1-4.

Office Action dated Mar. 25, 2026 from corresponding Korean Application No. 10-2022-7036470, with English Translation, pp. 1-14.

* cited by examiner

AGENT INTERACTION EFFECTS DETERMINATION

TECHNICAL FIELD

The present invention generally relates to determining agent interaction effects of a mixture of agents on a cell population.

BACKGROUND

Wherever two or more bioactive compounds co-occur there may be compound interaction effects. Compounds interact when the combined effect of a compound mixture is higher (positive synergy) or lower (negative synergy, antagonism) than expected from independent action (additivity) of the compounds alone. Several compounds with positive synergy may, thus, be physically combined to maximize a certain biological activity. Conversely, other compounds with negative synergy may be desired to act physically separately to avoid an inhibition of activities that occurs in mixtures.

Combination effects and synergy optimization are particularly important in the fields of biomedicine. Combination treatments of two or more drugs are increasingly used for the treatment of cancer, and infectious diseases, for instance bacterial, viral or fungal infectious diseases. Combination treatments are favorable compared to single drug treatments, as they increase treatment efficiency and reduce resistance evolution. The efficacy of combination treatments is related to the physiological interaction of drugs, which can produce the preferred positive synergistic but also antagonistic effects.

With the spread of antibiotic resistance, synergistic combinations of antibiotics are increasingly used as a first-line therapeutic option. Antibiotic combination therapy enables efficient treatment of complicated bacterial infections, including those with resistant and heteroresistant bacteria, and they have been shown to decrease mortality and accelerate patient recovery. However, recent data indicates that drug interaction can vary between species and clinical isolates [1], making careful diagnostics vital for treatment success.

Synergy quantification requires the measurement of individual and combined effects of several compounds. A difficulty is that synergy can typically be quantified best in a narrow concentration window, the steep region of the sigmoidal dose-response curve, which may be shifted by several orders of magnitude depending on the biological sample. A quantitative measure of antibiotic synergy is the so-called fractional inhibitory concentration index (FICi). The FICi for two antibiotics A and B is defined as $c_A/MIC_A+c_B/MIC_B$, where $MIC_{A/B}$ is the minimal inhibitory concentration of pure A or B and $c_{A/B}$ denotes the concentration of antibiotic A or B in a MIC-producing mixture of A+B. The minimum inhibitory concentration (MIC) is the smallest concentration of a compound that prevents growth of the sample.

The standard methodology for synergy quantification is a two-dimensional broth microdilution where several discrete concentrations of two compounds are combined in a full-factorial grid—the checkerboard—of usually 9×9 or 8×12 concentrations. Once the concentration grid is generated, a cell sample is added and the biological response is measured during, or after, a set incubation time. Simplified checkerboard assays have been developed for synergy quantification between three or more drugs [2].

Alternative solutions for synergy quantification have been developed for Petri dish cultures on semisolid agar surfaces. Antimicrobial susceptibility testing (AST) is routinely performed using paper disks impregnated with antibiotics or other compounds. These disks are placed onto agar surfaces that are seeded with a cell sample. Diffusion of the compounds from the disks into the surrounding agar generates a concentration gradient and the cell sample can grow only up to the MIC, leaving characteristic inhibition zones. When several disks with distinct drugs are placed in proximity, synergy can distort the shape of the inhibition zones. Thus, arrangements of AST disks have been used for qualitative synergy detection [3]. A similar method uses paper or plastic strips that are coated with a compound concentration gradient that diffuses into the agar in a defined way [4, 5]. An enlargement of the inhibition zone indicates positive synergy; a narrowing indicates antagonistic effects. Generally, these methods only provide qualitative information and not any quantitative information of synergy, such as FICi values.

Synergy can be quantified using strip cross formation, where two strips are placed in 90° angle and the test strips cross each other at the MIC points [6]. A disadvantage of antibiotic test strip cross-formation is that it requires multiple steps. As the test strips need to cross each other on the MIC points, the MICs of the cell sample need to be known from a previous assay. A third solution is the use of closed agar diffusion compartments [7], where seeded agar surfaces are partitioned into smaller areas in which diffusion establishes a homogenous concentration. The diffusion compartments enable a checkerboard-like testing of discrete concentrations and compound mixtures in agar plates.

There is, thus, still a need for a fast and simple method for synergy quantification and optimization that can be used for clinical diagnostics, and is applicable to a wide range of bioactive compounds.

SUMMARY

It is a general objective of the invention to determine agent interaction effects of a mixture of agents on a cell population.

This and other objectives are met by embodiments as disclosed herein.

The present invention is defined in the independent claims. Further embodiments of the invention are defined in the dependent claims.

An aspect of the invention relates to a method for determining agent interaction effects on a cell population. The method comprises adding a cell culture substrate into a culture container comprising N agent reservoirs at predefined positions relative to each other. Each agent reservoir of the N agent reservoirs comprises an agent, the N agent reservoirs enclose combination areas and N is an integer equal to or larger than three. The method also comprises placing a cell population on and/or in the cell culture substrate and culturing the cell population on and/or in the cell culture substrate for a predefined period of time while the agents in the N agent reservoirs diffuse through the cell culture substrate and form at least partly overlapping agent concentration gradients in the cell culture substrate within the combination areas and substantially non-overlapping agent concentration gradients in the cell culture substrate peripheral to an outer boundary of the N agent reservoirs. The method further comprises determining, for each agent reservoir of at least two adjacent agent reservoirs of the N agent reservoirs, an inhibition end point of an inhibition zone substantially lacking any growth of the cell population.

The inhibition end point is positioned peripherally to the outer boundary of the agent reservoir. The method additionally comprises determining, for the at least two adjacent agent reservoirs, a growth end point of a growth zone comprising growth of the cell population within a combination area with at least partly overlapping agent concentration gradients of the agents contained or comprised in the at least two adjacent agent reservoirs. The method also comprises determining an agent interaction effect between the agents contained in the at least two adjacent agent reservoirs based on the inhibition end points and the growth end point.

Another aspect of the invention relates to a culture container insert comprising a circular bottom plate with a central N-gonal opening and a circular wall attached to a circumference of the circular bottom plate. The culture container insert also comprises N chord walls attached to the circular wall and the circular bottom plate and enclosing the central N-gonal opening. The circular bottom plate, the circular wall and each chord wall define an agent reservoir and N is an integer equal to or larger than three.

A related aspect of the invention defines a culture container comprising a bottom disc, a circumferential wall attached to the bottom disc and a culture container insert according to above positioned in the culture container with the circular bottom plate placed on the bottom disc and the circular wall distanced from the circumferential wall.

A further aspect of the invention relates to a culture container comprising a bottom disc, a circumferential wall attached to the bottom disc and a circular wall attached to the bottom disc and enclosed by and distanced from the circumferential wall. The culture container also comprises N chord walls attached to the circular wall and the bottom disc and enclosing an N-gon part of the bottom disc. The bottom disc, the circular wall and each chord wall define an agent reservoir and N is an integer equal to or larger than three.

Yet another aspect of the invention relates to a kit for determining agent interaction effects on a cell population. The kit comprises a culture container according to above and a volume of cell culture substrate gel configured to be added into the culture container and allowed to solidify into a cell culture substrate. Each agent reservoir of the N agent reservoirs comprises a respective agent and the N agent reservoirs enclose combination areas. The kit also comprises instructions to take at least one picture of the cell culture substrate following a predefined period of time from placing a cell population on and/or in the cell culture substrate. The agents in the N agent reservoirs diffuse through the cell culture substrate and form at least partly overlapping agent concentration gradients in the cell culture substrate within the combination areas and substantially non-overlapping agent concentration gradients in the cell culture substrate peripheral to an outer boundary on the N agent reservoirs. The kit further comprises instructions to determine, from the at least one picture and for each agent reservoir of the N agent reservoirs, an inhibition end point of an inhibition zone substantially lacking any growth of the cell population. The inhibition end point is positioned peripherally to the agent reservoir. The kit also comprises instructions to determine, from the at least one picture and for each combination of two adjacent agent reservoirs of the N agent reservoirs, a growth end point of a growth zone comprising growth of the cell population within a combination area with at least partly overlapping agent concentration gradients of the agents contained in the at least two adjacent agent reservoirs. The kit further comprises information defining diffusion coefficients for the agents contained in the N agent reservoirs with regard to the cell culture substrate. The kit also comprises instructions to determine, for each combination of two adjacent agent reservoirs, an agent interaction effect between the agents contained in the two adjacent agent reservoirs based on the inhibition end points determined for the two adjacent agent reservoirs, the growth end point determined for the two adjacent agent reservoirs and the information defining diffusion coefficients.

A further aspect of the invention relates to a computer program comprising instructions, which when executed by at least one processor, cause the at least one processor to provide image data representing at least one picture taken of a cell culture substrate in culture container at a predefined period of time following placing a cell population on and/or in the cell culture substrate. The culture container comprises N agent reservoirs at predefined positions relative to each other. Each agent reservoir of the N agent reservoirs comprises an agent. The N agent reservoirs enclose combination areas and N is an integer equal to or larger than three. The agents in the N agent reservoirs diffuse through the cell culture substrate and form at least partly overlapping agent concentration gradients in the cell culture substrate within the combination areas and substantially non-overlapping agent concentration gradients in the cell culture substrate peripheral to an outer boundary on the N agent reservoirs. The at least one processor is also caused to determine, based on the image data and for each agent reservoir of at least two adjacent agent reservoirs of the N agent reservoirs, an inhibition end point of an inhibition zone substantially lacking any growth of the cell population. The inhibition end point is positioned peripherally to the outer boundary of the agent reservoir. The at least one processor is further caused to determine, based on the image data and for the at least two adjacent agent reservoirs, a growth end point of a growth zone comprising growth of the cell population within a combination area with at least partly overlapping agent concentration gradients of the agents contained in the at least two adjacent agent reservoirs. The at least one processor is additionally caused to determine an agent interaction effect between the agents contained in the at least two adjacent agent reservoirs based on the inhibition end points and the growth end point.

A related aspect of the invention defines a computer-readable storage medium comprising a computer program according to above.

The present invention enables quantification, in a single experiment and in a single culture container, of interaction effects, such as synergy or antagonistic effects, for combinations of agents. The invention not only provides qualitative information of any such agent interaction but also enables a quantification of the agent interactions.

BRIEF DESCRIPTION OF THE DRAWINGS

The embodiments, together with further objects and advantages thereof, may best be understood by making reference to the following description taken together with the accompanying drawings, in which.

DETAILED DESCRIPTION

The present invention generally relates to determining agent interaction effects of a mixture of agents on a cell population.

The present invention can be used to investigate and determine interaction effects for combinations of agents on a cell population. The invention can be used to verify that a combination of agents has an interaction effect on the cell population and also to quantify the magnitude of the interaction effect, i.e., provides both qualitative and quantitative information. This means that the invention can be used to assess whether a combination of agents exerts a synergistic effect, an inhibitory or antagonistic effect or indeed merely have independent or additive effect on the cell population and also used to quantify such a synergistic or inhibitory/antagonistic effect.

"Agent" as used herein relates to any molecule, compound, composition or other agent that may exert an effect on a cell population and where interaction effects of such an agent with another agent with regard to the cell population are to be determined. Typical, but non-limiting, examples of such agents include drugs or medicaments, including drug candidates, and where the interaction of a combination of different drugs or medicaments on a cell population is of interest. For instance, it may be of interest to see whether a combination of different drugs or medicaments may exert an effect on the cell population that is beyond a mere additive effect, i.e., whether the combination of the drugs or medicaments have a higher or larger effect than expected from independent actions of the drugs or medicaments alone, i.e., a synergistic effect. Furthermore, it may be of interest to see whether one of the drugs or medicaments in such a combination inhibits the actions or effects that the other drug or medicament alone exerts on the cell population, i.e., determine whether there is any antagonistic effect.

There are several diseases where a combination or cocktail of drugs or medicaments are used for treatment, including cytostatic or chemotherapeutic agents in chemotherapy of cancer patients, antibiotics or antimicrobial agents in bacterial infections, and also combinations of antiviral or antifungal agents in such virus or fungal infections.

The agents do not necessarily have to be drugs or medicaments but may, for instance, be toxic substances, pollutants, ions or other chemicals, where there may be an interest to determine whether the agents have any interactive effects on a cell population.

Figure 12:
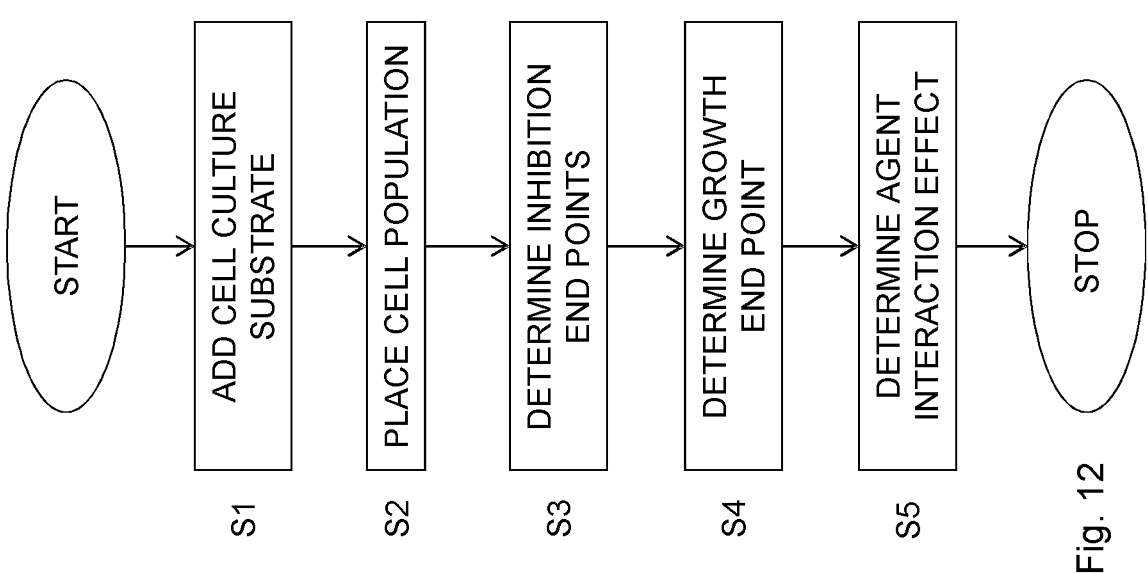
FIG. 12 is a flow chart illustrating a method for determining agent interaction effects on a cell population according to an embodiment.

FIG. 12 is a flow chart illustrating a method of determining agent interaction effects on a cell population according to an embodiment. This method is described below with reference to FIGS. 1, 2, 9 and 10. The method starts in step S1, which comprises adding a cell culture substrate 50 into a culture container 10 comprising N agent reservoirs 31, 33, 35 at predefined positions relative to each other. Each agent reservoir 31, 33, 35 of the N agent reservoirs 31, 33, 35 comprises an agent and the N agent reservoir 31, 33, 35 enclose combination areas 41, 43, 45 as shown in FIG. 10. According to this embodiment, the parameter N is an integer equal to or larger than three.

The method also comprises placing, in step S2, a cell population 55 on and/or in the cell culture substrate 50 and culturing the cell population 55 on and/or in the cell culture substrate 50 for a predefined period of time while the agents in the N agent reservoirs 31, 33, 35 diffuse through the cell culture substrate 50 and form at least partly overlapping agent concentration gradients in the cell culture substrate 50 within the combination areas 41, 43, 45 and substantially non-overlapping agent concentration gradients in the cell culture substrate 50 peripheral to an outer boundary of the N agent reservoirs 31, 33, 35.

The method further comprises determining, in step S3 and for each agent reservoir 31, 33, 35 of at least two adjacent agent reservoirs 31, 33, 35 of the N agent reservoirs 31, 33, 35, an inhibition end point 61, 63, 65 of an inhibition zone 60, 62, 64 substantially lacking any growth of the cell population 55. This inhibition end point 61, 63, 65 is positioned peripherally relative to the outer boundary of the agent reservoir 31, 33, 35.

The method also comprises determining, in step S4 and for the at least two adjacent agent reservoirs 31, 33, 35, a growth end point 71, 73, 75 of a growth zone 70, 72, 74 comprising growth of the cell population 55 within a combination area 41, 43, 45 with at least partly overlapping agent concentration gradients of the agents contained in the at least two adjacent agent reservoirs 31, 33, 35.

Steps S3 and S4 of FIG. 12 can be performed at least partly in parallel or serially in any order, i.e., step S3 prior to step S4 or step S4 prior to step S3.

The method further comprises determining, in step S5, an agent interaction effect between the agents contained in the at least two adjacent agent reservoirs 31, 33, 35 based on the inhibition end points 61, 63, 65 and the growth end point 71, 73, 75.

The culture container 10 used in the method shown in FIG. 12 could be any container or device used for culturing cells including, but not limited to, a culture plate, a culture dish, such as a Petri dish.

In an embodiment, step S1 in FIG. 12 comprises adding a cell culture substrate gel into the culture container 10 and allowing the cell culture substrate gel to solidify into the cell culture substrate 50. Hence, in this embodiment, a cell culture substrate gel is poured into the culture container 10 and allowed to solidify into a cell culture substrate 50, on and/or in which the cell population 55 can be cultured.

The cell culture substrate gel and the cell culture substrate 50 could be any such substrate gel and substrate used for culturing cells in vitro. Non-limiting, but illustrative examples, of such cell culture substrates 50 include agar, agarose, alginate, bacterial cellulose, MATRIGEL®, hydrogel, poly-L-lysine and fibronectin.

An alternative to adding a cell culture substrate gel in step S1 could be to add, cast or pour a cell culture substrate 50, such as porous cell culture substrate 50, into the culture container 10 and optionally allow the (porous) cell culture substrate 50 to solidify in the culture container 10. In fact, any cell culture substrate 10 that can be cast, polymerized or in any other way formed in the culture container 10 could be used according to the invention.

The cell population 55 is placed on and/or in the cell culture substrate in step S2. In a preferred embodiment, the cell population 55 is placed on a surface 51 of the cell culture substrate 50 and cultured on the surface 51 of the cell culture substrate 50 for the predefined period of time. The cell population 55 will then form a two-dimensional (2D) culture on the surface 51 of the cell culture substrate 50. In another embodiment, the cell population 55 may be placed at least partly in the cell culture substrate 50. This means that the cells may grow as a three-dimensional (3D) culture inside the cell culture substrate 50 and optionally at least partly on the surface 51 of the cell culture substrate 50. In this embodiment, the cell population 55 may be pre-mixed with a cell culture substrate gel so that steps S1 and S2 are performed at least partly in parallel. Alternatively, the cell population 55 may be added to the cell culture substrate gel prior to solidification into the cell culture substrate 50.

Figure 2:
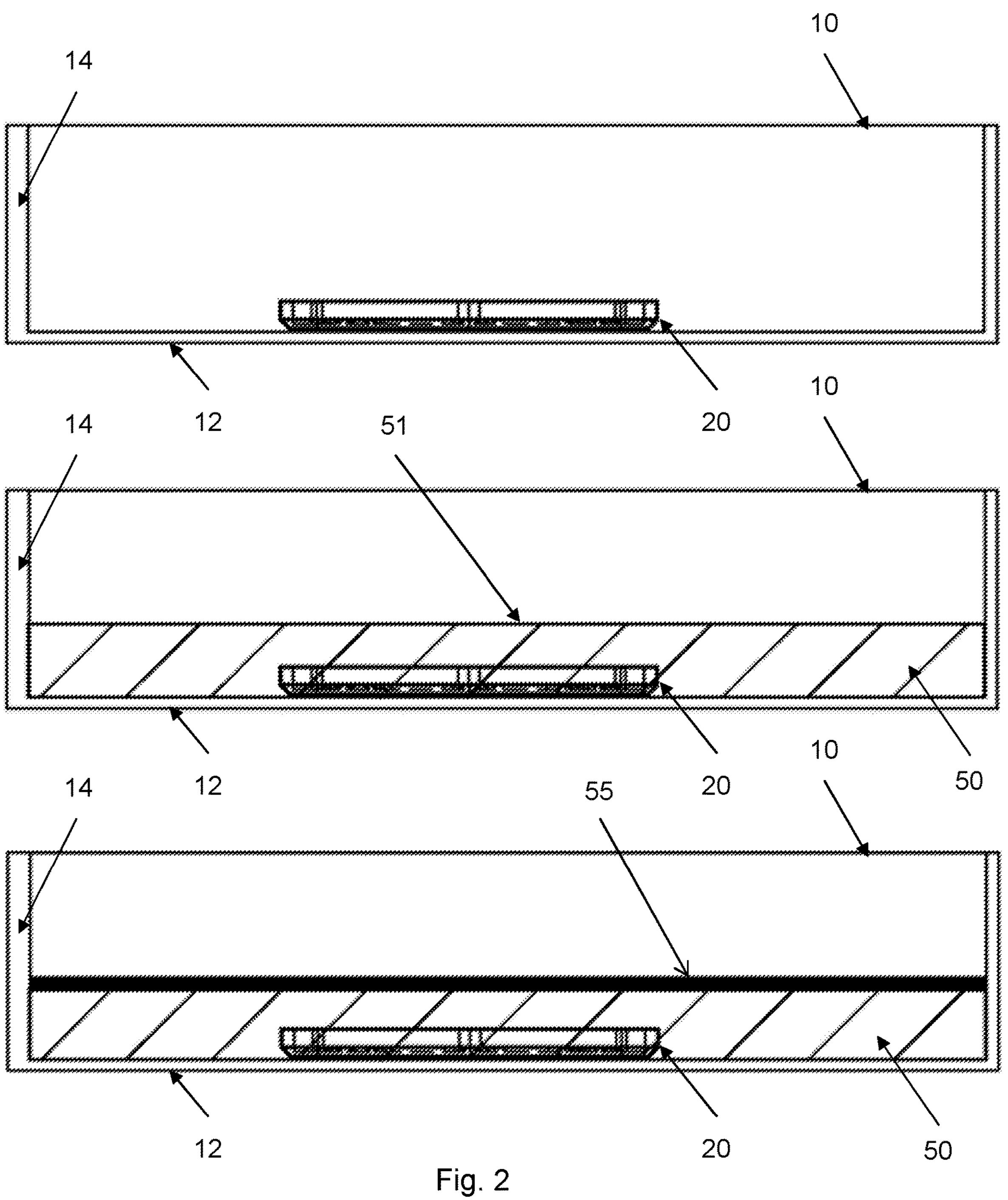
FIG. 2 schematically illustrates a culture container comprising a culture container insert (top), following addition of a cell culture substrate (middle) and plating of a cell culture (bottom).

The culture container 10 comprises N agent reservoirs 31, 33, 35 comprising a respective agent. The agent reservoirs 31, 33, 35 are arranged at predefined positions relative to each other and enclose a central area or window 40 comprising the so-called combination areas 41, 43, 45. These agent reservoirs 31, 33, 35 could be any reservoir, chamber or cell configured to comprise the agents. The agent reservoirs 31, 33, 35 are open reservoirs and not closed reservoirs, i.e., do not have any lock or ceiling. This means that the agent reservoirs 31, 33, 35 are open to the cell culture substrate 50 as shown in FIG. 2 to enable the agents contained in the agent reservoirs 31, 33, 35 to diffuse through the cell culture substrate 50 and thereby forming concentration gradients in the cell culture substrate 50 with ever decreasing concentrations of the agents the further away from the agent reservoirs 31, 33, 35 in the cell culture substrate 50.

The diffusion of the agents from the agent reservoirs 31, 33, 35 and the positions of the agent reservoirs 31, 33, 35 relative to each other means that the portion of the cell culture substrate 50 peripherally relative to an outer boundary of an agent reservoir 31, 33, 35, i.e., the portion of the cell culture substrate 50 positioned between the outer boundary or restriction of the agent reservoir 31, 33, 35 and the periphery of the cell culture substrate 50, substantially only comprises agent diffused from that agent reservoir 31, 33, 35. For instance, when traveling along the line 80 indicated in FIG. 9 from the outer boundary of the agent reservoir 31 towards the periphery of the cell culture substrate 50 there is concentration gradient of the agent contained in the agent reservoir 31 with a high concentration at the outer boundary of the agent reservoir 31 and a low concentration, or even zero concentration, of the agent at the periphery of the cell culture substrate 50. Furthermore, at this part of the cell culture substrate 50 there is substantially no agents diffused from the other agent reservoirs 33, 35. Hence, the concentration of such other agents is substantially zero at this part of the cell culture substrate 50. This means that there are N substantially non-overlapping agent concentration gradients in the cell culture substrate 50 at the respective parts of the cell culture substrate 50 peripherally relative to the agent reservoirs 31, 33, 35.

The agents in the agent reservoirs 31, 33, 35 do not only diffuse peripherally in the cell culture substrate 50 but also towards a center 15 of the central window or part 40 with the combination areas 41, 43, 45. In this central window or part 40 of the cell culture substrate 50 the agents will form at least partly overlapping agent concentration gradients in the combination areas 41, 43, 45. This means that in a given combination area 41 agent concentration gradients of agents contained in a first combination of two adjacent agent reservoirs 31, 33 will at least partly overlap, whereas in another combination area 43 agent concentrations of agents contained in a second combination of two adjacent agent reservoirs 33, 35 will at least partly overlap. This means that each combination area 41, 43, 45 comprises a unique combination of at least partly overlapping agent concentration gradients when each agent reservoir 31, 33, 35 comprises an agent that is different from the agents in the other agent reservoirs, 31, 33, 35.

As a consequence of the arrangement of the agent reservoirs 31, 33, 35, the central window or part 40 of the cell culture substrate 50 will comprise at least partly overlapping agent concentration gradients, whereas the peripheral part of the cell culture substrate 50 beyond the agent reservoirs 31, 33, 35 comprise substantially non-overlapping agent concentration gradients.

The area or part of the cell culture substrate 50 peripheral to the outer boundary of the agent reservoirs 31, 33, 35 comprises a respective inhibition zone 60, 62, 64. In the inhibition zone 60, 62, 64 the concentration of the agent contained in the agent reservoir 31, 33, 35 is sufficiently high to prevent any growth of the cell population 55. The end of this inhibition zone 60, 62, 64 when travelling from the agent reservoir 31, 33, 35 towards the periphery of the cell culture substrate 50, i.e., the so-called inhibition end point 61, 63, 65, represents the lowest concentration of the agent contained in the agent reservoir 31, 33, 35 that can prevent or inhibit growth of the cell population 55.

The respective combination areas 41, 43, 45 in the central window or part 40 of the cell culture substrate 50 comprise a respective growth zone 70, 72, 74 comprising growth of the cell population 55. Each such growth zone 70, 72, 74 comprises an end point within the combination area 41, 43, 45 where the cell population is no longer growing. This end point between cell growth and lack of cell growth constitutes the so-called growth end point 71, 73, 75. At this point the combination of concentrations of two agents contained in adjacent agent reservoirs 31, 33, 35 is sufficient to prevent or inhibit growth of the cell population 55.

The agent interaction effect between two agents can then be determined based on the inhibition end points 61, 63, 65 determined for the two agents/agent reservoirs 31, 33, 35 and based on the growth end point 71, 73, 75 determined for combination area 41, 43, 45, in which the agent concentration gradients of the two agents partly overlap.

Figure 13:
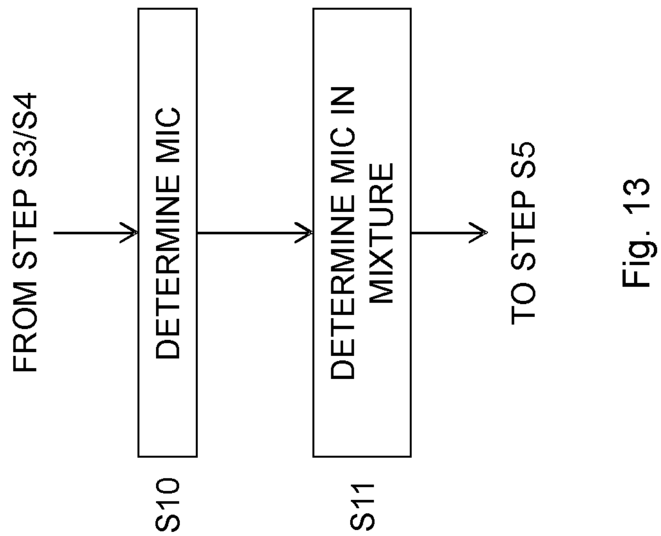
FIG. 13 is a flow chart illustrating additional, optional steps of the method shown in FIG. 12 according to an embodiment.

In an embodiment, the method comprises two additional steps as shown in FIG. 13. Step S10 is performed following step S3 in FIG. 12 and comprises determining, for each agent reservoir 31, 33, 35 of the at least two adjacent agent reservoirs 31, 33, 35, a minimum inhibitory concentration (MIC) of the agent contained in the agent reservoir 31, 33, 35 with regard to the cell population based on the inhibition end point 61, 63, 65. Step S11 in FIG. 13 is performed following step S4 in FIG. 12 and comprises determining, for each agent reservoir 31, 33, 35 of the at least two adjacent agent reservoirs 31, 33, 35, a MIC of the agent in the agent reservoir 31, 33, 35 in a mixture of the agents contained in the at least two adjacent agent reservoirs 31, 33, 35 based on the growth end points 71, 73, 75.

The method then continues to step S5 in FIG. 12. In this embodiment, step S5 comprises determining a fractional inhibitory concentration index (FICi) based on the MICs.

In a particular embodiment, step S5 comprises determining the FICi based on, or preferably equal to, $c_A/MIC_A+c_B/MIC_B$. $MIC_A$ represents the MIC determined in step S10 for agent A contained in an agent reservoir 31, whereas $MIC_B$ represents the MIC determined in step S10 for agent B contained in an adjacent agent reservoir 33. These MIC values are, thus, determined based on the respective inhibition end points 61, 63. Correspondingly, $c_A$ represents the MIC of the agent A in a MIC-producing mixture of agents A and B as determined in step S11 based on the growth end point 71, whereas $c_B$ represents the MIC of the agent B in a MIC-producing mixture of agents A and B as determined in step S11 based on this growth end point 71.

The present invention can, thus, determine the FICi for a combination of two agents in single experiment and cell container 10 since the invention provides not only the MIC of the agents in a mixture but also the individual MICs of the agents, which are also needed in order to determine the FICi for the combination of agents.

Figure 10:
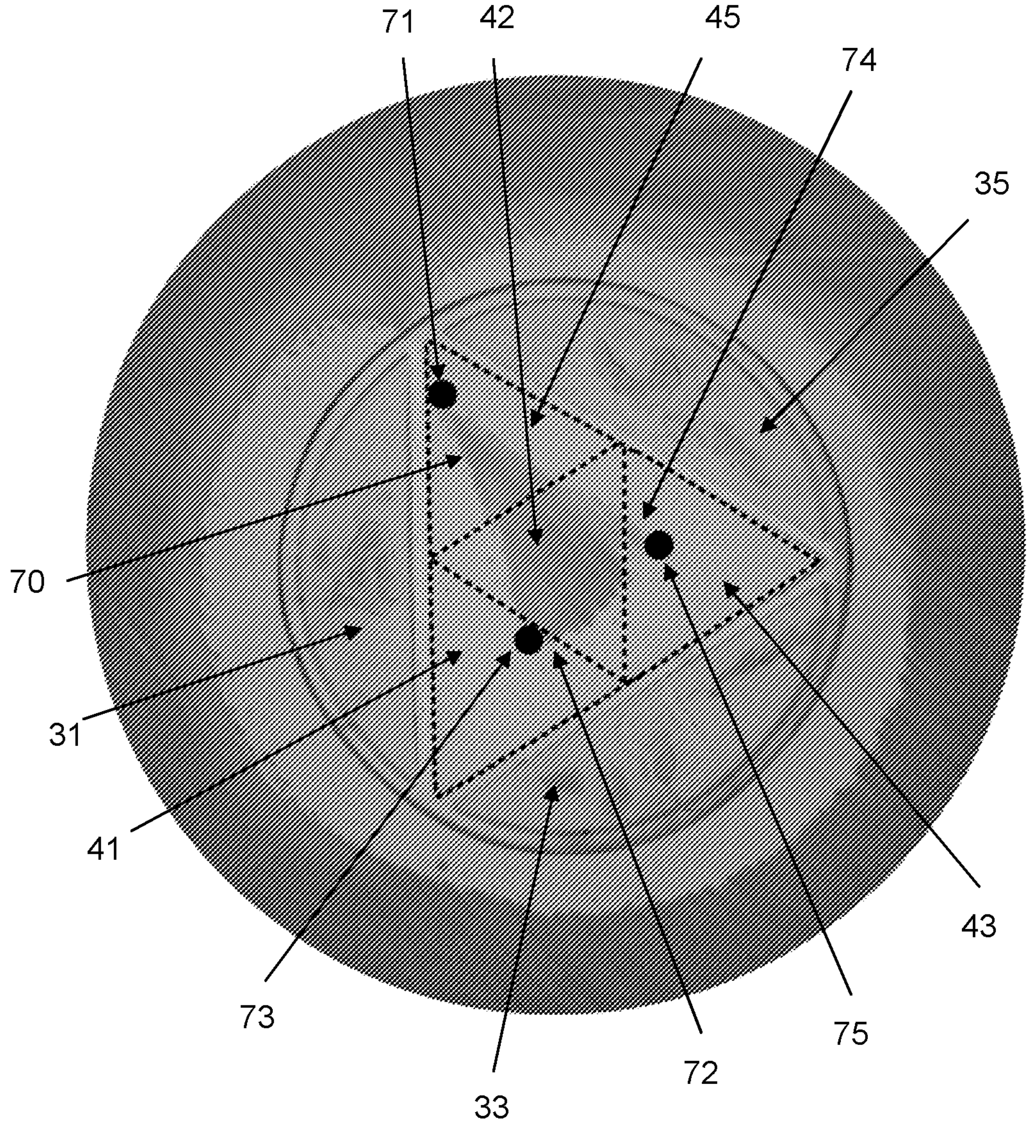
FIG. 10 is a picture taken of a culture container with a culture container insert showing growth zones in the cell culture substrate in combination areas in the central part of the culture container insert.
Figure 11:
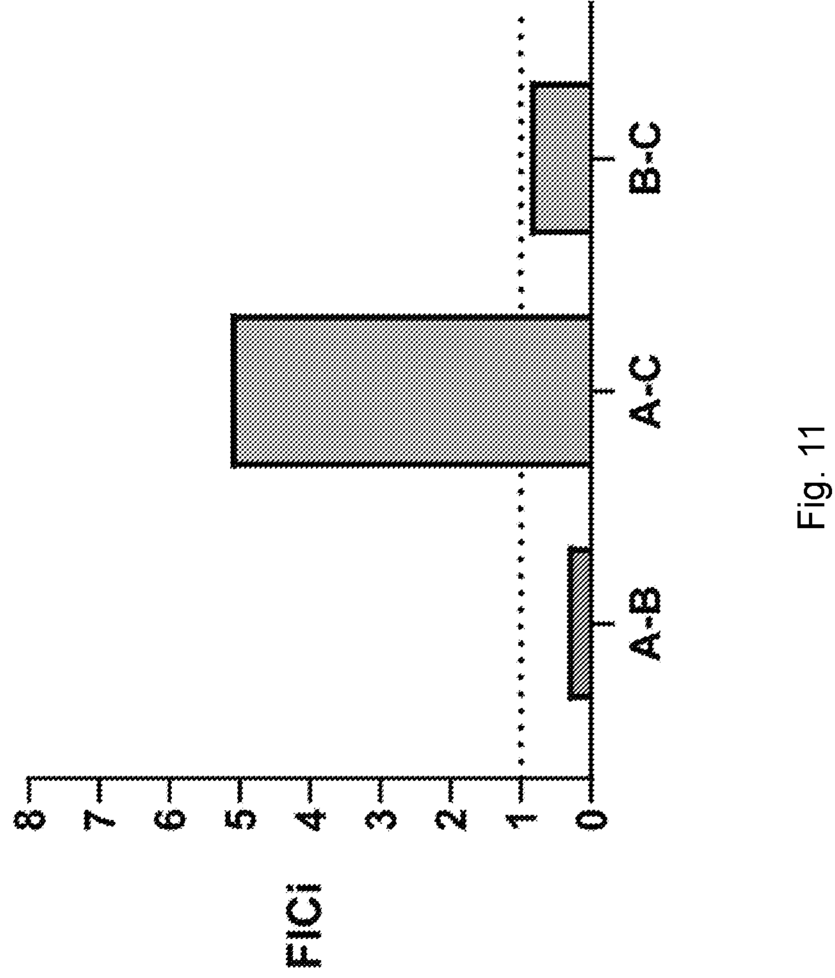
FIG. 11 is a diagram showing fractional inhibitory concentration indices (FICi) for three agents A, B and C determined according to the invention.

FIG. 11 is a diagram showing FICi values for the three agents A, B and C tested in the culture container as shown in FIG. 10. A FICi value smaller than 1 represents a synergistic effect. Such a synergistic effect is seen for the combination of test agents A and B. A FICi value approximately equal to 1 indicates an additive effect, such as shown by the combination of agents B and C. Generally, a FICi value larger than 1 indicates an antagonistic effect. In the present example, the combination of agents A and C achieves an antagonistic effect. Clinically relevant levels of synergy are usually defined as FICi value smaller than 0.5 (as shown here between agents A and B) and clinically relevant levels of antagonism are usually defined as FICi values greater than 4 (as shown here between agents A and C).

In an embodiment, step S10 in FIG. 13 comprises determining, for each agent reservoir 31, 33, 35 of the at least two adjacent agent reservoirs 31, 33, 35, the MIC of the agent contained in the agent reservoir 31, 33, 35 based on a diffusion coefficient of the agent contained in the agent reservoir 31, 33, 35 with regard to the cell culture substrate 50 and the inhibition end point 61, 63, 65. In this embodiment, step S11 comprises determining, for each agent reservoir 31, 33, 35 of the at least two adjacent agent reservoirs 31, 33, 35, the MIC of the agent contained in the agent reservoir 31, 33, 35 in the mixture of the agents contained in the at least two adjacent agent reservoirs 31, 33, 35 based on the diffusion coefficient and the growth end point 71, 73, 75.

The diffusion coefficient of an agent with regard to the cell culture substrate 50 can be used to convert a distance in the cell culture substrate 50 into a concentration of the agent. If the agent concentration gradient of an agent is assumed to follows Fick's laws of diffusion, the concentration (C) of the agent can be calculated by solving the convection-diffusion equation for no advective flux and no net volumetric source using a finite element model (FEM). The model uses the diffusion coefficient (d), time of diffusion (t) and a distance (X) between a defined point in the agent reservoirs 31, 33, 35 and any given point in the cell culture substrate 50, i.e., $C=f(d, t, X)$ for some function f( ) to calculate the agent concentration in that point. The defined point in the agent reservoir 31, 33, 35 used as reference point when measuring the distance to the inhibition end point 61, 63, 65 or the growth end point 71, 73, 75 could be any reference point in or relative to the agent reservoir 31, 33, 35, such as the middle or center of the agent reservoir 31, 33, 35 or a boundary of the agent reservoir 31, 33, 35.

The diffusion coefficient of an agent is typically dependent on the particular cell culture substrate 50 used. This means that a given agent may have a first diffusion coefficient when using a first cell culture substrate and a second, different diffusion coefficient when using a second, different cell culture substrate.

The diffusion coefficient of an agent can be determined for a cell culture substrate in a diffusion calibration. Such a diffusion calibration comprises adding the cell culture substrate 50 into the culture container 10 comprising the N agent reservoirs 31, 33, 35 comprising the agent at respective, different concentrations. For instance, a cell culture substrate gel could be added into the culture container 10 and allowed to solidify into the cell culture substrate 50. The diffusion calibration also comprises placing a test cell population 55 on and/or in the cell culture substrate 50 and culturing the test cell population 55 on and/or in the cell culture substrate 50 for the predefined period of time while the agent in the N agent reservoirs 31, 33, 35 diffuses through the cell culture substrate 50. These steps basically correspond to steps S1 and S2 shown in FIG. 12 but with the difference that each agent reservoir 31, 33, 35 comprises the same agent but preferably in different concentrations. Using different concentrations of the agent in the diffusion calibration means that there will be a readable result even if the particular agent quickly diffuses through the cell culture substrate 50. The test cell population 55 used in the diffusion calibration has a known MIC for the agent.

The diffusion calibration also comprises determining, for at least one agent reservoir 31, 33, 35 of the N agent reservoirs 31, 33, 35, an inhibition end point 61, 63, 65 of an inhibition zone 60, 62, 64 substantially lacking any growth of the test cell population 55. The inhibition end point 61, 63, 65 is positioned peripherally to the outer boundary of the agent reservoir 31, 33, 35. This step basically corresponds to step S3 in FIG. 12.

The diffusion calibration further comprises determining the diffusion coefficient of the agent with regard to the cell culture substrate 50 based on the inhibition end point 61, 63, 65 and the MIC of the agent with regard to the test cell population 55.

Thus, the inhibition end point 61, 63, 65 of the inhibition end zone 60, 62, 63 has a concentration of the agent corresponding to, i.e., substantially equal to, the MIC of the agent with regard to the test cell population 55. The diffusion coefficient (d) can then be calculated using the previously mentioned equation, C=f(d, X), by setting C equal to the known MIC and setting X equal to the distance between the inhibition end point 61, 63, 65 and the defined point in the agent reservoirs 31, 33, 35.

The test cell population 55 used in the diffusion calibration can be any cell population having a known MIC for the agent and that can be cultured on and/or in the cell culture substrate 50.

The diffusion calibration can be performed as a separate process prior to performing the method for determining agent interaction effects. Alternatively, the diffusion calibration could be performed once and then that information is stored for later use when performing the method for determining agent interaction effects. Hence, diffusion coefficients to use in the method can be retrieved from a table or list and may have previously been determined, for instance, using the above mentioned diffusion calibration.

The cell population 55 is cultured on and/or in the cell culture substrate 50 for a predefined period of time. This period of time is selected to enable the cells to grow on and/or in the cell culture substrate 50 and to allow the agents contained in the agent reservoirs 31, 33, 35 to diffuse into the cell culture substrate 50 and form the agent concentration gradients.

The period of time should not be too long since in such a case eventually the agents may then diffuse into the cell culture substrate 50 to form basically uniform concentrations of the agents in the cell culture substrate 50 and thereby no longer any agent concentration gradients. The period of time should furthermore not be too short since then the agent concentration gradients have not had time to be established in the cell culture substrate 50 and the cell population 55 may not have had sufficient time to grow on and/in the cell culture substrate 50.

The predefined period of time is, in an embodiment, selected based on the diffusion coefficients of the agents contained in the agent reservoirs 31, 33, 35 and preferably based on the cell division time of the cell population 55. In a typical embodiment, the predefined period of time is selected within an interval of from 6 hours to 36 hours, preferably within an interval of from 8 hours to 32 hours, and more preferably within an interval of from 10 hours to 30 hours. A currently preferred period of time is from 12 hours to 24 hours. Hence, in a typical embodiment, the cell population 55 is cultured on and/in the cell culture substrate 50 overnight.

Figure 14:
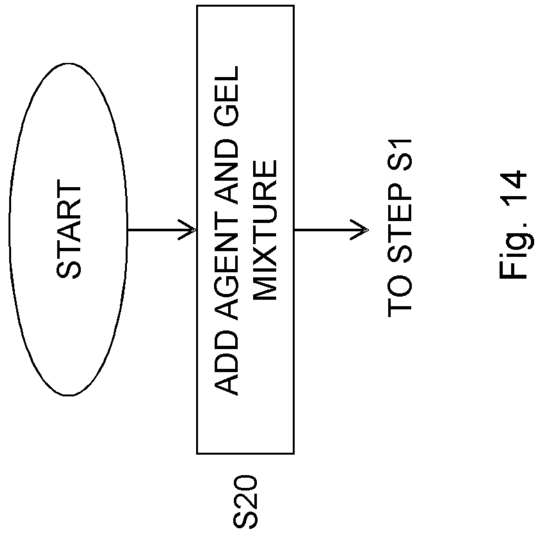
FIG. 14 is a flow chart illustrating an additional, optional step of the method shown in FIG. 12 according to an embodiment.

In an embodiment, the method comprises an additional step S20 as shown in FIG. 14. This step S20 comprises adding, into each agent reservoir 31, 33, 35 of the N agent reservoirs 31, 33, 35, the agent mixed with a gel and allowing the gel to solidify into an agent comprising plug.

In this embodiment, each agent reservoir 31, 33, 35 therefore comprises an agent comprising plug prior to adding the cell culture substrate or the cell culture substrate gel in step S1 in FIG. 12. The gel, with which the agents are mixed, could be the cell culture substrate gel added in step S1 or another gel that can solidify into an agent comprising plug. However, the agent in such an agent comprising plug should be able to diffuse from the agent comprising plug into the cell culture substrate 50 once formed in the culture container 10.

Figure 15:
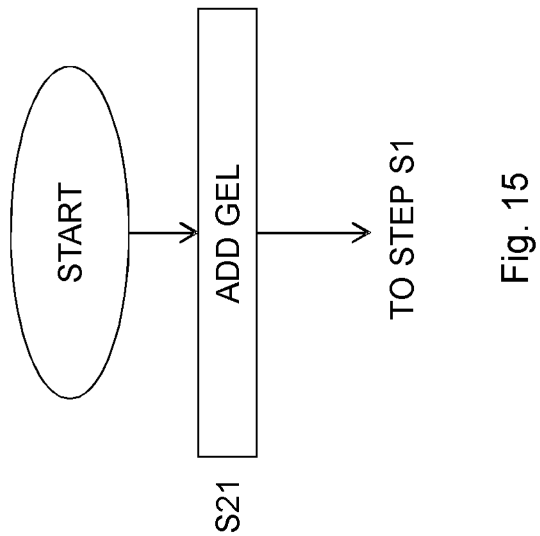
FIG. 15 is a flow chart illustrating an additional, optional step of the method shown in FIG. 12 according to another embodiment.

FIG. 15 illustrates another embodiment of providing agents in the agent reservoirs 31, 33, 35. In this embodiment, each agent reservoir 31, 33, 35 of the N agent reservoirs 31, 33, 35 comprises an agent in lyophilized or dried form. In such a case, a gel is added in step S21 and into each agent reservoir 31, 33, 35 of the N agent reservoirs 31, 33, 35. The agent is then dissolved or dispersed into the gel and the gel is allowed to solidify into an agent comprising plug.

Step S21 could be performed separate from or together with step S1 in FIG. 12. In the former case, the gel is first added to the agent reservoirs 31, 33, 35 and allowed to solidify into the agent comprising plugs. In such a case, the gel could be the cell culture substrate gel added in step S1 or another gel that can solidify into an agent comprising plug. In the latter case, the agent comprising plugs are the parts of the cell culture substrate 50 present in the agent reservoirs 31, 33, 35. It is generally preferred, when using agent reservoirs 31, 33, 35 with lyophilized or dried agents, to first form the agent comprising plugs in the agent reservoirs 31, 33, 35 in step S21 and then adding the cell culture substrate or cell culture substrate gel in step S1 as a separate step to obtain good dissolving or dispersion of the agents in the gel and agent comprising plugs with at least substantially homogenous and defined agent concentrations.

In an embodiment, step S1 of FIG. 12 comprises adding a predefined volume of the cell culture substrate gel into the culture container 10 to cover the N agent reservoirs 31, 33, 35 and allowing the cell culture substrate gel to solidify into the cell culture substrate 50. Hence, sufficient volume of the cell culture substrate gel should be added to the culture container 10 to form a cell culture substrate 50 that covers the agent reservoirs 31, 33, 35.

As an illustrative example, a predefined volume of 25 mL could be used for a standard 90 mm Petri dish. For other culture containers 10, the predefined volume is preferably calculated to cover the culture container insert 20. In a particular example, the culture container insert 20 should be covered by a height of preferably at least 2 mm but preferably not more than 10 mm.

Having a predefined volume of the cell culture substrate gel is in particular advantageous when placing the cell population on the surface 51 of the cell culture substrate 50 and culturing the cell population 55 on the surface 51 of the cell culture substrate 50. In such a case, the agents will diffuse through the cell culture substrate 50 and form at least partly overlapping agent concentrations along the surface 51 of the cell culture substrate 50 within the combination areas 41, 43, 45 and substantially non-overlapping agent concentration gradients along the surface 51 of the cell culture substrate 50 peripheral to the outer boundary of the agent reservoirs 31, 33, 35.

This predefined volume of the cell culture substrate gel is preferably also used in the above mentioned diffusion calibration.

The predefined volume of the cell culture substrate gel is at least partly dependent on the volume of the culture container 10.

In an embodiment, step S3 in FIG. 12 comprises determining, for each agent reservoir 31, 33, 35 of the N agent reservoirs 31, 33, 35, the inhibition end point 61, 63, 65 of the inhibition zone 60, 62, 64. Step S4 comprises, in this embodiment, determining, for each combination of two adjacent agent reservoirs 31, 33, 35 of the N agent reservoirs 31, 33, 35, the growth end point 71, 73, 75 of the growth zone 70, 72, 74 within the combination area 41, 43, 45 with at least partly overlapping agent concentration gradients of the agents contained in the two adjacent agent reservoirs 31, 33, 35. In this embodiment, step S5 comprises determining, for each combination of two adjacent agent reservoirs 31, 33, 35, an agent interaction effect between the agents contained in the two adjacent agent reservoirs 31, 33, 35 based on the inhibition end points 61, 63, 65 determined for the two adjacent agent reservoirs 31, 33, 35 and the growth end point 71, 73, 75 determined for the two adjacent agent reservoirs 31, 33, 35.

Hence, in this embodiment, N inhibition end points 61, 63, 65 and N growth end points 71, 73, 75 are determined and agent interaction effect is determined for each pair of adjacent agent reservoirs 31, 33, 35 and agents contained therein. For instance, a culture container 10 as shown in FIGS. 1, 2, 9 and 10 comprising three agent reservoirs 31, 33, 35 with agents A, B and C could be used to determine the agent interaction effects between agents A and B, between agents A and C and between agents B and C.

Figure 1:
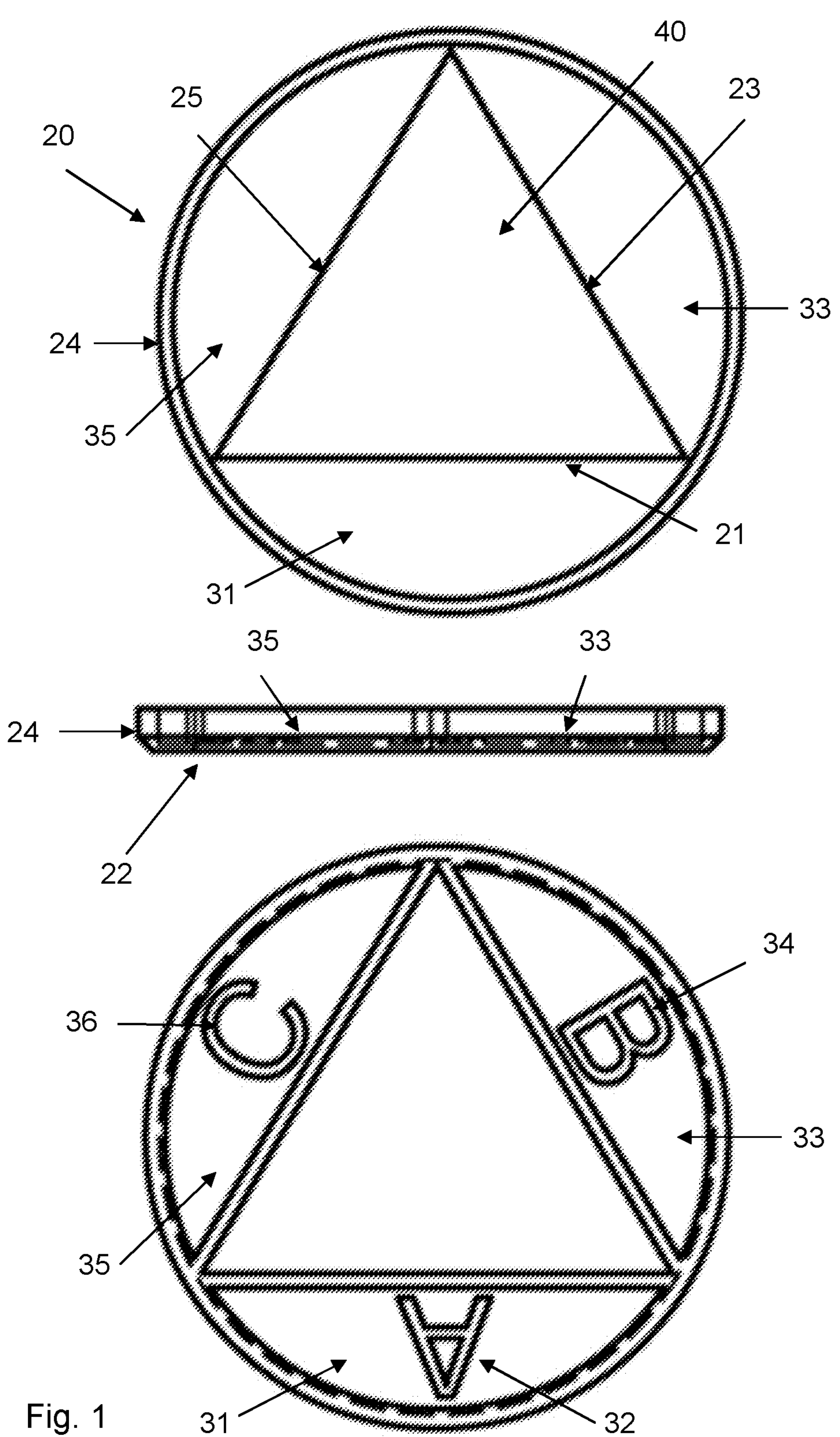
FIG. 1 schematically illustrates a culture container insert according to an embodiment in a bottom view (top), a side view (middle) and top view (bottom).

In an embodiment, the N agent reservoirs 31, 33, 35 are arranged at predefined positions relative to each other along a circumference of a circle as shown in FIG. 1. In such an embodiment, the inhibition end point 61, 63, 65 is positioned along an axis 80 passing through the center 15 of the circle and the agent reservoir 31, 33, 35 and at a position along the axis 80 peripheral to the outer boundary of the agent reservoir 31, 33, 35.

Hence, in such an embodiment, the inhibition end point 61, 63, 65 is positioned radially relative to the center 15 of the circle and along a radius passing through the agent reservoir 31, 33, 35.

Figure 8:
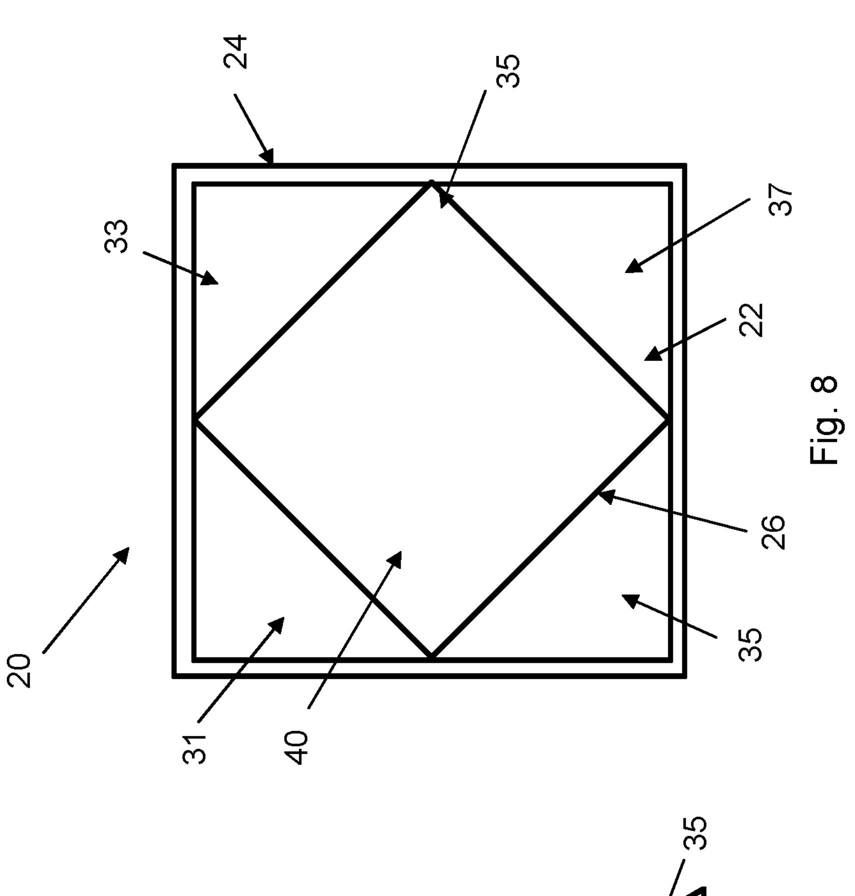
FIG. 8 schematically illustrates a culture container insert according to another embodiment.
Figure 9:
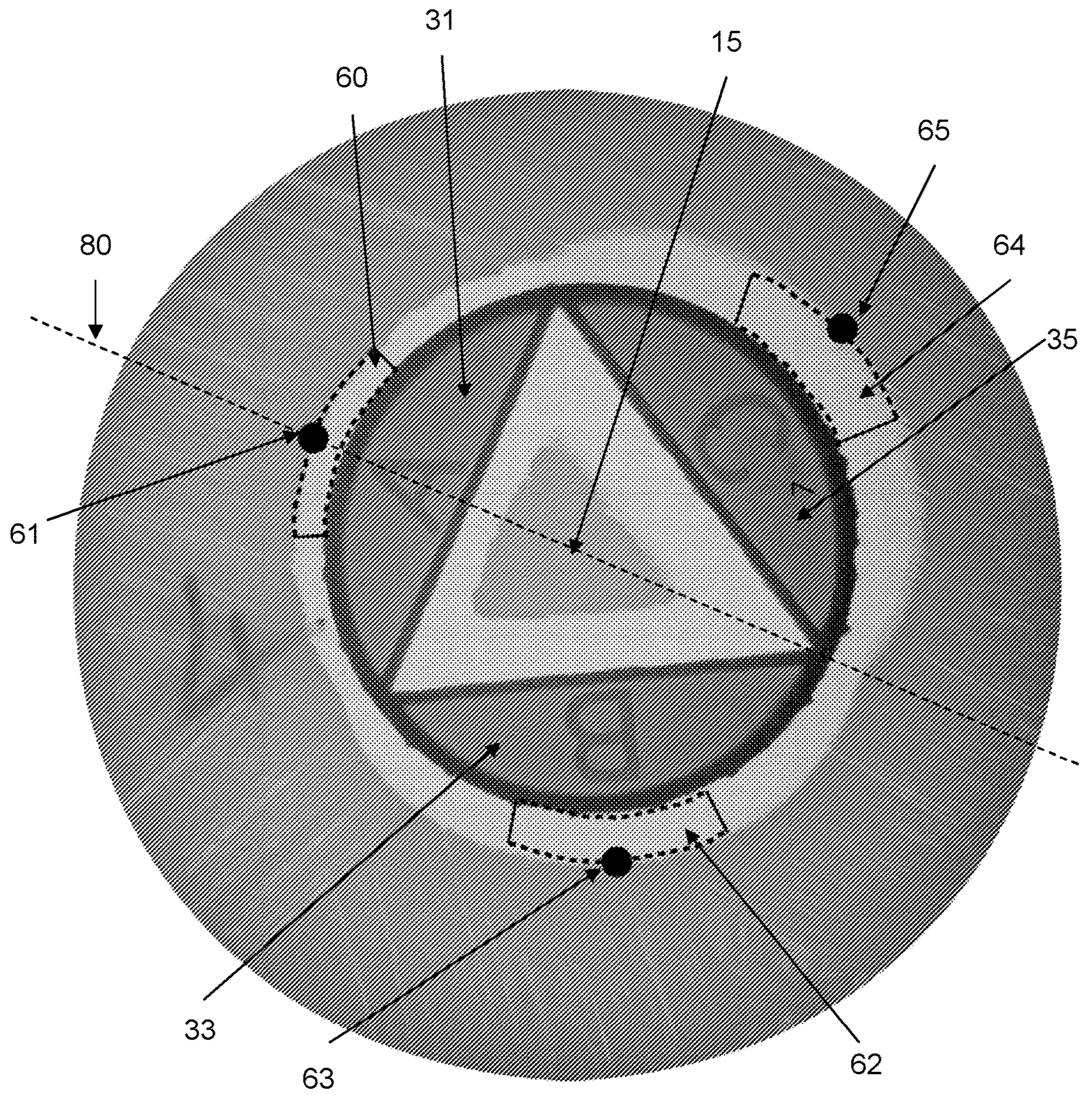
FIG. 9 is a picture taken of a culture container with a culture container insert showing inhibition zones in the cell culture substrate positioned peripherally to the agent reservoirs.

The culture container 10 as shown in FIGS. 2, 9 and 10 comprises three agent reservoirs 31, 33, 35 in a culture container insert 20, i.e., the parameter N is three. The embodiments are, however, not limited thereto but also encompasses to using more than three agent reservoirs 31, 33, 35, 37, 39 as shown in FIGS. 4-6 and 8. If the culture container 10 comprises more than three agent reservoirs 31, 33, 35, 37, 39 then, generally, concentration gradients of non-adjacent agent reservoirs would typically overlap in the middle of the culture container insert 20, leading to more complex calculations in order to determine any agent interaction effects.

Hence, in a preferred embodiment the parameter N is three thereby allowing testing the agent interaction effects of all combinations of agents contained in the agent reservoirs 31, 33, 35 in a single experiment.

In an embodiment, each agent reservoir 31, 33, 35 is enclosed between a circumferential wall 24 aligned with the circumference of the circle and by a chord wall 21, 23, 25 as shown in FIG. 1. In such an embodiment, the three chord walls 21, 23, 25 enclose a triangle 40. Hence, in such an embodiment, the central window or part is in the form of triangle 40.

In a preferred embodiment, the volume of each agent reservoir 31, 33, 35 is the same and thereby each chord wall 21, 23, 25 has the same length. In such an embodiment, the triangle 40 enclosed by the three chord walls 21, 23, 25 is an equilateral triangle 40. The embodiments are, however, not limited thereto. For instance, the triangle 40 enclosed by the three chord walls 21, 23, 25 could be an isosceles triangle 40. In such an embodiment, two of the agent reservoirs 31, 33 may have the save volume and the same length of their chord walls 21, 23, whereas the remaining agent reservoir 35 may have a different volume and length of its chord wall 25. In such a case, the resolution in the agent concentration gradients will be different for different agents and agent reservoirs 31, 33, 35.

The cell population 55 cultured in and/or on the cell culture substrate 50 could be any population of single cells or mixture of cells. The cells could, for instance, be bacterial cells, yeast cells, fungal cells, archaea cells, plant cells, animal cells, including human cells, such as immortalized cell lines, primary cancer cells and sample derived cultures as illustrative, but non-limiting, examples. Cells could also be phage-infected bacteria and virus-infected eukaryotic cells. For instance, the cell population 55 could be obtained from biological sample, such as taken from a patient. The biological sample could then be a body fluid sample, such as a blood sample, a plasma sample, a serum sample, a lymphatic fluid sample, a cerebrospinal fluid sample, or a urine sample, or a body tissue sample, such as a biopsy sample, or cells isolated and optionally purified from a body fluid or a tissue sample.

The present invention can be used not only with isolated or purified cell samples but may in fact be used to determine agent interaction effects for one or more cells in a combined cell sample, i.e., a sample comprising two or more different types or strains of cells as shown in Example 5. This means relaxes the need for any cell or strain purification step prior to analyzing the cells according to the present invention. In a preferred embodiment, the different cells or strain in the cell mixture are preferably identifiably on and/or in the cell culture substrate, and in particularly visually identifiable. For instance, individual cells or strains could be identified and separated by the shape of the individual cells, such as rod-shaped bacterial cells versus cocci having a general round shape, by fluorescence measurements or microscopy if one or more of the cells or strains in the mixture express a fluorescent protein, or by colorimetric measurements or microscopy if one or more of the cells or strains in the mixture express a dye or colorimetric label, etc.

A typical application of the method of the invention is in the context of determining FICi values for combinations of antimicrobial agents, such as antibiotics, on a bacterial population. The bacterial population may, for instance, be from a blood culture or other body fluid or tissue sample from a subject suffering from a bacterial infection. The method can then be used to find suitable combinations of antimicrobial agents that are effective in inhibiting growth of the bacterial population and that therefore could be administered to the subject in order to combat the bacterial infection.

In such a particular embodiment and with the usage of a cell container 10 as shown in FIGS. 1, 2, 9 and 10, step S1 in FIG. 12 comprises adding the cell culture substrate gel into the culture container 10 comprising three agent reservoirs 31, 33, 35 at predefined positions relative to each other and allowing the cell culture substrate gel to solidify into the cell culture substrate 50. In this particular embodiment, each agent reservoir 31, 33, 35 of the three agent reservoirs 31, 33, 35 comprises an antimicrobial agent. Step S2 comprises placing a bacterial population 55 on and/or in the cell culture substrate 50, preferably on the surface 51 of the cell culture substrate 50, and culturing the bacterial population 55 on and/or in the cell culture substrate 50, preferably on the surface 51 of the cell culture substrate 50, for a predefined period of time, preferably selected within an interval of from 12 hours to 24 hours, while the antimicrobial agents in the three agent reservoirs 31, 33, 35 diffuse through the cell culture substrate 50 and form at least partly overlapping agent concentration gradients in the cell culture substrate 50 within the combination areas 41, 43, 45 and substantially non-overlapping agent concentration gradients in the cell culture substrate 50 peripheral to the outer boundary of the three agent reservoirs 31, 33, 35. Step S3 comprises determining, for each agent reservoir 31, 33, 35, an inhibition end point 61, 63, 65 of an inhibition zone 60, 62, 64 substantially lacking any growth of the bacterial population 55. In this embodiment, the end point 61, 63, 65 of the inhibition zone 60, 62, 64 is positioned along an axis 80 passing through the center 15 of the circle and the agent reservoir 31, 33, 35 and at a position along the axis 80 peripheral to the outer boundary of the agent reservoir 31, 33, 35. Step S4 comprises determining, for each combination of two adjacent agent reservoirs 31, 33, 35, a growth end point 71, 73, 75 of a growth zone 70, 72, 74 comprising growth of the bacterial population 55 within a combination area 41, 43, 45 with at least partly overlapping agent concentration gradients of the antimicrobial agents contained in the two adjacent agent reservoirs 31, 33, 35.

In this particular embodiment, the method further comprises steps S10 and S11 as shown in FIG. 13. In such a case step S10 comprises determining, for each agent reservoir 31, 33, 35, a MIC of the antibacterial agent contained in the agent reservoir 31, 33, 35 with regard to the bacterial population 55 based on the inhibition end point 61, 63, 65 and a diffusion coefficient of the antibacterial agent contained in the agent reservoir 31, 33, 35 with regard to the cell culture substrate 50. Step S11 comprises determining, for each agent reservoir 31, 33, 35 of the two adjacent agent reservoirs 31, 33, 35, a MIC of the antimicrobial agent contained in the agent reservoir 31, 33, 35 in a mixture of the agents contained in the two adjacent agent reservoirs 31, 33, 35 based on the growth end point 71, 73, 75 and the diffusion coefficient.

The method then comprises determining, in step S5, a FICi based on the MICs.

The present invention also relates to a culture container insert 20 that can be used in the method for determining agent interaction effects on a cell population. In an embodiment, the culture container insert 20 comprises a circular bottom plate 22 with a central N-gonal opening 40, preferably a central equilateral N-gonal opening 40. In an embodiment, the culture container insert 20 comprises a circular wall 24 attached to a circumference of the circular bottom plate 22. The cell culture substrate 20 also comprises, in this embodiment, N chord walls 21, 23, 25 attached to the circular wall 24 and the circular bottom plate 22 and enclosing the central N-gonal opening 40. The circular bottom plate 22, the circular wall 24 and each chord wall 21, 23, 25 define an agent reservoir 31, 33, 35 and N is an integer equal to or larger than three.

In an embodiment, the circular bottom plate 22 comprises at least one identifier 32, 34, 36 present within at least one agent reservoir 31, 33, 35. FIG. 1 illustrates such identifiers 32, 34, 36. It is generally sufficient if at least one agent reservoir 31, 33, 35 comprises such an identifier 32, 34, 36 since the remaining agent reservoirs 31, 33, 35 can then be identified with regard to their predefined positions relative to this agent reservoir 31, 33, 35. However, in a preferred embodiment, each agent reservoir 31, 33, 35 comprises a respective identifier 32, 34, 36 as shown in FIG. 1. The identifiers 32, 34, 36 could be any identifier in the bottom plate 22, such as a letter, number or other marking.

The cell culture insert 20 can be made of various materials including, but not limited to, polymers, plastics, metals, including metal alloys, glass and ceramics. The material should be inert to agents to be contained in the agent reservoirs 31, 33, 35, i.e., should not react with the agents. The material should preferably also be able to be sterilized, such as by autoclaving, chemical sterilization and/or radiation sterilization.

The cell culture insert 20 could be disposable and thereby discarded after a use. Alternatively, the cell culture insert 20 could reusable and thereby used in several experiments following cleaning and sterilization.

Non-limiting, but illustrative, examples of plastics include plastics traditionally used in cell culturing, for instance, polystyrene (PS), polypropylene (PP), polyvinyl chloride (PVC), polyethylene (PE), polyethylene terephthalate (PET), polytetrafluoroethylene (PTFE), polyether ether ketone (PEEK) acrylonitrile butadiene styrene (ABS), nylon polyamide (PA), polycarbonate (PC), polyoxymethylene (POM), poly(methyl methacrylate) (PMMA), polyphenylene sulfide (PPS) and copolymers thereof.

Non-limiting, but illustrative, examples of metals include titanium, aluminum, coper, zinc and manganese as well as alloys thereof and steel.

Non-limiting, but illustrative, examples of ceramics include carbon and silicon based crystalline and non-crystalline ceramics.

The cell culture insert 20 can be manufactured using various manufacturing processes including, but not limited to, 3D printing, molding, machining, casting and sculpting.

In an embodiment, the cell culture insert 20 is made of an optically clear or at least optically translucent material.

The invention also relates to a culture container 10 comprising a bottom disc 12 and a circumferential wall 14 attached to the bottom disc 12 as exemplified in FIG. 2. The culture container 10 also comprises a culture container insert 20 according to the invention positioned in the culture container 10 with the circular bottom plate 22 placed on the bottom disc 12 and the circular wall 24 distanced from the circumferential wall 14.

In this embodiment, the culture container insert 20 is separate from the culture container 10 and is designed to be put into the culture container 10 as shown in FIG. 2. In this embodiment, the culture container 10 could be any culture container 10, such as cell culture plate or dish, such as Petri dish, into which the culture container insert 20 is put. The culture container 10 could then comprise one culture container insert 20 as shown in FIG. 2 or multiple, i.e., at least two, culture container inserts 20 could be positioned in the culture container 10 depending on the size (diameter) of the culture container inserts 20 versus the size (diameter) of the culture container 10.

The at least one culture container insert 20 is positioned with its circular bottom plate 22 placed on the bottom disc 12 of the culture container 10, preferably at a central position of the bottom disc 12. In particular, the culture container insert 20 should be positioned in the culture container 10 so that there is a space or distance between the circular wall 24 of the culture container insert 20 and the circumferential wall 14 of the culture container 10. This provides room for the agents to diffuse peripherally towards the circumferential wall 14 to thereby form the substantially non-overlapping agent concentration gradients peripheral to the outer boundary of the agent reservoirs 31, 33, 35.

Figures 3, 4:
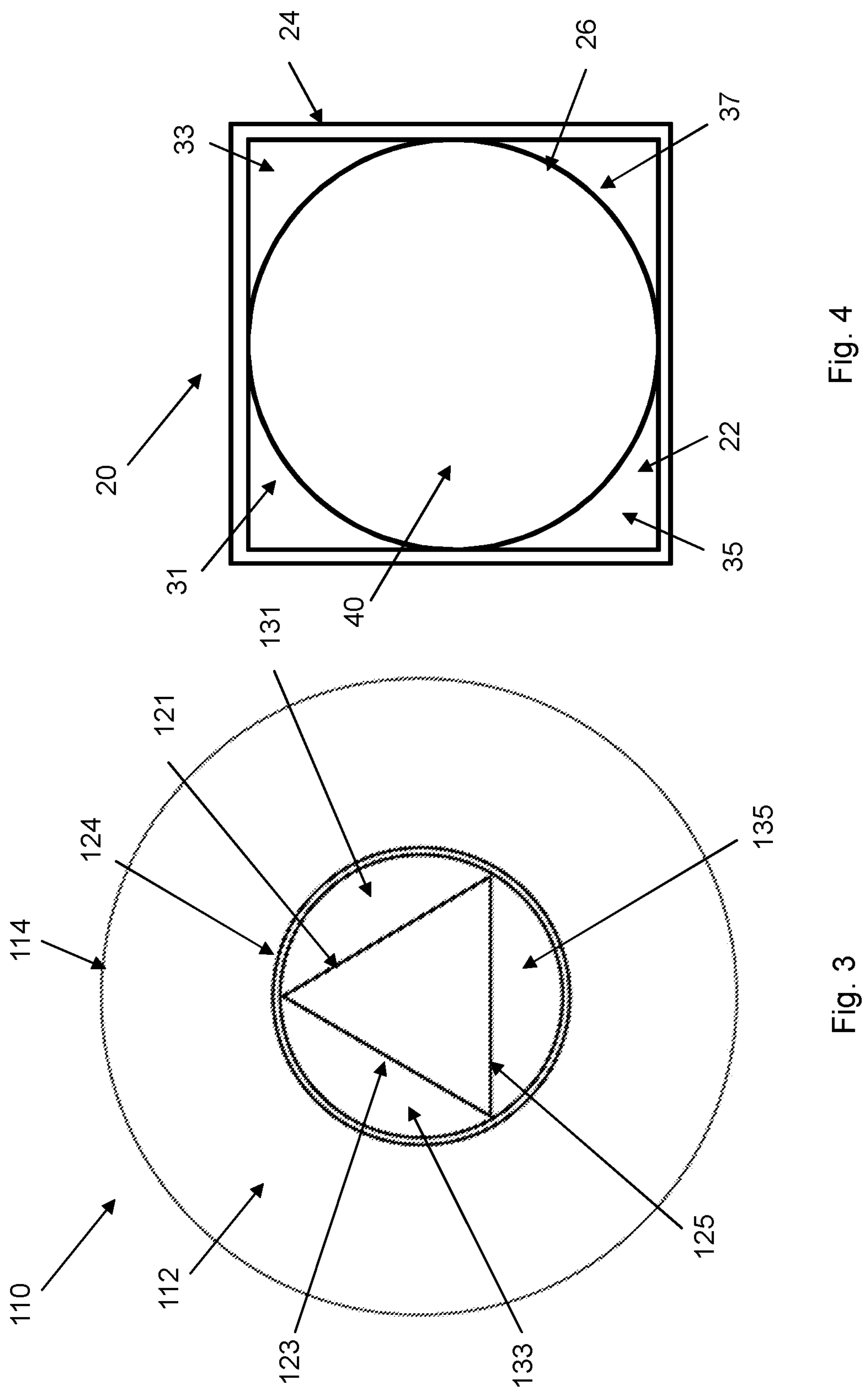
FIG. 3 schematically illustrates a culture container according to an embodiment.
FIG. 4 schematically illustrates a culture container insert according to another embodiment.

In the embodiment above, the culture container insert 20 is separate from the culture container 10. FIG. 3 illustrates another embodiment with the culture container 110 and insert as a single piece. In such an embodiment, the culture container 110 comprises a bottom disc 112 and a circumferential wall 114 attached to the bottom disc 112. The culture container 110 also comprises a circular wall 124 attached to the bottom disc 112 and enclosed by and distanced from the circumferential wall 114. The culture container 110 further comprises N chord walls 121, 123, 125 attached to the circular wall 124 and the bottom disc 112 and enclosing a N-gon part 40, preferably an equilateral N-gon part 40, of the bottom disc 112. In this embodiment, the bottom disc 112, the circular wall 124 and each chord wall 121, 123, 125 define an agent reservoir 131, 133, 135 and N is an integer equal to or larger than three.

In an embodiment, the bottom disc 112 comprises at least one identifier present within at least one agent reservoir 131, 133, 135.

As described in the foregoing, the parameter N is preferably three, but may also be larger than three, such as four, five, six or even more.

The culture container 10 as shown in FIG. 2 or the culture container 110 as shown in FIG. 3 could be made of a material as previously described herein for the culture container insert 20, such as polymers, plastics, metals, including metal alloys, glass and ceramics.

In an embodiment, each agent reservoir 31, 33, 35; 131, 133, 135 in the culture container insert 20 or in the culture container 110 comprises an agent comprising plug made of a solidified mixture of a gel and an agent. In such an embodiment, each agent comprising plug preferably comprises an agent that is different from the agents in the other agent comprising plugs.

In another embodiment, each agent reservoir 31, 33, 35; 131, 133, 135 in the culture container insert 20 or in the culture container 110 comprises an agent in lyophilized or dried from. In such an embodiment, each lyophilized or dried agent is preferably different from the other lyophilized or dried agents.

In these embodiments, the culture container insert 20 or the culture container 110 is preloaded with the agents either in lyophilized or dried form or in the form of the agent comprising plugs.

FIGS. 4 to 8 illustrate alternative culture container inserts 20 of the embodiments. These culture container inserts 20 could then be used together with a culture container 10 in the method for determining agent interaction effects instead of the culture container insert 20 as shown in FIG. 1. Alternatively, the culture container 110 of FIG. 3 could be equipped with agent reservoirs 31, 33, 35, 37, 39 arranged and defined as in any of FIGS. 4 to 9 instead of the agent reservoirs 131, 133, 135 as shown in FIG. 3.

FIG. 4 illustrates a culture container insert 20 comprising a rectangular, preferably quadratic, wall 24 defining the outer boundary of the culture container insert 20. The culture container insert 20 also comprises a circular wall 26 inscribed in the quadratic wall 24, i.e., the diameter of the circular wall 26 is preferably equal to the side length of the quadratic wall 24. The circular wall 26, the quadratic wall 24 and a bottom plate 22 of the culture container insert 20 define four agent reservoirs 31, 33, 35, 37. The circular wall 26 encloses a central circular opening or window 40.

Figure 5:
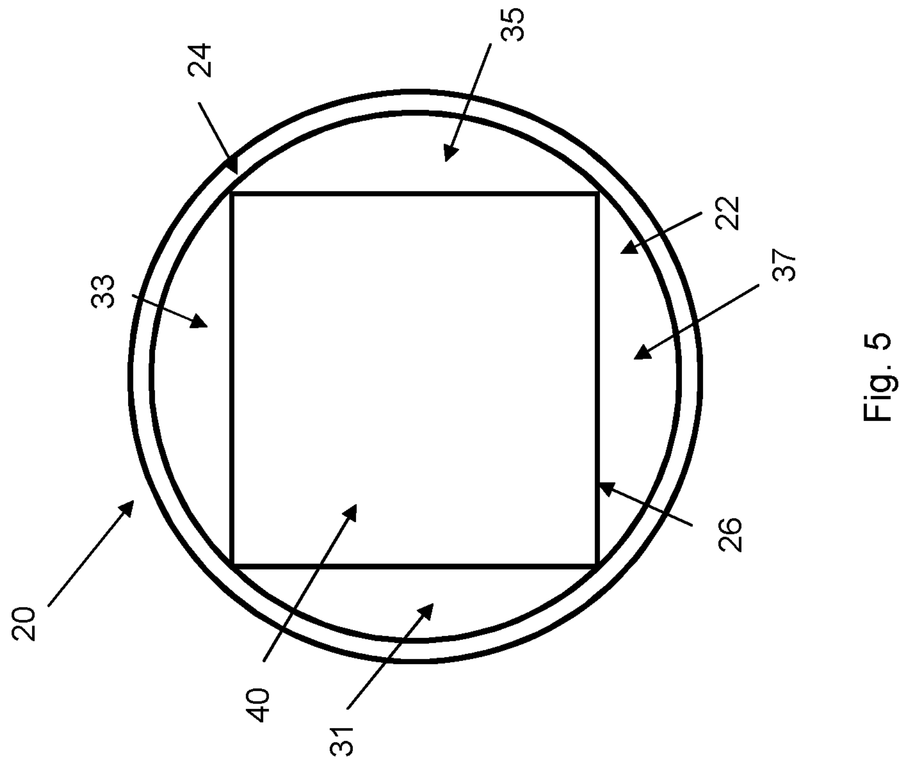
FIG. 5 schematically illustrates a culture container insert according to a further embodiment.

FIG. 5 illustrates another embodiment of a culture container insert 20 comprising a circular wall 24 defining the outer boundary of the culture container insert 20. The culture container insert 20 also comprises a quadratic wall 26 circumscribed by the circular wall 24, i.e., the diagonal of the quadratic wall 26 is preferably equal to the diameter of the circular wall 24. The quadratic wall 26, the circular wall 24 and a bottom plate 22 of the culture container insert 20 define four agent reservoirs 31, 33, 35, 37. The quadratic wall 26 encloses a central quadratic opening or window 40.

Figure 6:
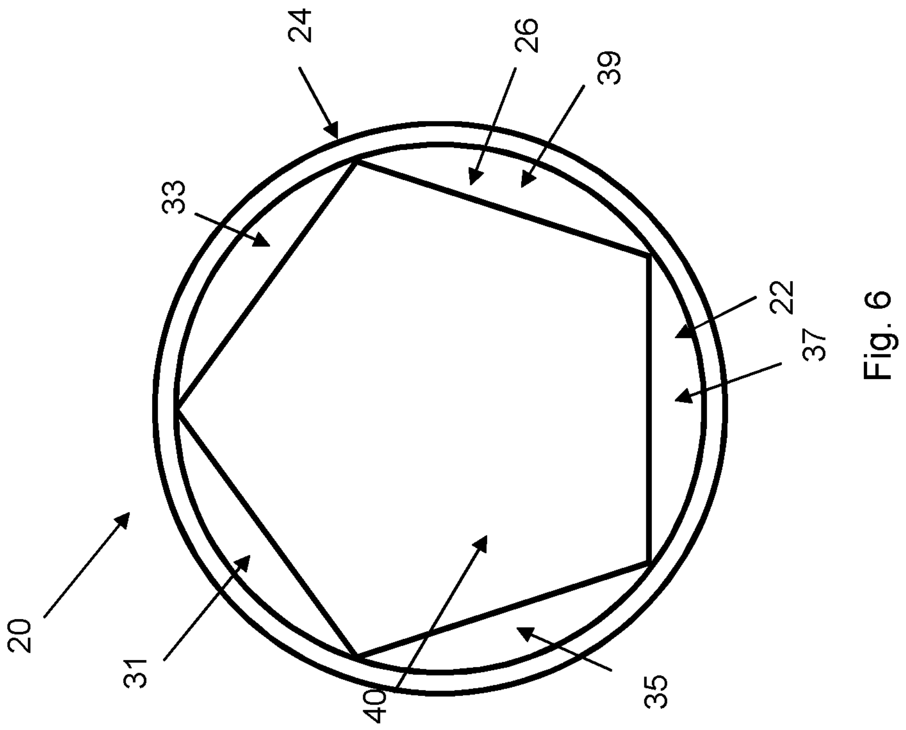
FIG. 6 schematically illustrates a culture container insert according to yet another embodiment.

FIG. 6 illustrates a further embodiment of a culture container insert 20 comprising a circular wall 24 defining the outer boundary of the culture container insert 20. The culture container insert 20 also comprises a pentagon wall 26 circumscribed by the circular wall 24. The pentagon wall 26, the circular wall 24 and a bottom plate 22 of the culture container insert 20 define five agent reservoirs 31, 33, 35, 37, 39. The pentagon wall 26 encloses a central pentagon opening or window 40.

The embodiments as shown in FIGS. 1, 5 and 6 could be regarded as having a circular wall 24 and a N-gonal wall 26 circumscribed by the circular wall 24. In FIG. 1, N is three, i.e., a triangle, in FIG. 5, N is four, i.e., a square, and in FIG. 6 N is five, i.e., a pentagon. This concept can be extended further for values of N larger than five.

Figure 7:
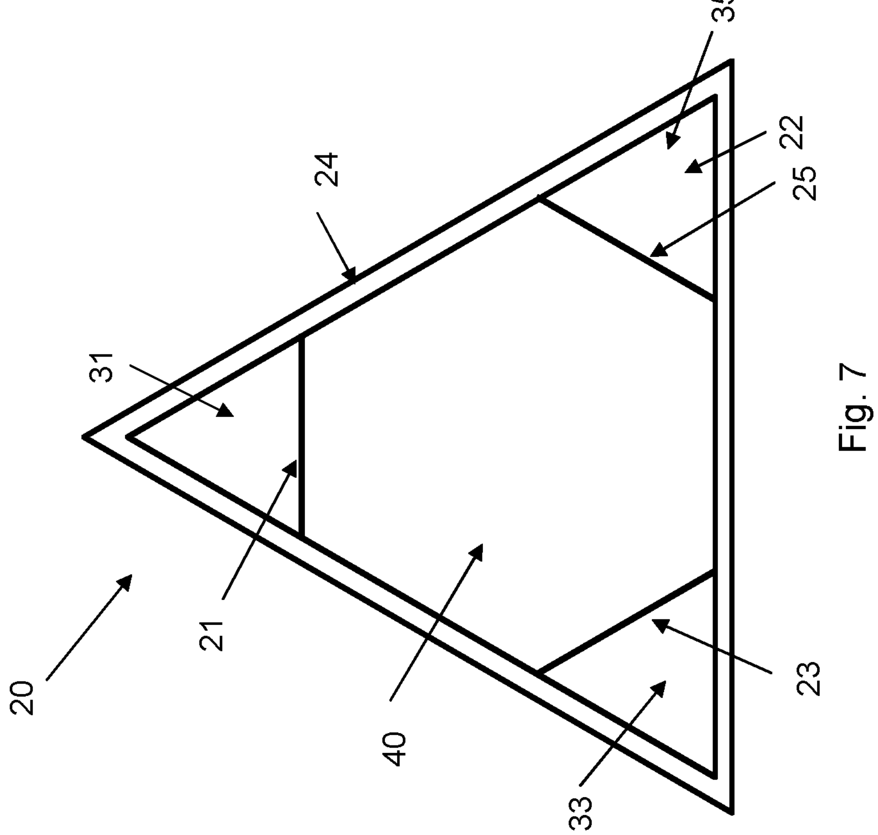
FIG. 7 schematically illustrates a culture container insert according to an embodiment.

FIG. 7 illustrates an embodiment of a culture container insert 20 comprising a triangular wall 24 defining the outer boundary of the culture container insert 20. The culture container insert 20 also comprises three walls 21, 23, 25 dividing the area of the triangle into three agent reservoirs 31, 33, 35 and a central window or opening 40. In a preferred embodiment, these three walls 21, 23, 25 are of a same length and each wall 21, 23, 25 is preferably parallel to one of the sides of the triangular wall 24. The three walls 21, 23, 25, the triangular wall 24 and a bottom plate 22 of the culture container insert 20 define three agent reservoirs 31, 33, 35.

FIG. 8 illustrates a further embodiment of a culture container insert 20 comprising an outer rectangular, preferably quadratic, wall 24 defining the outer boundary of the culture container insert 20. The culture container insert 20 also comprises an inner rectangular, preferably quadratic, wall 26 circumscribed by the outer quadratic wall 24, i.e., the diagonal of the inner quadratic wall 26 is preferably equal to the side length of the outer quadratic wall 24. The inner quadratic wall 26, the outer quadratic wall 24 and a bottom plate 22 of the culture container insert 20 define four agent reservoirs 31, 33, 35, 37. The inner quadratic wall 26 encloses a central quadratic opening or window 40.

Another aspect of the invention relates to a kit for determining agent interaction effects on a cell population 55. The kit comprises a culture container 10; 110 according to any of the embodiments. The kit also comprises a volume of cell culture substrate gel configured to be added into the culture container 10; 110 and allowed to solidify into a cell culture substrate 50. Each agent reservoir of the N agent reservoirs 31, 33, 35; 131, 133, 135 comprises a respective agent and the N agent reservoirs 31, 33, 35 enclose combination areas 41, 43, 45. The kit also comprises instructions to take at least one picture of the cell culture substrate 50, preferably of a surface 51 of the cell culture substrate 50, following a predefined period of time from placing a cell population 55 in and/or the cell culture substrate 50, preferably on the surface 51. The agents in the N agent reservoirs 31, 33, 35 diffuse through the cell culture substrate 50 and form at least partly overlapping agent concentration gradients in the cell culture substrate 50 within the combination areas 41, 43, 45 and substantially non-overlapping agent concentration gradients in the cell culture substrate 50 peripheral to an outer boundary on the N agent reservoirs 31, 33, 35.

The kit further comprises instructions to determine, from the at least one picture and for each agent reservoir 31, 33, 35; 131, 133, 135 of the N agent reservoirs 31, 33, 35; 131, 133, 135, an inhibition end point 61, 63, 65 of an inhibition zone 60, 62, 64 substantially lacking any growth of the cell population 55. The inhibition end point 61, 63, 65 is positioned peripherally to the agent reservoir 31, 33, 35; 131, 133, 135. The kit also comprises instructions to determine, from the at least one picture and for each combination of two adjacent agent reservoirs 31, 33, 35; 131, 133, 135 of the N agent reservoirs 31, 33, 35; 131, 133, 135, a growth end point 71, 73, 75 of a growth zone 70, 72, 74 comprising growth of the cell population 55 within a combination area 41, 43, 45 with at least partly overlapping agent concentration gradients of the agents contained in the at least two adjacent agent reservoirs 31, 33, 35; 131, 133, 135.

The kit comprises information defining diffusion coefficients for the agents contained in the N agent reservoirs 31, 33, 35; 131, 133, 135 with regard to the cell culture substrate 50. The kit also comprises instructions to determine, for each combination of two adjacent agent reservoirs 31, 33, 35; 131, 133, 135, an agent interaction effect between the agents contained in the two adjacent agent reservoirs 31, 33, 35; 131, 133, 135 based on the inhibition end points 61, 63, 65 determined for the two adjacent agent reservoirs 31, 33, 35; 131, 133, 135, the growth end point 71, 73, 75 determined for the two adjacent agent reservoirs 31, 33, 35; 131, 133, 135 and the information defining diffusion coefficients.

In a particular embodiment, the kit comprises instructions to determine FICi values based on MIC values determined based on the inhibition end points 61, 63, 65, the growth end points 71, 73, 75 and the information defining diffusion coefficients as previously described herein.

In an embodiment, the kit also comprises the N agents and a gel to be mixed the N agents and solidified into a respective agent comprising plug in the N agent reservoirs.

Figure 16:
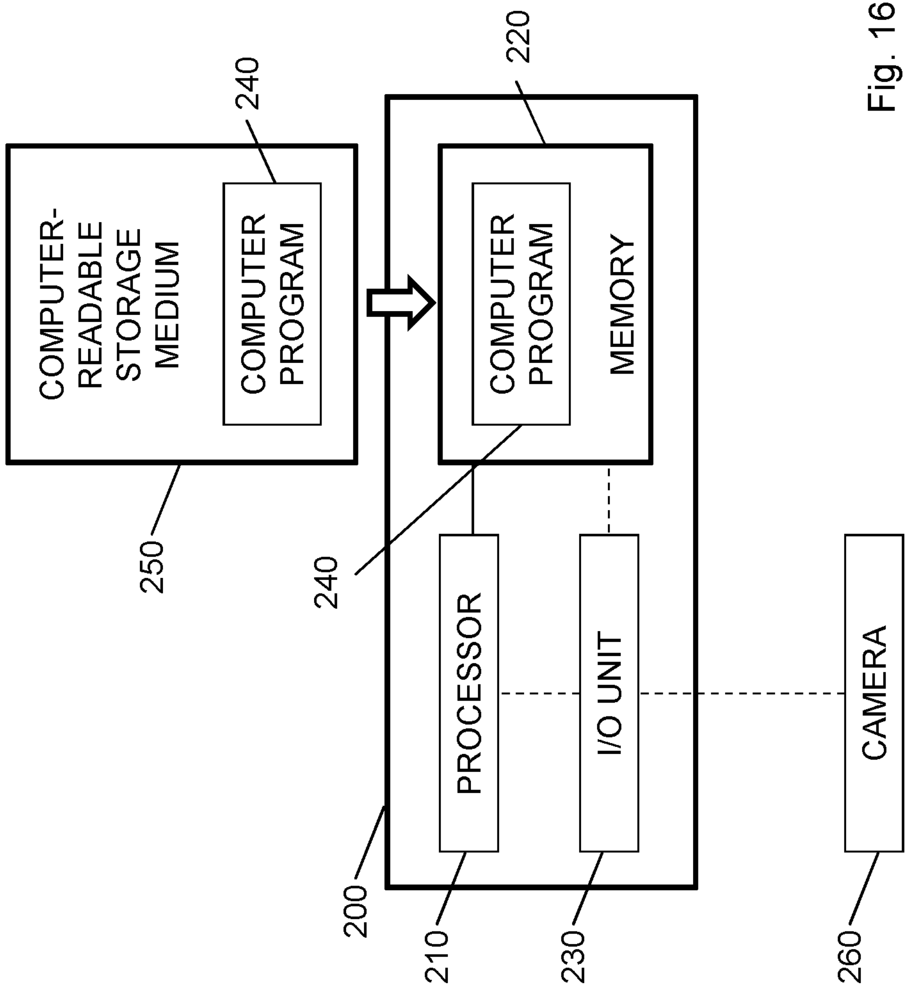
FIG. 16 schematically illustrates a computer according to an embodiment.

FIG. 16 is a schematic block diagram of a computer 200 comprising a processor 210 and a memory 220 that can be used to determine the agent interaction effect according to the embodiment. In such an embodiment, the determination of the agent interaction effect could be implemented in a computer program 240, which is loaded into the memory 220 for execution by processing circuitry including one or more processors 210 of the computer 200. The processor 210 and the memory 220 are interconnected to each other to enable normal software execution. An input and output (I/O) unit 230 is preferably connected to the processor 210 and/or the memory 220 to enable reception of image data from a camera 260.

The term processor should be interpreted in a general sense as any circuitry, system or device capable of executing program code or computer program instructions to perform a particular processing, determining or computing task. The processing circuitry including one or more processors 210 is, thus, configured to perform, when executing the computer program 240, well-defined processing tasks such as those described herein.

The processor 210 does not have to be dedicated to only execute the above-described steps, functions, procedure and/or blocks, but may also execute other tasks.

In a particular embodiment, the computer program 240 comprises instructions, which when executed by at least one processor 210, cause the at least one processor 210 to provide image data representing at least one picture taken of a surface 51 of a cell culture substrate 50 in culture container 10 at a predefined period of time following placing a cell population 55 on and/or in the cell culture substrate 50, preferably on the surface 51 of the cell culture substrate 50. The culture container 10 comprises N agent reservoirs 31, 33, 35 at predefined positions relative to each other. Each agent reservoir 31, 33, 35 of the N agent reservoirs 31, 33, 35 comprises an agent and the N agent reservoirs 31, 33, 35 enclose combination areas 41, 43, 45. N is an integer equal to or larger than three. The agents in the N agent reservoirs 31, 33, 35 diffuse through the cell culture substrate 50 and form at least partly overlapping agent concentration gradients in the cell culture substrate within the combination areas 41, 43, 45 and substantially non-overlapping agent concentration gradients in the cell culture substrate 50 peripheral to an outer boundary on the N agent reservoirs 31, 33, 35. The at least one processor 210 is also caused to determine, based on the image data and for each agent reservoir 31, 33, 35 of at least two adjacent agent reservoirs 31, 33, 35 of the N agent reservoirs 31, 33, 35, an inhibition end point 61, 63, 65 of an inhibition zone 60, 62, 64 substantially lacking any growth of the cell population 55. The inhibition end point 61, 63, 65 is positioned peripherally to the outer boundary of the agent reservoir 31, 33, 35. The at least one processor 210 is further caused to determine, based on the image data and for the at least two adjacent agent reservoirs 31, 33, 35, a growth end point 71, 73, 75 of a growth zone 70, 72, 74 comprising growth of the cell population 55 within a combination area 41, 43, 45 with at least partly overlapping agent concentration gradients of the agents contained in the at least two adjacent agent reservoirs 31, 33, 35. The at least one processor 210 is additionally caused to determine an agent interaction effect between the agents contained in the at least two adjacent agent reservoirs 31, 33, 35 based on the inhibition end points 61, 63, 65 and the growth end point 71, 73, 75.

In an embodiment, the instructions, which when executed by at least one processor 210, cause the at least one processor 210 to determine, based on the image data and for each agent reservoir 31, 33, 35 of the at least two adjacent agent reservoirs 31, 33, 35, a MIC of the agent contained in the agent reservoir 31, 33, 35 with regard to the cell population 55 based on the inhibition end point 61, 63, 65. The at least one processor 210 is, in this embodiment, also caused to determine, based on the image data and for each agent reservoir 31, 33, 35 of the at least two adjacent agent reservoirs 31, 33, 35, a MIC of the agent contained in the agent reservoir 31, 33, 35 in a mixture of the agents contained in the at least two adjacent agent reservoirs 31, 33, 35 based on the growth end point 71, 73, 75. The at least one processor is further caused to determine a FICi based on the MICs.

In an embodiment, the instructions, which when executed by at least one processor 210, cause the at least one processor 210 to determine, based on the image data and for each agent reservoir 31, 33, 35 of the at least two adjacent agent reservoirs 31, 33, 35, the MIC of the agent contained in the agent reservoir 31, 33, 35 based on a diffusion coefficient of the agent contained in the agent reservoir 31, 33, 35 with regard to the cell culture substrate 55 and the inhibition end point 61, 63, 65. The at least one processor 210 is, in this embodiment, caused to determine, based on the image data and for each agent reservoir 31, 33, 35 of the at least two adjacent agent reservoirs 31, 33, 35, the MIC of the agent contained in the agent reservoir 31, 33, 35 in the mixture of the agents contained in the at least two adjacent agent reservoirs 31, 33, 35 based on the diffusion coefficient and the growth end point 71, 73, 75.

In an embodiment, the instructions, which when executed by at least one processor 210, cause the at least one processor 210 to control a camera 260 to take the at least one picture taken of the surface 55 of the cell culture substrate 50 in culture container 10 at the predefined period of time following placing the cell population 55 on the surface 51 of the cell culture substrate 50.

The proposed technology also provides a computer-readable storage medium 250 comprising the computer program 240. By way of example, the software or computer program 240 may be realized as a computer program product, which is normally carried or stored on a computer-readable medium 250, in particular a non-volatile medium. The computer-readable medium 250 may include one or more removable or non-removable memory devices including, but not limited to a Read-Only Memory (ROM), a Random Access Memory (RAM), a Compact Disc (CD), a Digital Versatile Disc (DVD), a Blu-ray disc, a Universal Serial Bus (USB) memory, a Hard Disk Drive (HDD) storage device, a flash memory, a magnetic tape, or any other conventional memory device. The computer program 240 may, thus, be loaded into the operating memory 220 of the computer for execution by the processor 210 thereof.

EXAMPLES

Example 1—CombiANT™

In this Example, an assay for testing antibiotic synergy that is robust and highly quantitative is presented. The assay, denoted CombiANT™ herein, is a diffusion-based assay that provides quantitative information of all pairwise interactions of, in this Example, 3 antibiotics in a single agar plate. The technical validation study showed that CombiANT™ performed equally well to checkerboard methodology, but due to its unique design and function, offered much reduced method complexity that was comparable to a disk diffusion test. Like checkerboard assays, CombiANT™ produced a fractional inhibitory concentration index (FICi), but at higher throughput and with easier multiplexing. The assay could be applied without previous information of the samples' susceptibility. The potential of CombiANT™ for antibiotic interaction screening was shown by applying the assay to a new field of combination therapy—the treatment of urinary tract infections (UTI). Conserved and variable antibiotic interactions were identified that indicated a high potential for personalized-medicine in refined combination therapy.

Materials and Methods

Fabrication and Design

The culture container insert was designed with computer aided design software (Autodesk Fusion 360) and manufactured by 3D printing (Formlabs, Somerville, MA; SLA 3D printer) using proprietary formulations for autoclavable or dental resin. The 3D printing was performed in the U-PRINT facility of Uppsala University.

Strains and Media

For the technical validation, the reference strains *Escherichia coli* K12-MG1655 (DA5438), *Pseudomonas aeruginosa* PA14 (DA64160), and *Staphylococcus aureus* ATCC29213 (DA64485) were used. For the UTI study, we screened a range of 6 to 295 clinical isolates of independent origin that were susceptible to the antibiotics ciprofloxacin (CIP), fosfomycin (FOF), mecillinam (MEC), nitrofurantoin (NIT), trimethoprim (TMP), ampicillin (AMP), gentamicin (GEN), and cefotaxime (CTX). Bacteria were cultured on Mueller Hinton agar and in Mueller Hinton broth (Becton Dickinson, Sparks, MD; Refs. 275730, 225250) with incubations at 37° C. Overnight cultures were prepared from single colonies in 1 ml and 190 rpm orbital shaking. For the UTI isolate screening, the agar was supplemented with 25 mg/l glucose-6-phosphate, as this is required for the action of FOF. Antibiotic stocks were prepared according to manufacturer's recommendations and stored at −20° C. in aliquots for single use: AMP 100 mg/ml or 180 mg/ml in water (Sigma-Aldrich, Ref. A9518-25G), CIP 25 mg/ml in 0.1 M HCl (Sigma-Aldrich, Ref. 17850-25G-F), CTX 3 mg/ml or 50 mg/ml in water (Sigma, Ref. C7039-1G), GEN 45 mg/ml or 50 mg/ml in water (Sigma, Ref. 48760-5G-F), FOF 50 mg/ml in water (Sigma-Aldrich, Ref. P5396-5G), MEC 10 mg/ml in water (Sigma-Aldrich, Ref. 33447-100MG), NIT 10 mg/ml in DMSO (Sigma, Ref. N7878-10G), and TMP 10 mg/ml in DMSO (Sigma, Ref. T-7883-5G).

Broth Microdilution

To calibrate CombiANT™, we determined MIC values for antibiotics individually, using standard broth microdilution methodology in agreement with EUCAST guidelines. Two-fold serial dilutions of antibiotics in Mueller Hinton broth were prepared in 96-well microtiter plates. The plates were then inoculated with approximately $3\times10^5$ cells from a dense overnight culture (1:1000 dilution, 180 μl final volume) and incubated without shaking at 37° C. for 24 h, after which wells were mixed by pipetting and growth was measured by optical density at 540 nm (Thermo Scientific, Multiscan FC Type 357). MIC was called at the lowest concentration that yielded a growth signal of non-inoculated control wells. Measurements were performed with two biological replicates and their average value was designated MIC. For determination of MIC to FOF, the media was supplemented with 50 mg/l of glucose-6-phosphate, which is required for FOF-mediated inhibition.

Input Concentrations

For the technical calibration of the CombiANT™ assay, the antibiotic concentrations were determined based on the MIC of the antibiotic against the strains used (Table 1). In the screening of the UTI isolates, two sets of antibiotic concentrations were used for all strains (Table 2 for FIGS. 20C-20J isolates and Table 3 for FIGS. 20A-20C and 20M isolates). When MIC is known for an antibiotic, using a MIC based determination of the concentration in the culture container insert is preferable, as it will lead to the most readable results. For tests with FOF, glucose-6-phosphate was provided in the final agar layer at a concentration of 25 mg/l.

TABLE 1 antibiotic input concentrations for validation study

| Antibiotic | Abbreviation | Insert concentration |
|---|---|---|
| Ampicillin | AMP | 40 × MIC |
| Cefotaxime | CTX | 8 × MIC |
| Ciprofloxacin | CIP | 18 × MIC |
| Fosfomycin | FOF | 40 × MIC |
| Gentamicin | GEN | 30 × MIC |
| Mecillinam | MEC | 12 × MIC |
| Nitrofurantoin | NIT | 20 × MIC |
| Trimethoprim | TMP | 15 × MIC |

TABLE 2 antibiotic input concentrations for the exploratory study

| Antibiotic | Abbreviation | Organism | Classification | Insert concentration |
|---|---|---|---|---|
| Ampicillin | AMP | *E. coli* | S | 160 mg/L |
| Cefotaxime | CTX | *E. coli* | S | 1 mg/L |
| Ciprofloxacin | CIP | *E. coli* | S | 0.72 mg/L |
| Fosfomycin | FOF | *E. coli* | S | 5.2 mg/L |
| Gentamicin | GEN | *E. coli* | S | 18 mg/L |
| Mecillinam | MEC | *E. coli* | S | 4.8 mg/L |
| Nitrofurantoin | NIT | *E. coli* | S | 240 mg/L |
| Trimethoprim | TMP | *E. coli* | S | 6 mg/L |

S = susceptible

TABLE 3 antibiotic input concentrations for the expanded screening study

| Antibiotic | Abbreviation | Organism | Insert concentration |
|---|---|---|---|
| Ampicillin | AMP | *E. coli* | 60 mg/L |
| Cefotaxime | CTX | *E. coli* | 1.2 mg/L |
| Gentamicin | GEN | *E. coli* | 15 mg/L |
| Mecillinam | MEC | *E. coli* | 4.8 mg/L |
| Nitrofurantoin | NIT | *E. coli* | 240 mg/L |
| Trimethoprim | TMP | *E. coli* | 6 mg/L |

Checkerboard Experiments

Standard checkerboard assays (8×8 concentrations) for FICi determination were performed in single biological replicate and with two-fold serial dilutions ranging from 4×MIC to ¼ MIC, as previously described [6]. Inoculum size was $5\times10^5$ cells (0.5 McFarland), and optical density was read at 540 nm (Thermo Scientific, Multiscan FC Type 357) after 16 h of static incubation. For Bliss model synergy quantification, higher-resolution checkerboards (9×9 concentrations) were obtained using linear concentrations up to 1×MIC, and with 3 biological replicates. Treatment positions were fully randomized to avoid bias from edge and gradient effects. Degree of synergy was calculated as previously described [8]. Growth yield was expressed relative to untreated wells using background-corrected optical density values. The expected relative growth $Y_{1+2}$ according to a Bliss independence model [9] was calculated by multiplication of the relative growth yields $Y_1$ and $Y_2$ obtained in the single-antibiotic treatments. The degree of synergy S of a combination was defined as: $S=Y_{1+2}-Y_{observed}$. S=0 expresses additivity, positive values denote synergy, and negative values denote antagonism.

Physics Diffusion Model and Image Analysis

A Finite Elements Model (FEM) was used to model diffusion of reagents from the reservoirs. Diffusion was assumed to follow Fick's laws of diffusion and concentration of the agent was calculated by solving the convection-diffusion equation for no advective flux and no net volumetric source. The FEM analysis, antibiotic diffusion modeling and calibration as well as the antibiotic landscape assembly were performed using COMSOL Multiphysics (Comsol, Stockholm, Sweden). The algorithm was scripted using Matlab (Mathworks, Natick, MA) and COMSOL-Matlab bridge. CombiANT™ plates were photographed using a vertically mounted CCD digital camera (Raspberry Pi v2 camera module).

Statistical Analyses

Statistical analyses were performed using Graph Pad Prism and Matlab. Statistical difference of measured FICi to the additive model (FICi=1) was assessed using Wilcoxon signed rank tests. In the UTI screen, interactions that showed clinically relevant levels of antibiotic interaction (FICi<0.5, FICi>4) were tested, as well as one sample Wilcoxon signed rank test against FIC=1 was performed on isolates showing to have either clinical synergy or antagonism (Table 4 and 5).

Results

CombiANT™ Assay and System Design

The CombiANT™ assay was designed to fulfil the following criteria: (i) the generation of quantitative information of antibiotic interaction; (ii) a reduction of assay complexity and work hours for assay preparation and analysis; (iii) high ability for multiplexing; and (iv) an easy integration into clinical microbiology laboratory routines. CombiANT™ assay is a diffusion-based assay that provides quantitative information of the pair-wise synergy of 3 antibiotics in a single agar plate. The assay consisted of a culture container insert (FIG. 1) that could be integrated into any standard cell culture plate (FIG. 2). Multiple culture container inserts could be used on the same cell culture plate. The culture container insert comprised 3 reservoirs (marked 'A', 'B', and 'C' in FIG. 1) for antibiotics and a central triangular imaging area (FIG. 1).

To run a CombiANT™ synergy assay, 0.5 ml of antibiotic-containing agar was loaded into the agent reservoirs by pipetting. For most applications, the agent reservoirs were loaded with different antibiotics. Upon agar solidification, the assay entered an inactive state. At this point, the culture container inserts could be stored under refrigeration, with no loss of function for at least one week. This allowed for multiple assays, encompassing different antibiotics, to be prepared and stored according to the users need so that they can be easily implemented without delay.

To implement a specific synergy test, the prepared culture container insert was placed into a culture plate and overcast with a final layer of culture agar, typically 25 ml for a standard 90 mm plate (FIG. 2). This step activated the assay, which was ready for use once the plate solidified (FIG. 2). The final agar layer allowed the antibiotics suspended in the agent reservoirs to start diffusing into the surrounding agar area and to the agar surface. The sample was applied to the solidified plates by streaking with a cotton swab. The assay was designed for an inoculum density of 0.5 McFarland, in accordance with EUCAST guidelines for disk diffusion tests v8.0. Following inoculation, the plates were incubated overnight to allow for sample growth. At this point the CombiANT™ plates were identical to standard agar plates. That feature allowed for CombiANT™ assays to seamlessly integrate in any laboratory management system for overnight culture and incubation of bacterial samples on plates. During growth, inhibition zones established around the culture container insert according to the diffusion-generated concentration landscape of the three antibiotics (FIG. 10). For measurement of antibiotic interactions, the plates were photographed. Results were analyzed with a curated algorithm that provided quantitative synergy measurements.

Quantitative Measurements of Drug Interactions

The quantitative measurements were obtained by image analysis. The specific geometry of the culture container insert and its geometric relation to the agar surface achieved a predetermined and controlled diffusion of the antibiotics. The controlled diffusion was modeled with a finite elements method for each antibiotic, individually. The model yielded an antibiotic specific diffusion map. That diffusion map expressed the concentration of the antibiotic for the surface of the plate, relative to the initial concentration of the antibiotic in the agent reservoir and the diffusion coefficient of the antibiotic.

Antibiotics differ in their diffusion characteristics according to their structure and the interaction with the diffusion matrix. The diffusion coefficient of an antibiotic can be determined for the precise assay conditions (type of agar, culture volume, incubation time) in a calibration step. For calibration, a reference strain with known MIC was tested with 3 concentrations of the target antibiotic (10×, 20×, 40×MIC). The calibration needs to be performed only once for every potential antibiotic. After that, the diffusion map was stored to be applied whenever that specific antibiotic is tested. In addition to the diffusion coefficient, the recommended initial concentration to be used in the antibiotic reservoirs was calculated from the one-time calibration results. The recommended initial concentrations for the 8 antibiotics used in this study, and according to EUCAST guidelines for antimicrobial susceptibility testing, are provided in Tables 1-3.

The analysis algorithm used the calibrated diffusion maps to generate a virtual agar surface. First, the user indicated which antibiotic was placed in every agent reservoir of the assay. At this point, the algorithm recalled the stored diffusion maps corresponding to the antibiotics used in the assay. It assembled them into an assay-specific antibiotic landscape. The antibiotic landscape was then mapped to the picture, according to the geometric anchor points of the culture container insert. The extent of antibiotic interaction was quantified from points on the edge of the inhibition and growth zones, according to the formula of the fractional inhibitory concentration index (FICi), as outlined below.

In a picture of a CombiANT™ agar plate certain areas of interest can be observed (FIGS. 9 and 10). On the outside of the culture container insert, every antibiotic was acting alone. Since antibiotics diffused outwards from the agent reservoirs, the point of the inhibition zone, opposite an agent reservoir, that was further away from the agent reservoir, represented the inhibitory concentration (IC) of that antibiotic when acting alone. The IC points (shown in dots in FIG. 9) were matched to the antibiotic landscape, and the corresponding concentrations of the 3 antibiotics were extracted ($IC_A$, $IC_B$, and $IC_C$).

Inside the imaging area, the three antibiotics had diffused out of the agent reservoirs and were now overlapping in pairs in the three corners. Every corner of the imaging area constituted a part of the plate where the two closest antibiotics were acting together. Therefore, the edge of the growth zone in the imaging area that was closest to a corner, corresponded to a point where the combination of the two antibiotics present was inhibitory to growth (shown in dots in FIG. 10). Similarly, to the three IC points, the three combination inhibitory points (CP) were matched to points in the antibiotic landscape, and the concentrations of both antibiotics present were extracted. Having extracted both individual ICs and CPs for all three antibiotics, the analysis algorithm proceeded to calculate fractional inhibitory concentration indices (FICi) for all antibiotic pairs. For the interaction between antibiotics A and B $FICi_{AB}=C_A/IC_A+C_B/IC_B$, where $C_A$ and $C_B$ were the concentrations of A and B respectively in their corresponding combination inhibitory point (CP). $FICi_{AC}$ and $FICi_{BC}$ were calculated similarly. A FICi value of 1 denoted additivity. FICi<1 indicated synergy, while FICi>1 indicated antagonism. Threshold values for clinically relevant levels of synergy and antagonism are usually set at <0.5, and >2-4, respectively. The identification of all IC and CP points in a picture can be done either automatically or manually. After that, the analysis yielded instantaneously the FICi data for all three antibiotic pairs (as shown in FIG. 11 from the analysis of the plate in FIG. 10).

Technical Validation of Assay System

Figure 17:
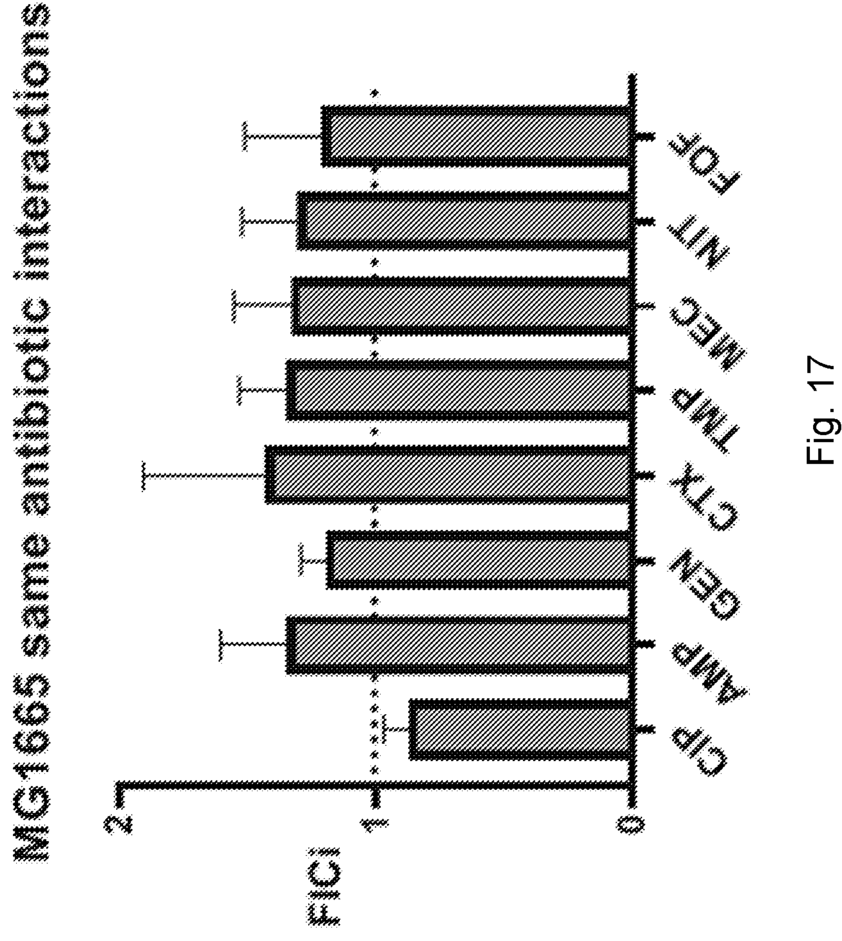
FIG. 17 illustrates self-interaction experiments of the *Escherichia coli* reference strain K12-MG1655. FICi for all self-interactions for the 8 antibiotics AMP, CIP, CTX, GEN, FOF, NIT, MEC, TMP. Bars indicate average FICi values and standard deviation (SD) of 3 biological replicates. All interactions were additive in nature and none could be detected to have a statistically significant difference to FICH by one sample Wilcoxon signed rank test.
Figure 18A:
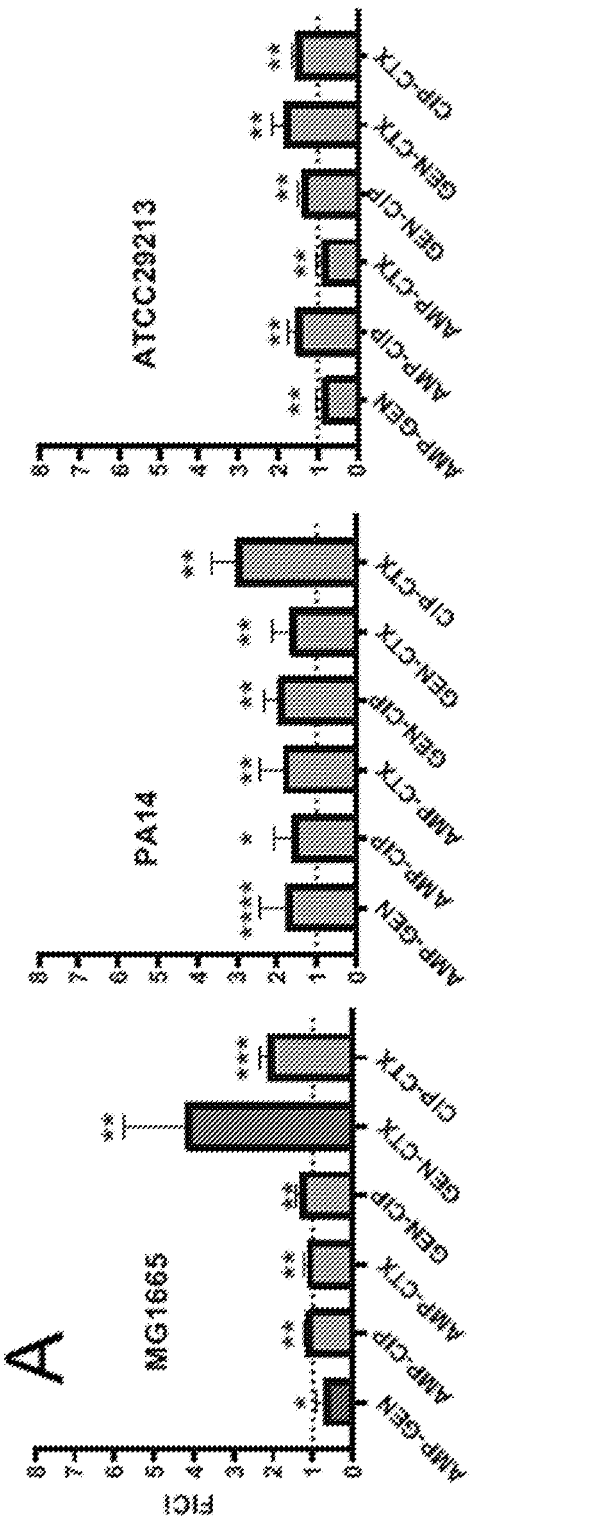
FIG. 18 illustrates technical validation of the CombiANT™ assay. (18A) Quantification of drug interactions in reference strains of *E. coli, Pseudomonas aeruginosa*, and *Staphylococcus aureus*. Synergy is expressed by fractional inhibitory concentration indices (FICi, mean±SD, n=10 replicates). (18B) Analysis of assay precision. Repeatability is expressed as relative standard error for assays conducted on the same day, dashed lines represent median standard errors and dotted lines represent the upper and lower quartiles, n=6 combinations. Reproducibility is expressed as relative differences in FICi between days dashed lines represents median relative differences and dotted lines represent the upper and lower quartiles, n=6 combinations). (18C) Coefficient of variation for the pooled data (n=10 replicates) encompassing both different day and same day replicates to quantify biological and technical replicability. Results are grouped by antibiotic interaction and then further subdivided between the three strains. (18D) Bland-Altman method comparison of CombiANT™ and checkerboard assays (mean values, n=18 strain-antibiotic pair combinations). Absolute difference of FICi of methods is plotted against their average values. The small scattering of the points is indicative of little bias between the two methods. One sample Wilcoxon signed rank test against FICi=1, * P<0.001,  P<0.01, *P<0.05.

First, as controls, we performed self-interaction experiments, where the 3 culture container insert reservoirs were filled with the same antibiotic. The self-interaction control experiments reliably produced FICi close to 1 for all antibiotics used in this Example (FIG. 17). Next, to verify that the CombiANT™ assay produced valid synergy quantifications, we ran an accuracy and precision study. We tested all pairwise antibiotic interactions in the two Gram-negative reference strains *E. coli* K12-MG1665 and *P. aeruginosa* PA14, and the Gram-positive *S. aureus* reference strain ATCC29213 against a panel of 4 antibiotics. The tested antibiotics, ampicillin (AMP), cefotaxime (CTX), ciprofloxacin (CIP), and gentamicin (GEN), spanned three distinct mechanisms of action and are commonly used in treatments of bacteremia and sepsis caused by these bacterial species. FICi indices were calculated for all 6 pair-wise interactions and all three strains (FIG. 18A).

Figure 18B:
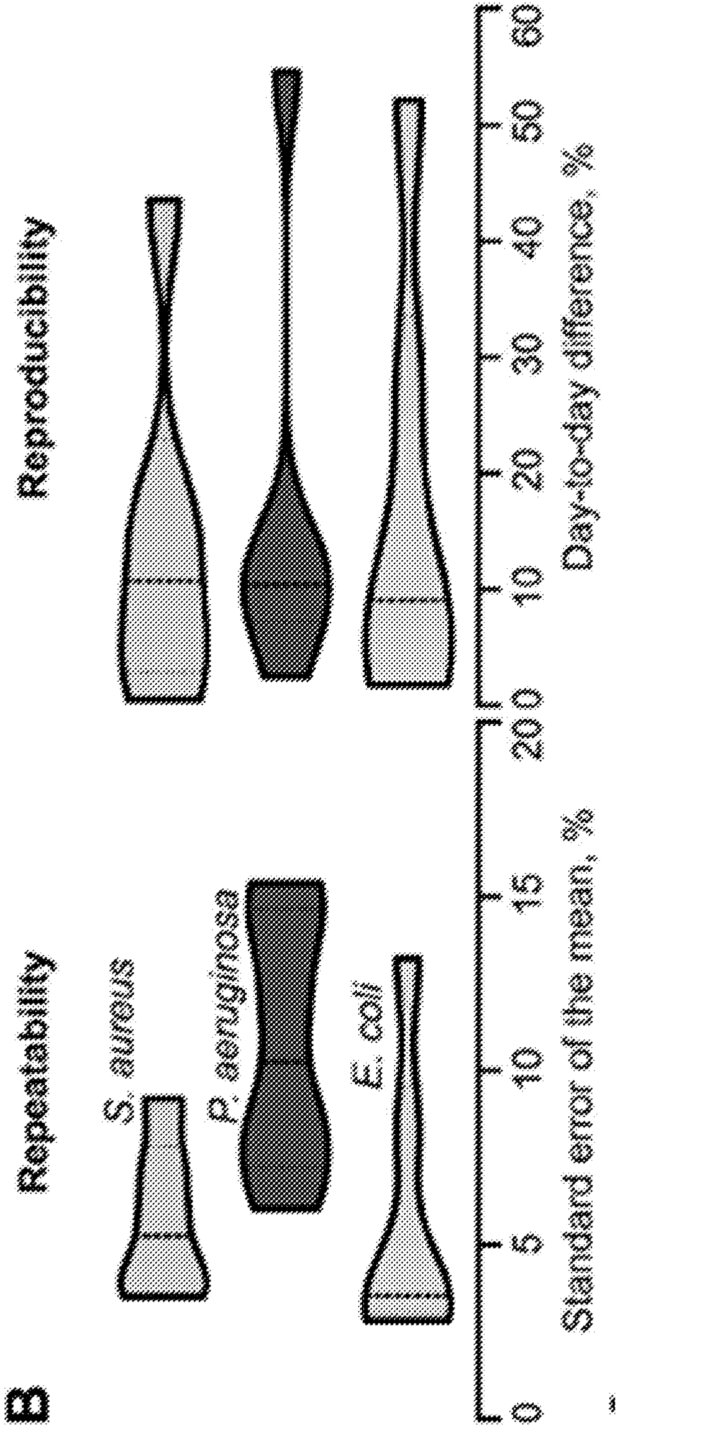
Figure 18C:
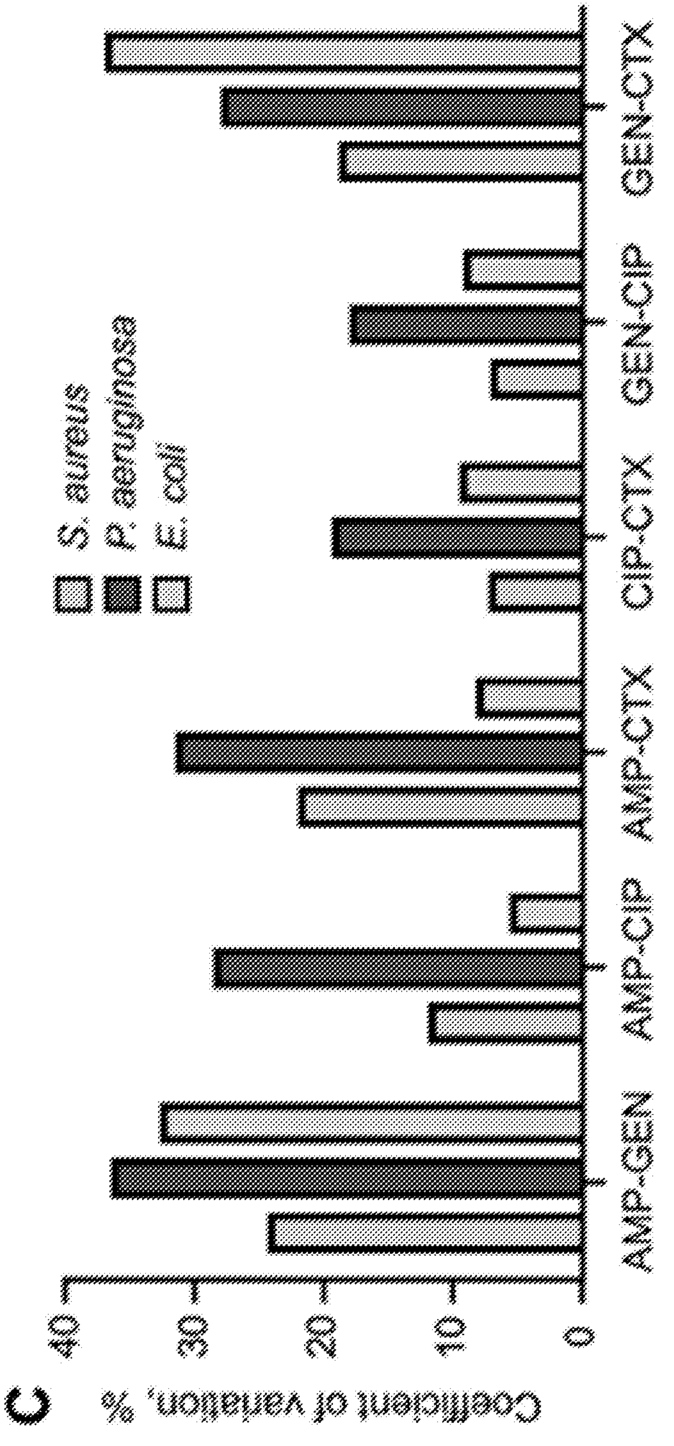

In order to fully quantify the assay's precision, the strains were screened in multiple replicates (n>10) using the CombiANT™ assay protocol. Half the replicates were tested on the same day to quantify repeatability (within-day variability). The other half was tested a following day to quantify reproducibility (day-to-day variability). To compare results between days, we chose to quantify relative day-to-day difference of the same antibiotic combination and then average all 6 combinations together for every strain (FIG. 18B). Average relative differences were below 13% for all strains with the highest quartile being below 40%. That illustrated that the assay was repeatable and independent of day-to-day variation. To quantify reproducibility, we measured the relative standard error of the mean, using same-day replicates for all antibiotic combinations. Those were then averaged for every strain. All relative standard errors were below 12% with the highest quartile being below 15%. That showed very small technical variation between replicates (FIG. 18B). Finally, we pulled all replicates together to get an overall assessment of precision that encompassed both repeatability and reproducibility. We chose to calculate the coefficient of variation for each species-combination pair, an analysis that expressed the variability of measurement in proportion to an interaction's average value (FIG. 18C). All coefficients of variation were below 37% and on average 19.7%, signifying that the method was precise enough to be replicable and repeatable.

Figure 18D:
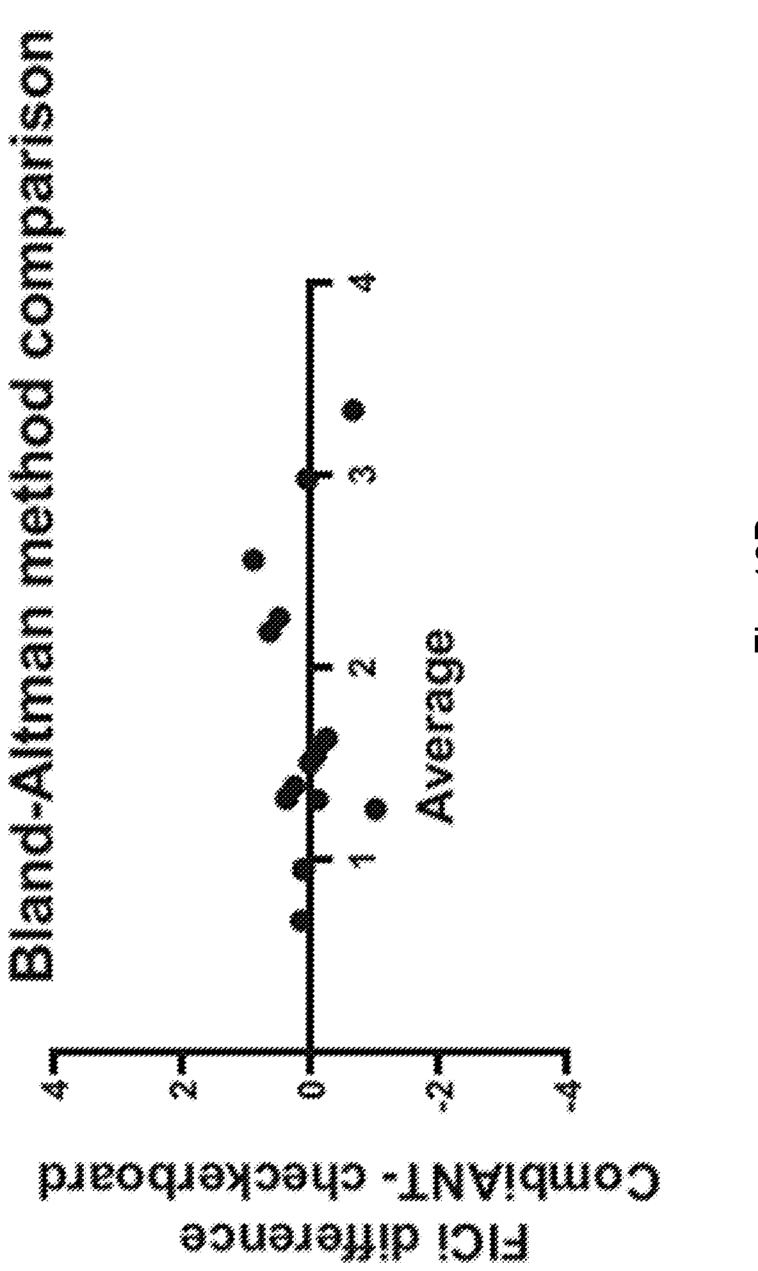

Next, we set out to quantify the accuracy of CombiANT™. To that end, we replicated all measurements of antibiotic interactions using the gold standard methodology of checkerboard assays in broth, as previously described [6]. First, we wanted to test if the two methods were systematically producing different results. We therefore performed a Bland-Altman analysis of the FICi data that was obtained with the two methods (FIG. 18D). The Bland-Altman comparison yielded a bias of 0.049 between the checkerboard and CombiANT™ assays. This low level of bias was close to the detection limit of FICi differences. We therefore concluded that there was no statistically detectable discrepancy between results obtained from the two methods.

Having shown that systemically the two methods were interchangeable, we tested the effect choosing one method over the other, using multivariate linear regression analysis. The identity of the focal antibiotic pair, had a strong and significant effect on the FICi value measured (correlation coefficient=0.55; P<0.01). The choice of method on the other hand was not statistically correlated with experiment outcome (correlation coefficient=0.07; P=0.83). Altogether, we concluded that CombiANT™ had an equal accuracy for the detection of antibiotic interactions as checkerboard assays.

A difference of CombiANT™ to checkerboard assays is that, by virtue of diffusion, CombiANT™ applies a continuous concentration range while checkerboards typically test discrete 2-fold dilutions. We therefore tested whether the high precision of CombiANT™ was a result of the finer concentration range. High-resolution linear concentration range checkerboards were obtained for all 18 strain-combination pairs, for which we quantified antibiotic interactions using a Bliss independence additive model. We again observed high agreement of antibiotic interactions with CombiANT™ results. Interestingly, synergy profiles occasionally showed dose-dependent variation, with different synergy profiles at lower doses than at MIC, making interactions harder to classify. Such dose-dependent variation was not detected by CombiANT™, as it classified interactions at a predetermined high inhibition level. We concluded that the precision of CombiANT™ was not solely determined by the linear concentration range, but also a quantification of interactions at a set, high inhibition level.

Figure 19:
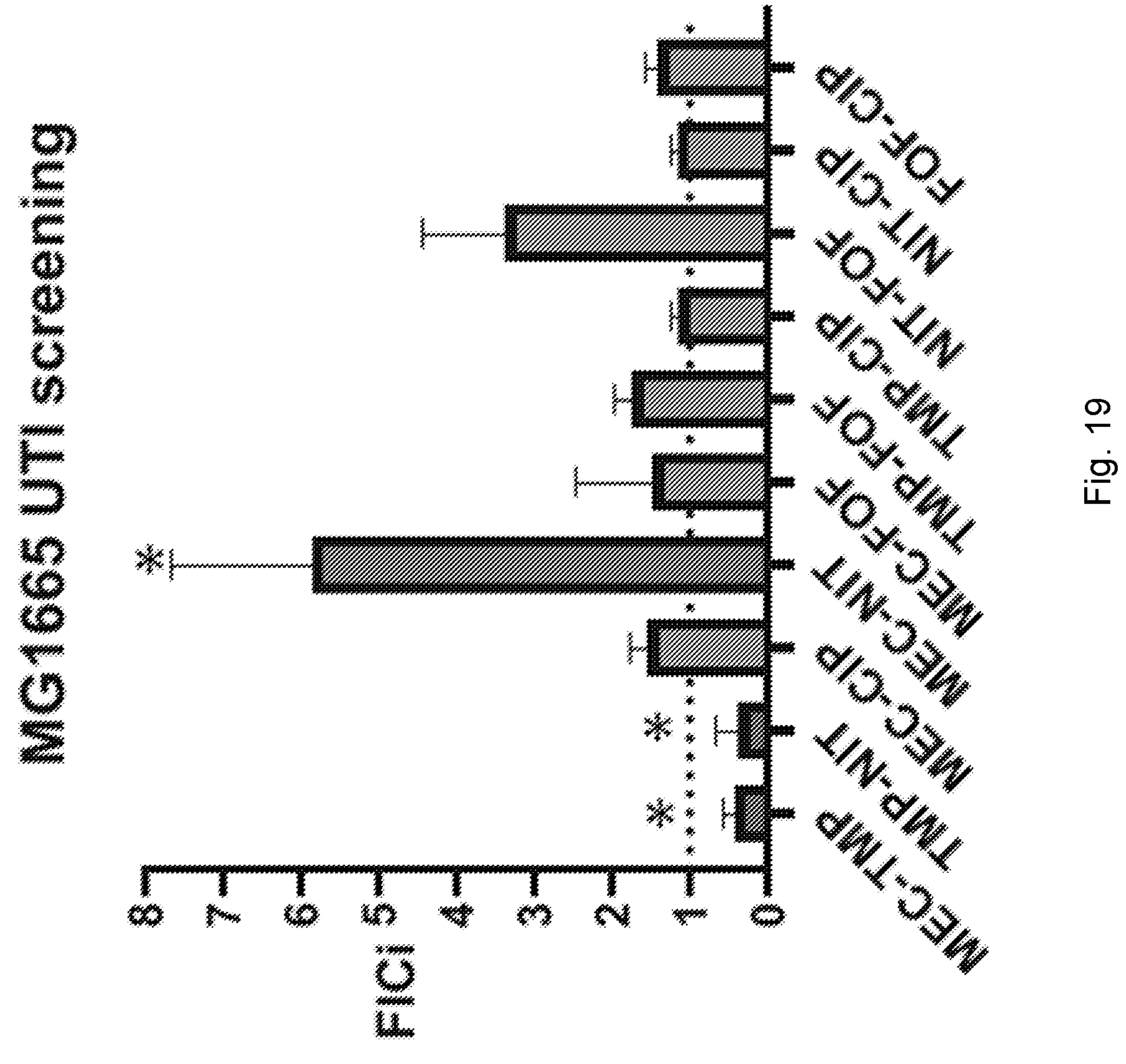
FIG. 19 illustrates CombiANT™ UTI antibiotic interactions for the *E. coli* reference strain K12-MG1655. Bars indicate average FICi values and standard deviation (SD) of 3 biological replicates. The dotted line indicates FICi=1. One sample Wilcoxon signed rank test against FICi=1, ** P<0.0001, * P<0.001, ** P<0.01, *P<0.05.

Antibiotic Interaction Panel Using CombiANT™ Assays on Clinical UTI *E. coli* Isolates We proceeded to use CombiANT™ assays to screen for antibiotic synergy against *E. coli* UTI clinical isolates and the *E. coli* K12-MG1655 reference strain. A panel of 5 antibiotics that are commonly used as single or combination treatment for UTIs was selected: nitrofurantoin (NIT), trimethoprim (TMP), mecillinam (MEC), ciprofloxacin (CIP), and fosfomycin (FOF). CombiANT™ assays were implemented to measure all pairwise interactions of the antibiotics panel against *E. coli* strains and the *E. coli* K12-MG1655 reference strain (FIG. 19). The majority of the *E. coli* strains were designated susceptible to all antibiotics in the panel (FIGS. 20A to 20M). The categorical FICi limit for an interaction to be designated to show clinically relevant levels of positive synergy was set at FICi<0.5, according to previous recommendations. A conservative limit for antagonism was set at FICi>4. All in-between values were designated as describing additivity.

Figure 20A:
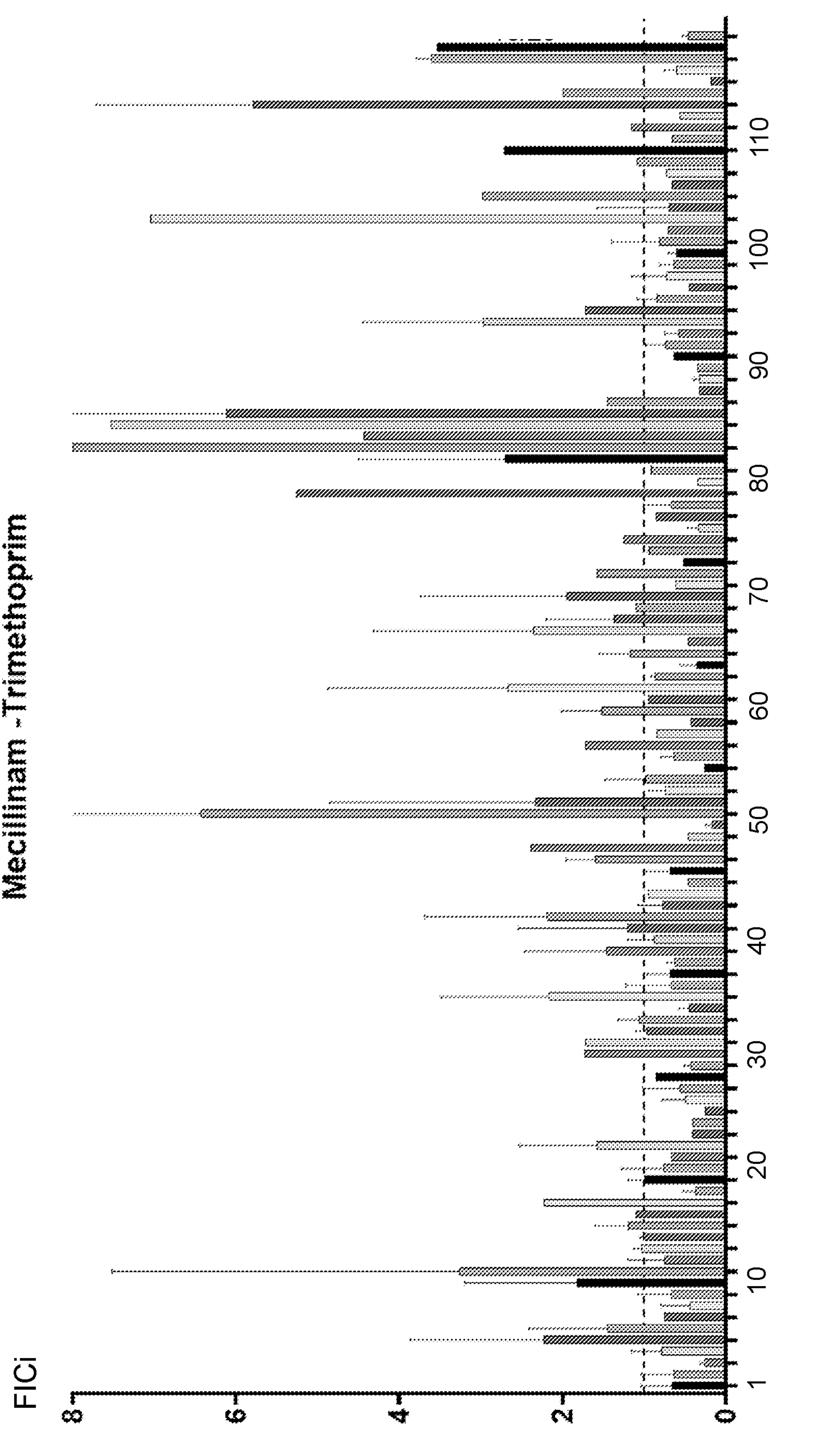
FIGS. 20A to 20M illustrate interaction screening of *E. coli* UTI clinical isolates. Antibiotic interactions expressed by FICi (mean±SD). One sample Wilcoxon signed rank test against FICi=1, * P<0.001,  P<0.01, *P<0.05.
Figure 20B:
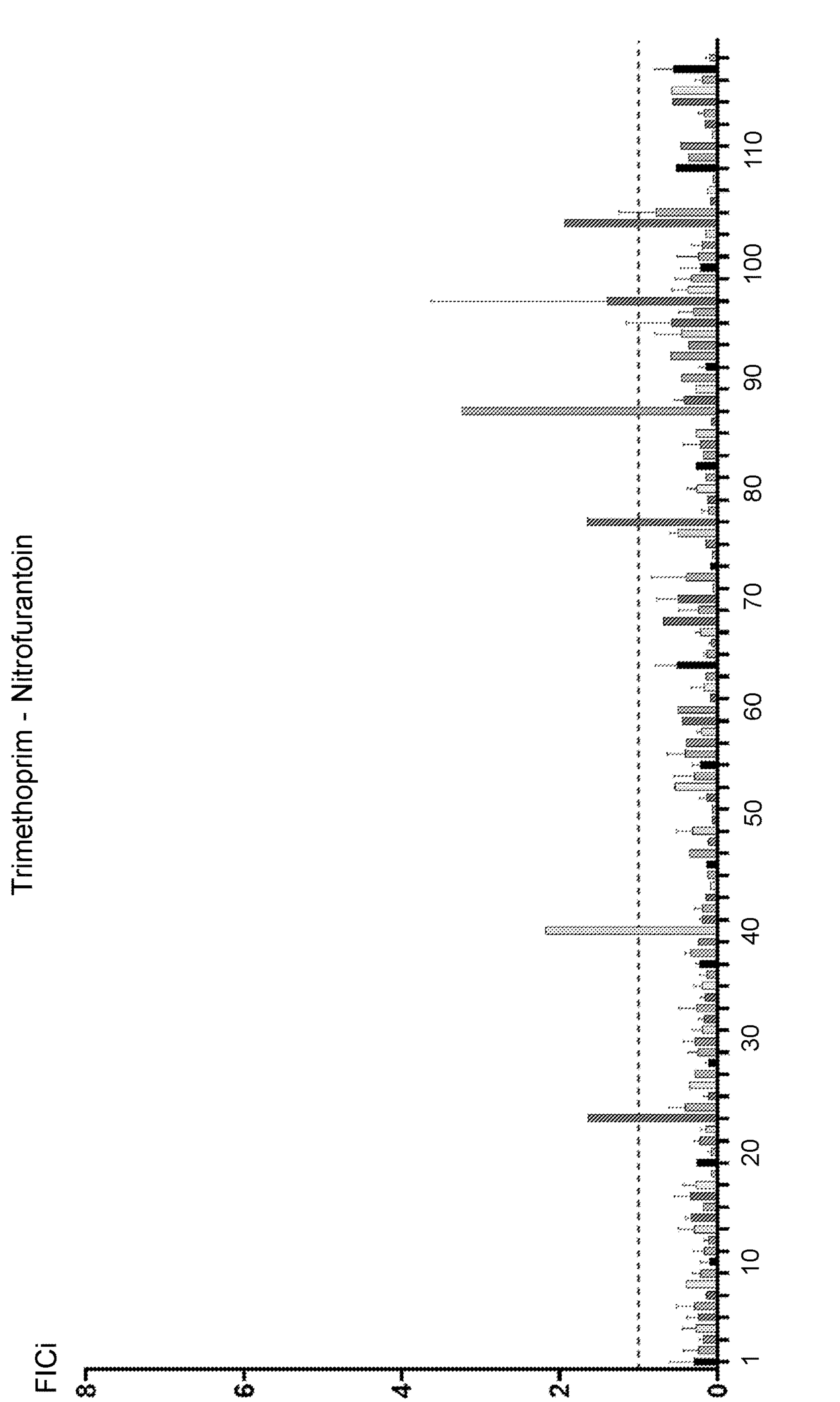
Figure 20C:
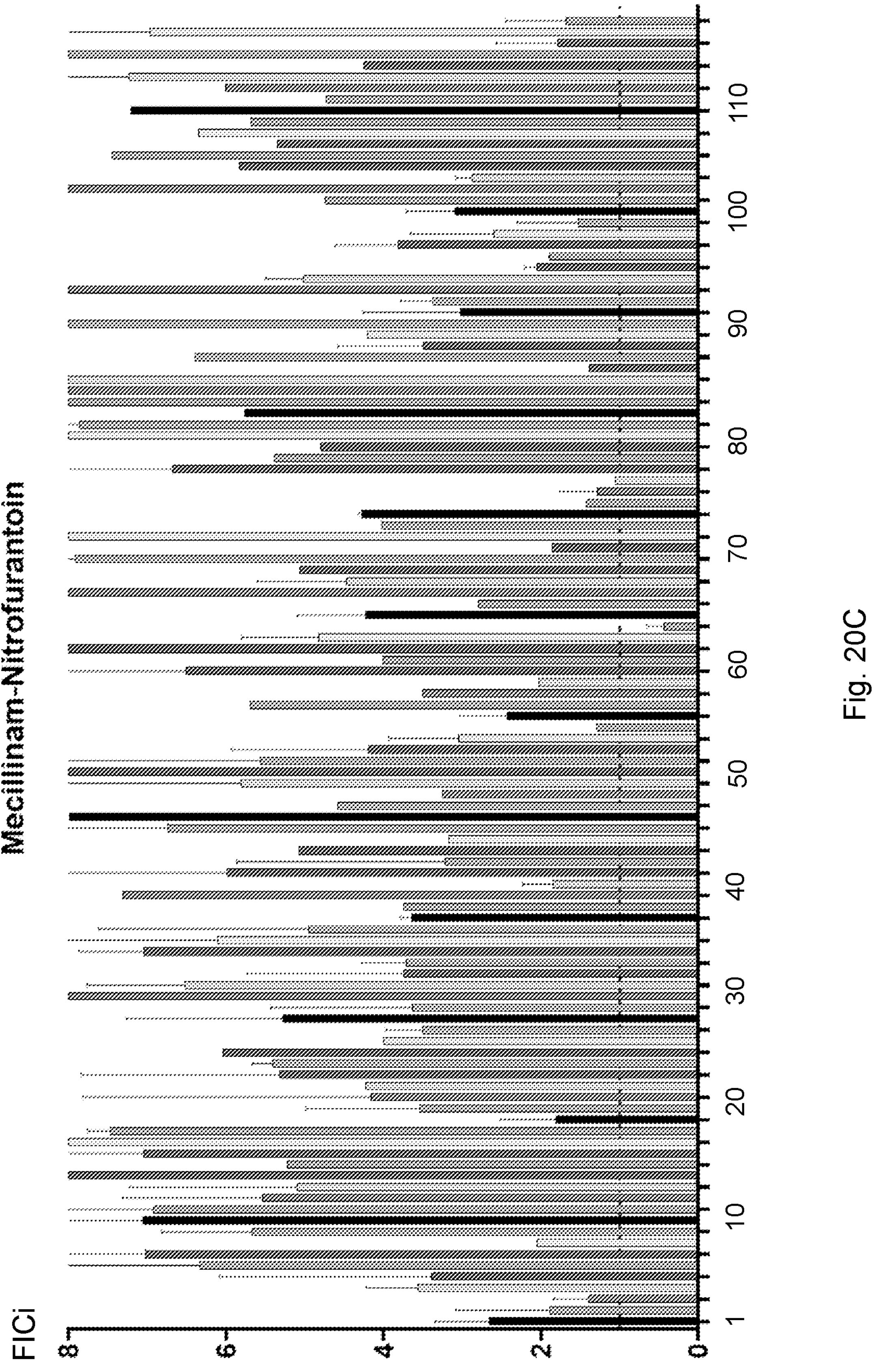
Figure 20E:
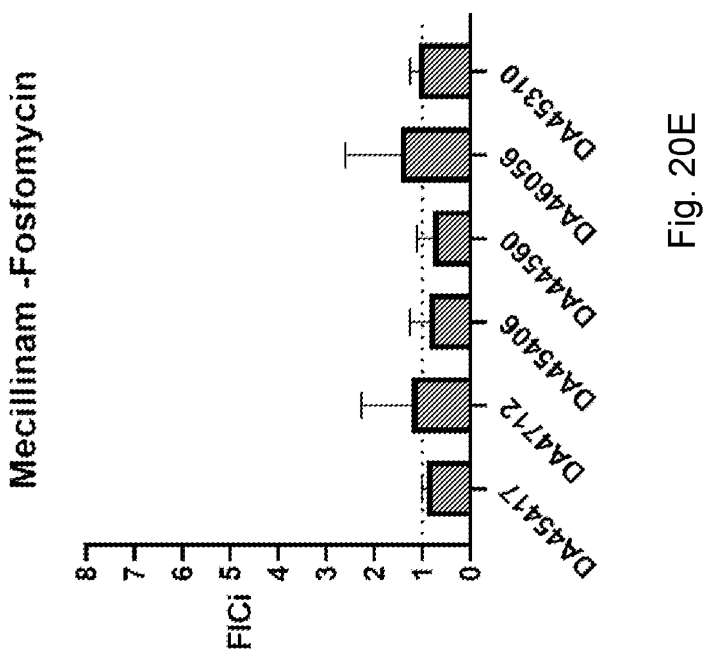
Figure 20D:
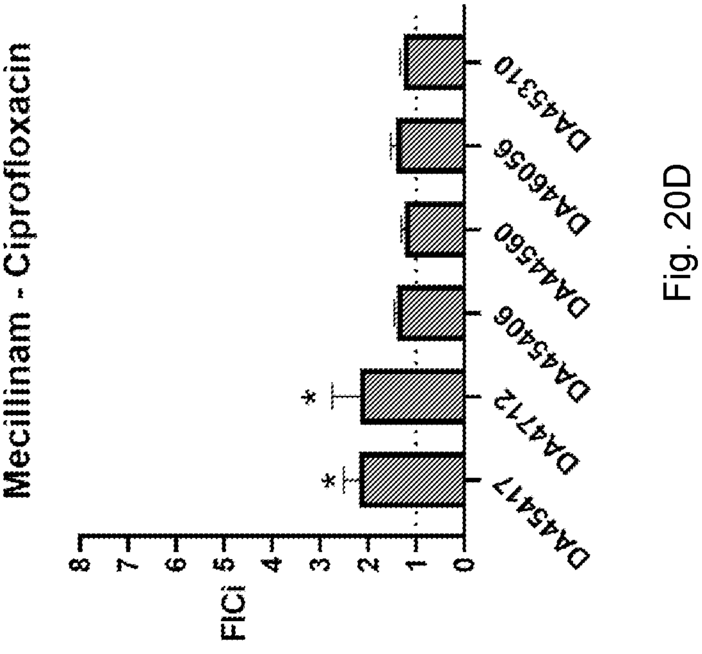
Figures 20F, 20G:
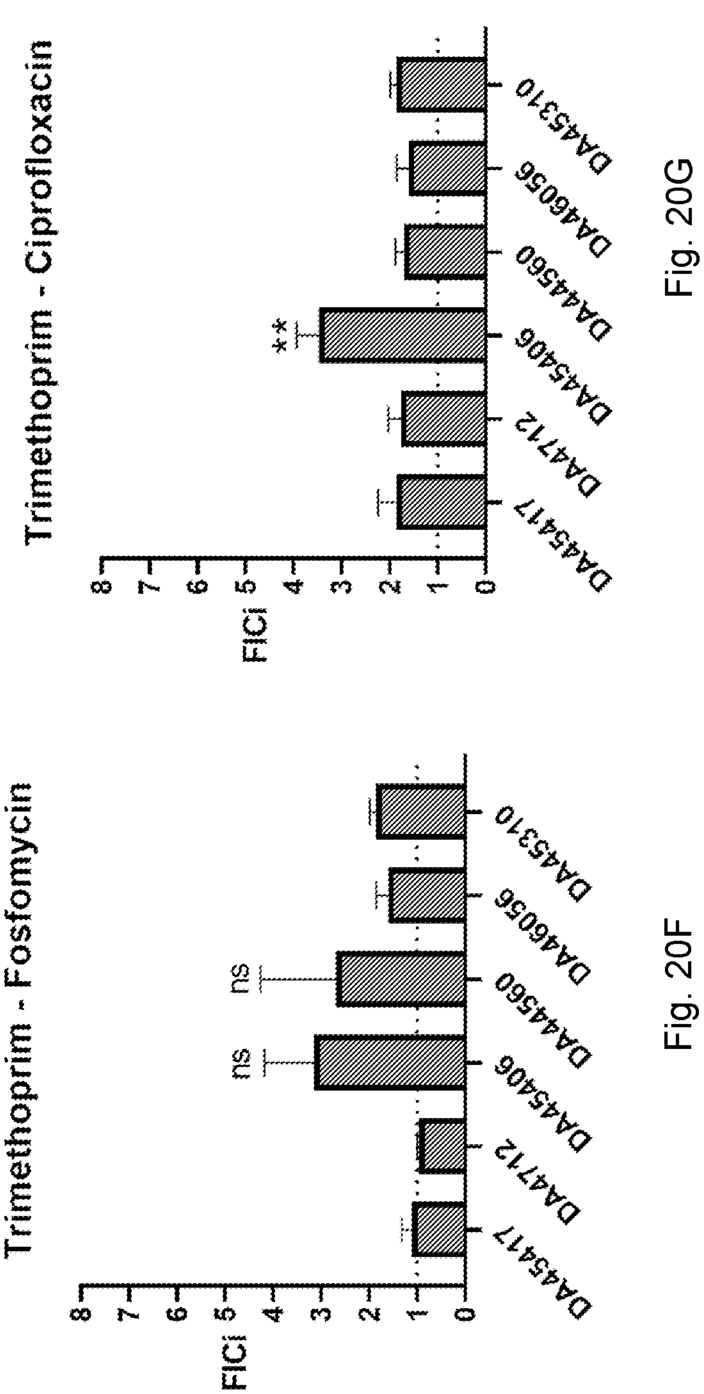
Figure 20I:
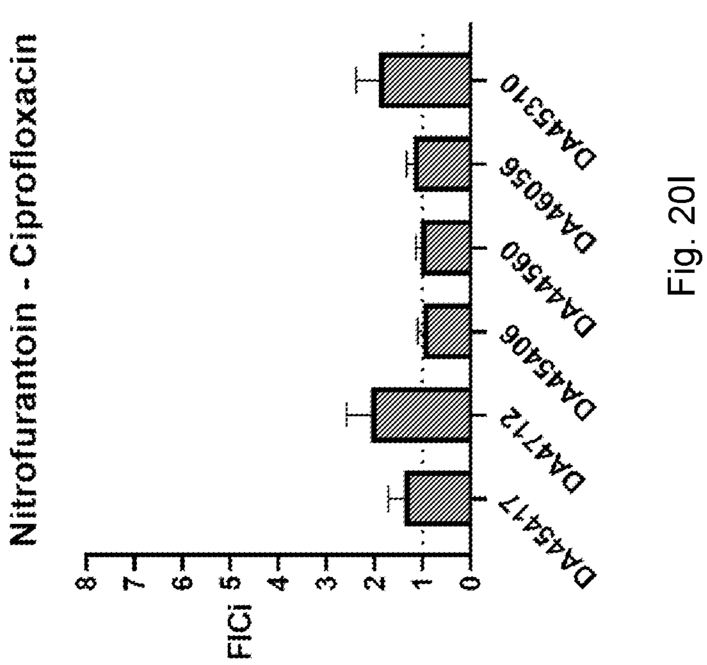
Figure 20H:
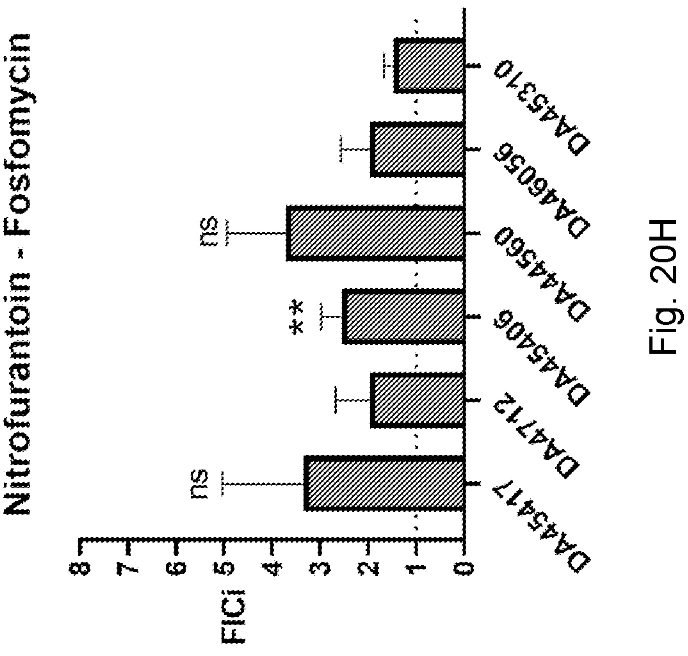
Figure 20J:
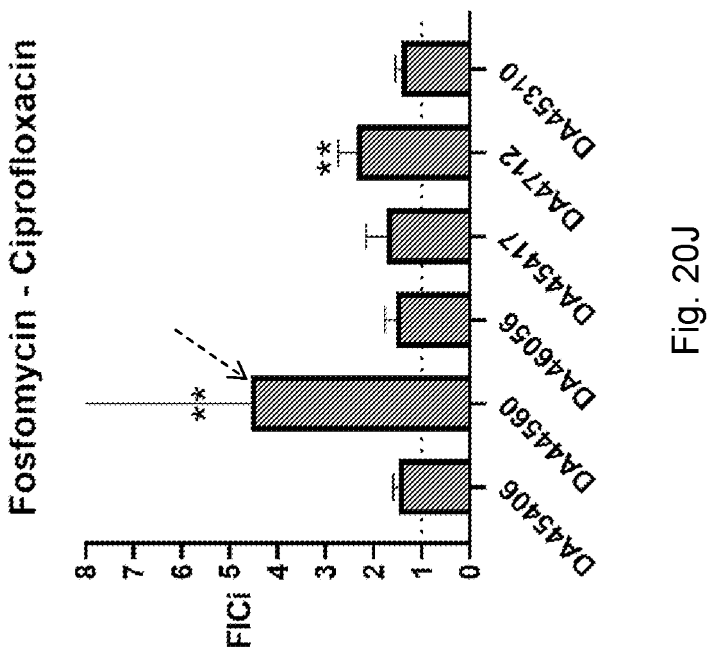
Figure 20K:
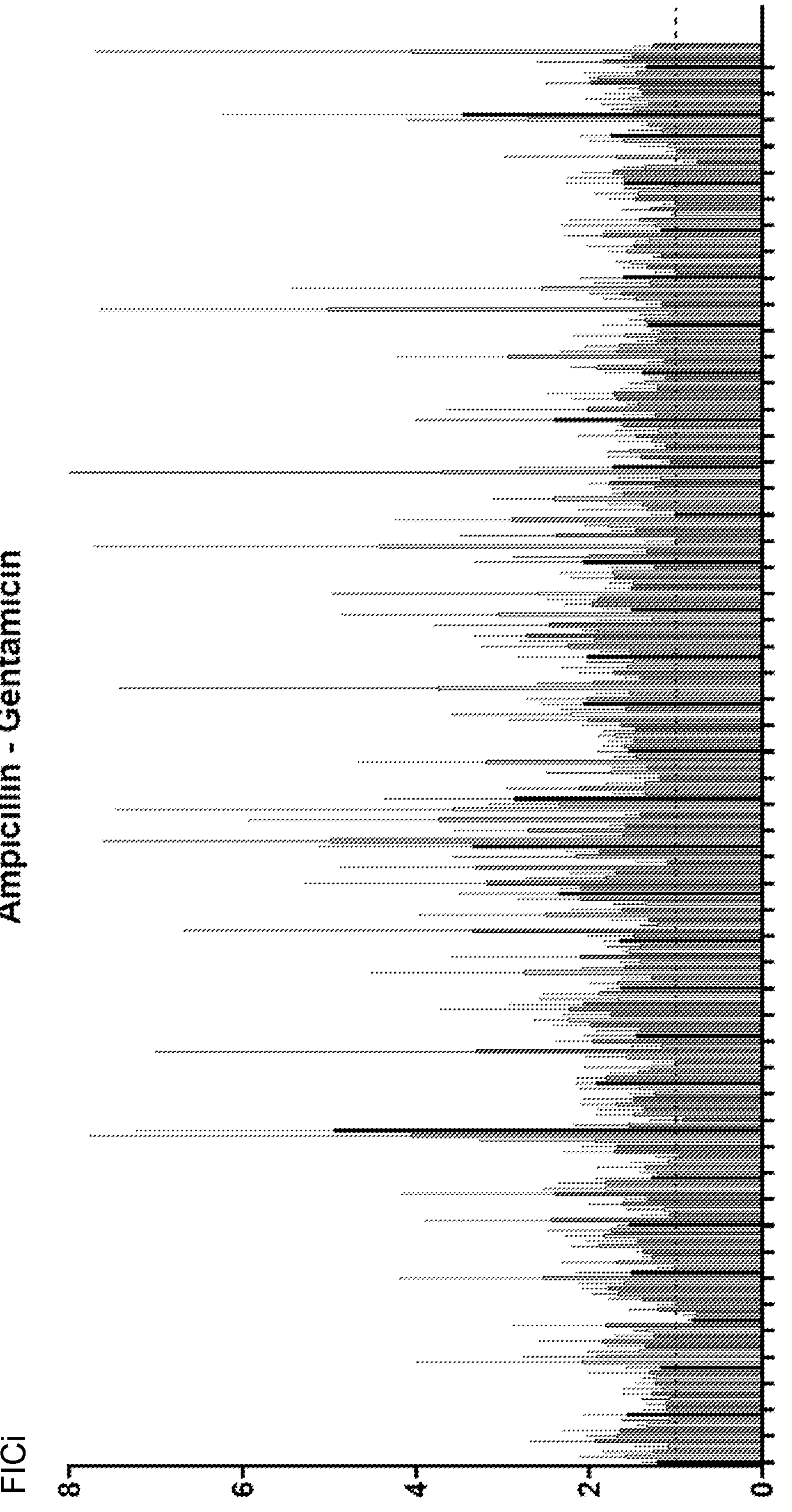
Figure 20L:
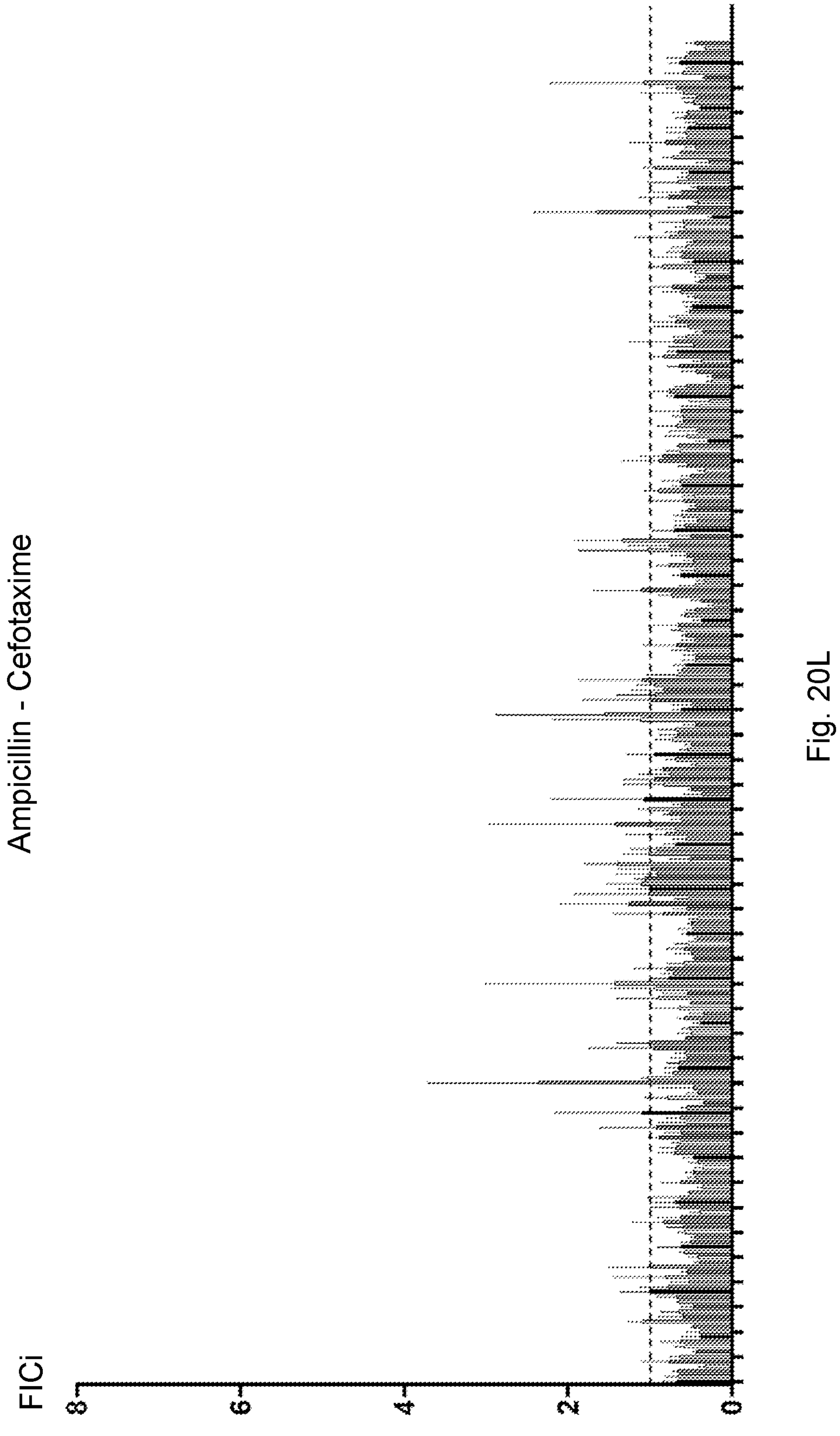
Figure 20M:
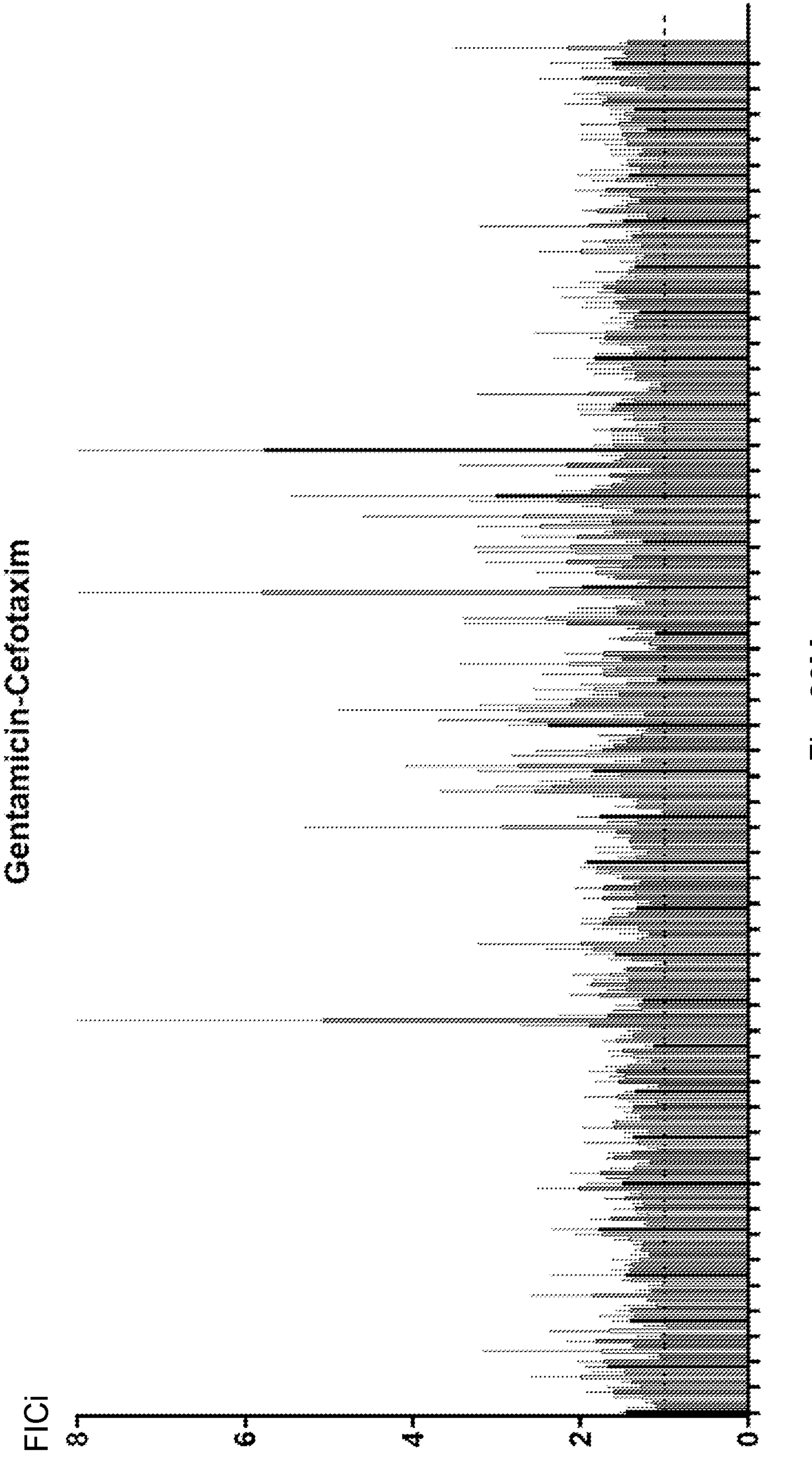

Most combinations were shown to be additive in nature with a few strains where shown varying from that behavior, see Tables 4 and 5, as shown for NIT-CIP (FIG. 20I), MEC-CIP (FIG. 20D), TMP-CIP (FIG. 20G), MEC-FOF (FIG. 20E), TMP-FOF (FIG. 20F), NIT-FOF (FIG. 20H), GEN-CTX (FIG. 20K), and GEN-CTX (FIG. 20M) being additive across all tested strains. FOF-CIP (FIG. 20J) exhibited a borderline but statistically significant antagonistic interaction in isolate DA44560, but additive behavior in all other strains. The medically more interesting results were obtained for the remaining combinations, TMP-NIT (FIG. 20B), MEC-TMP (FIG. 20A), MEC-NIT (FIG. 20C), and AMP-GEN (FIG. 20K). Positive synergy for TMP-NIT (FIG. 20B) and AMP-CTX (FIG. 20L) combinations was detected in the majority of the UTI isolates with a few isolates displayed additive or antagonistic behavior, indicating conserved synergistic interaction nature of these antibiotics with a diverse genetic variation among UTI isolates. The combinations MEC-NIT (FIG. 20C) and on the other hand exhibited a strongly antagonistic behavior that was detected for most of the tested isolates. The combination of MEC-TMP (FIG. 20A) showed a mixture of both positive synergy, strong antagonism and additivity for all of the tested isolates, whilst the combination of AMP-GEN (FIG. 20K) showed a mixture of additivity and different degree of antagonisms. Together these data clearly indicated a value of case-by-case synergy validation within one species.

TABLE 4

| significant effects on bacterial strains | | | | | | |
|---|---|---|---|---|---|---|
| | MEC-TMP | | TMP-NIT | | MEC-NIT | |
| strain | significant synergy | significant antagonism | significant synergy | significant antagonism | significant synergy | significant antagonism |
| DA21682 | | | Y | | | |
| DA24486 | | | Y | | | |
| DA24492 | Y | | | | | |
| DA44023 | | | Y | | | |
| DA44562 | | | Y | | | |
| DA44568 | | | Y | | | Y |
| DA44571 | | | Y | | | Y |
| DA44584 | | | | | | |
| DA45308 | Y | | Y | | | |
| DA45311 | | | Y | | | Y |
| DA45405 | | | Y | | | Y |
| DA45416 | | | Y | | | |
| DA45702 | | | Y | | | |
| DA46004 | | | | | | Y |
| DA46048 | | | | | | Y |

TABLE 4-continued

| significant effects on bacterial strains | | | | | | |
|---|---|---|---|---|---|---|
| | MEC-TMP | | TMP-NIT | | MEC-NIT | |
| strain | significant synergy | significant antagonism | significant synergy | significant antagonism | significant synergy | significant antagonism |
| DA46052 | | | | | | Y |
| DA46055 | | | Y | | | Y |
| DA53052 | | | Y | | | Y |
| DA53250 | | | | | N.A. | N.A. |
| DA56684 | | | Y | | | |
| DA62888 | | | Y | | | |
| DA62890 | | | Y | | | |
| DA62892 | | | | | | |
| DA62894 | | | | | | Y |
| DA62896 | | | Y | | | |
| DA62900 | | | | | | Y |
| DA62902 | | | Y | | | |
| DA62904 | | | Y | | | |
| DA62908 | | | | | | |
| DA62912 | | | Y | | | |
| DA62914 | | | Y | | | Y |
| DA62924 | | | | | | Y |
| DA62932 | | | Y | | | |
| DA62936 | | | | | | |
| DA62938 | | | | | | Y |
| DA62940 | | | Y | | | Y |
| DA62942 | | | Y | | | |
| DA62944 | | | | | | |
| DA62946 | Y | | Y | | | |
| DA62948 | Y | | | | | Y |
| DA62950 | | | Y | | | |
| DA62960 | | | Y | | | |
| DA62964 | | | Y | | | |
| DA62966 | | | Y | | | |
| DA62968 | | | Y | | | |
| DA62972 | | | Y | | | Y |
| DA62974 | | | | | | Y |
| DA62976 | | | Y | | | |
| DA62978 | | | Y | | | |
| DA62980 | Y | | Y | | | Y |
| DA62982 | | | Y | | | Y |
| DA62986 | | | Y | | | |
| DA62992 | | | | | | |
| DA62996 | | | Y | | | |
| DA63004 | Y | | Y | | | |
| DA63006 | | | | | | |
| DA63010 | | | | | | Y |
| DA63014 | | | Y | | | |
| DA63016 | | | | | | |
| DA63018 | | | | | | Y |
| DA63022 | | | Y | | | |
| DA63024 | | | Y | | | Y |
| DA63028 | | | Y | | | |
| DA63032 | | | | | | |
| DA63036 | | | Y | | | |
| DA63040 | | | Y | | | |
| DA63042 | | | Y | | | Y |
| DA63044 | | | | | | |
| DA63050 | | | | | | |
| DA63056 | | | | | | Y |
| DA63060 | | | Y | | | |
| DA63062 | | | | | | Y |
| DA63064 | | | Y | | | |
| DA63066 | | | Y | | | |
| DA63068 | | | | | | |
| DA63070 | | | | | | |
| DA63072 | | | | | | |
| DA63074 | | | Y | | | Y |
| DA63078 | | | Y | | | Y |
| DA63080 | Y | | Y | | | |
| DA63084 | | | Y | | | Y |
| DA63086 | | | Y | | | Y |
| DA63090 | | Y | Y | | | Y |
| DA63092 | | | | | | Y |
| DA63094 | | Y | Y | | | Y |
| DA63096 | | Y | Y | | | Y |
| DA63100 | | | | | | |
| DA63102 | | | | | | Y |

TABLE 4-continued

| significant effects on bacterial strains | | | | | | |
|---|---|---|---|---|---|---|
| | MEC-TMP | | TMP-NIT | | MEC-NIT | |
| strain | significant synergy | significant antagonism | significant synergy | significant antagonism | significant synergy | significant antagonism |
| DA63106 | | | Y | | | |
| DA63108 | | | | | | |
| DA63110 | | | Y | | | Y |
| DA63112 | | | | | | |
| DA63116 | | | | | | |
| DA63118 | | | | | | Y |
| DA63128 | | | | | | Y |
| DA63130 | | | Y | | | |
| DA63138 | | | | | | |
| DA63142 | | | Y | | | |
| DA63144 | | | Y | | | |
| DA63150 | | | | | | |
| DA63152 | | | | | | |
| DA63154 | | | Y | | | |
| DA63156 | | Y | Y | | | Y |
| DA63158 | | | | | | |
| DA63162 | | | | | | |
| DA63166 | | | Y | | | Y |
| DA63168 | | | Y | | | |
| DA63170 | | | Y | | | Y |
| DA63174 | | | | | | |
| DA63180 | | | | | | Y |
| DA63184 | | | | | | |
| DA63188 | | | Y | | | Y |
| DA63190 | | Y | Y | | | Y |
| DA63192 | | | | | | |
| DA63200 | Y | | | | | Y |
| DA63202 | | | | | | |
| DA63204 | | | Y | | | Y |
| DA63212 | | | Y | | | |

N.A.-not applicable
Y-yes

TABLE 5

| significant effects on bacterial strains | | | | | | |
|---|---|---|---|---|---|---|
| | AMP-GEN | | AMP-CTX | | GEN-CX | |
| strain | significant synergy | significant antagonism | significant synergy | significant antagonism | significant synergy | significant antagonism |
| DA24486 | | | | | | |
| DA44023 | | | | | | |
| DA44562 | | | | | | |
| DA44568 | | | | | | |
| DA44571 | | | | | | |
| DA44573 | | | Y | | | |
| DA44578 | | | Y | | | |
| DA45308 | | | | | | |
| DA45311 | | | | | | |
| DA45314 | | | | | | |
| DA45405 | | | | | | |
| DA45416 | | | | | | |
| DA45702 | | | | | | |
| DA46048 | | | | | | |
| DA46052 | | | | | | |
| DA46055 | | | | | | |
| DA62888 | | | | | | |
| DA62890 | | | | | | |
| DA62894 | | | | | | |
| DA62896 | | | | | | |
| DA62898 | | | Y | | | |
| DA62900 | | | | | | |
| DA62904 | | | | | | |
| DA62908 | | | | | | |
| DA62912 | | | | | | |
| DA62914 | | | | | | |
| DA62924 | | | | | | |
| DA62932 | | | | | | |

TABLE 5-continued

| significant effects on bacterial strains | | | | | | |
|---|---|---|---|---|---|---|
| | AMP-GEN | | AMP-CTX | | GEN-CX | |
| strain | significant synergy | significant antagonism | significant synergy | significant antagonism | significant synergy | significant antagonism |
| DA62936 | | | | | | |
| DA62938 | | | | | | |
| DA62940 | | | | | | |
| DA62942 | | | | | | |
| DA62944 | | | | | | |
| DA62952 | | | | | | |
| DA62960 | | | | | | |
| DA62962 | | | | | | |
| DA62964 | | | | | | |
| DA62966 | | | | | | |
| DA62968 | | | | | | |
| DA62972 | | | | | | |
| DA62974 | | | | | | |
| DA62976 | | | | | | |
| DA62980 | | | | | | |
| DA62982 | | | | | | |
| DA62986 | | | | | | |
| DA62990 | | | | | | |
| DA62992 | | | | | | |
| DA62996 | | | | | | |
| DA63000 | | | | | | |
| DA63006 | | | | | | |
| DA63010 | | | | | | |
| DA63014 | | | | | | |
| DA63016 | | | | | | |
| DA63018 | | | Y | | | |
| DA63022 | | | | | | |
| DA63024 | | | | | | |
| DA63028 | | | | | | |
| DA63036 | | | Y | | | |
| DA63042 | | | | | | |
| DA63044 | | | | | | |
| DA63050 | | | | | | |
| DA63056 | | | | | | |
| DA63062 | | | | | | |
| DA63066 | | | | | | |
| DA63068 | | | | | | |
| DA63074 | | | | | | |
| DA63078 | | | | | | |
| DA63080 | | | | | | |
| DA63088 | | | | | | |
| DA63090 | | | | | | |
| DA63092 | | | Y | | | |
| DA63094 | | | | | | |
| DA63096 | | | | | | |
| DA63100 | | | | | | |
| DA63102 | | | | | | |
| DA63108 | | | | | | |
| DA63110 | | | | | | |
| DA63118 | | | | | | |
| DA63124 | | | | | | |
| DA63128 | | | | | | |
| DA63134 | | | | | | |
| DA63148 | | | | | | |
| DA63154 | | | | | | |
| DA63156 | | | | | | |
| DA63162 | | | | | | |
| DA63166 | | | | | | |
| DA63168 | | | | | | |
| DA63170 | | | | | | |
| DA63174 | | | Y | | | |
| DA63176 | | | | | | |
| DA63184 | | | | | | |
| DA63188 | | | | | | |
| DA63190 | | | | | | |
| DA63192 | | Y | | | | Y |
| DA63196 | | | | | | |
| DA63200 | | | | | | |
| DA63204 | | | | | | |
| DA63208 | | | | | | |
| DA63216 | | | | | | |
| DA63220 | | | | | | |
| DA63222 | | | | | | |

TABLE 5-continued significant effects on bacterial strains

| strain | AMP-GEN | | AMP-CTX | | GEN-CX | |
|---|---|---|---|---|---|---|
| | significant synergy | significant antagonism | significant synergy | significant antagonism | significant synergy | significant antagonism |
| DA63224 | | | | | | |
| DA63228 | | | | | | |
| DA63230 | | | | | | |
| DA63232 | | | | | | |
| DA63234 | | | | | | |
| DA63236 | | | | | | |
| DA63240 | | | | | | |
| DA63242 | | | | | | |
| DA63246 | | | | | | |
| DA63258 | | | | | | |
| DA63268 | | | | | | |
| DA63278 | | | | | | |
| DA63282 | | | | | | |
| DA63286 | | | | | | |
| DA63288 | | | | | | |
| DA63290 | | | | | | |
| DA63294 | | | | | | |
| DA63300 | | | | | | |
| DA63304 | | | | | | |
| DA63310 | | | | | | |
| DA63312 | | | | | | |
| DA63314 | | | | | | |
| DA63316 | | | | | | |
| DA63318 | | | | | | |
| DA63324 | | | | | | |
| DA63326 | | | | | | |
| DA63328 | | | | | | |
| DA63338 | | | | | | |
| DA63344 | | | | | | |
| DA63348 | | | | | | |
| DA63356 | | | | | | |
| DA63372 | | | Y | | | |
| DA63376 | | | | | | |
| DA63378 | | | | | | |
| DA63380 | | | | | | |
| DA63568 | | | | | | |
| DA63572 | | | | | | |
| DA63582 | | | | | | |
| DA63584 | | | | | | |
| DA63586 | | | | | | |
| DA63592 | | | | | | |
| DA63598 | | | | | | |
| DA63600 | | | | | | |
| DA63602 | | | | | | |
| DA63606 | | | | | | |
| DA63610 | | | | | | |
| DA63612 | | | | | | |
| DA63614 | | Y | | | | |
| DA63616 | | | | | | |
| DA63618 | | | | | | |
| DA63620 | | | | | | |
| DA63622 | | | | | | |
| DA63626 | | | | | | |
| DA63628 | | | | | | |
| DA63632 | | | | | | |
| DA63636 | | | | | | |
| DA63640 | | | | | | |
| DA63642 | | | | | | |
| DA63644 | | | | | | |
| DA63646 | | | | | | |
| DA63658 | | | | | | |
| DA63662 | | | | | | |
| DA63664 | | | | | | |
| DA63668 | | | | | | |
| DA63670 | | | | | | |
| DA63678 | | | | | | |
| DA63682 | | | | | | |
| DA63684 | | | Y | | | |
| DA63686 | | | | | | |
| DA63692 | | | | | | |
| DA63696 | | | | | | |
| DA63704 | | | Y | | | |
| DA63710 | | | Y | | | |

TABLE 5-continued

| significant effects on bacterial strains | | | | | | |
|---|---|---|---|---|---|---|
| | AMP-GEN | | AMP-CTX | | GEN-CX | |
| strain | significant synergy | significant antagonism | significant synergy | significant antagonism | significant synergy | significant antagonism |
| DA63714 | | | | | | |
| DA63716 | | | | | | |
| DA63718 | | | | | | Y |
| DA63720 | | | Y | | | |
| DA63722 | | | | | | |
| DA63728 | | | | | | |
| DA63730 | | | | | | |
| DA63732 | | | | | | |
| DA63734 | | | | | | |
| DA63736 | | | | | | |
| DA63738 | | | | | | |
| DA63740 | | | | | | |
| DA63742 | | | | | | |
| DA63746 | | | | | | |
| DA63750 | | | | | | |
| DA63756 | | | | | | |
| DA63762 | | | | | | |
| DA63770 | | | | | | |
| DA63778 | | | | | | |
| DA63782 | | | | | | |
| DA63786 | | | | | | |
| DA63792 | | | | | | |
| DA63796 | | | | | | |
| DA63800 | | | | | | |
| DA63802 | | | Y | | | |
| DA63804 | | | | | | |
| DA63806 | | | | | | |
| DA63808 | | | | | | |
| DA63810 | | | | | | |
| DA63818 | | | | | | |
| DA63820 | | | | | | |
| DA63824 | | Y | | | | Y |
| DA63830 | | | Y | | | |
| DA63832 | | | | | | |
| DA63836 | | | | | | |
| DA63838 | | | | | | |
| DA63846 | | | Y | | | |
| DA63854 | | | Y | | | |
| DA63856 | | | | | | |
| DA63858 | | | | | | |
| DA63866 | | | Y | | | |
| DA63868 | | | | | | |
| DA63874 | | | | | | |
| DA63876 | | | | | | |
| DA63878 | | | | | | |
| DA63880 | | | | | | |
| DA63886 | | | Y | | | |
| DA63894 | | | | | | |
| DA63898 | | | | | | |
| DA63902 | | | | | | |
| DA63904 | | | | | | |
| DA63906 | | | | | | |
| DA63908 | | | Y | | | |
| DA63918 | | | | | | |
| DA63920 | | | | | | |
| DA63928 | | | | | | |
| DA63930 | | | | | | |
| DA63938 | | | Y | | | |
| DA63942 | | | | | | |
| DA63944 | | | | | | |
| DA63952 | | | | | | |
| DA63956 | | | | | | |
| DA63960 | | | | | | |
| DA63966 | | | | | | |
| DA63968 | | | | | | |
| DA63970 | | | | | | |
| DA63972 | | | | | | |
| DA63974 | | | | | | |
| DA63976 | | | | | | |
| DA63978 | | | Y | | | |
| DA63980 | | Y | | | | |
| DA63982 | | | | | | |
| DA63984 | | | | | | |

TABLE 5-continued

| significant effects on bacterial strains | | | | | | |
|---|---|---|---|---|---|---|
| | AMP-GEN | | AMP-CTX | | GEN-CX | |
| strain | significant synergy | significant antagonism | significant synergy | significant antagonism | significant synergy | significant antagonism |
| DA63990 | | | | | | |
| DA63992 | | | | | | |
| DA63996 | | | | | | |
| DA63998 | | | | | | |
| DA64008 | | | | | | |
| DA64010 | | | | | | |
| DA64014 | | | | | | |
| DA64018 | | | Y | | | |
| DA64020 | | | | | | |
| DA64028 | | | Y | | | |
| DA64032 | | | | | | |
| DA64036 | | | | | | |
| DA64040 | | | | | | |
| DA64042 | | | | | | |
| DA64044 | | | | | | |
| DA64048 | | | Y | | | |
| DA64050 | | | | | | |
| DA64052 | | | | | | |
| DA64054 | | | | | | |
| DA64056 | | | | | | |
| DA64060 | | | | | | |
| DA64062 | | | Y | | | |
| DA64066 | | | | | | |

DISCUSSION

In this study, we presented and characterized the CombiANT™ assay, which enabled an efficient determination of antibiotic interactions. The extensive technical validation indicated high accuracy and precision, and an overall equal performance to the established checkerboard method. We then implemented CombiANT™ for a screen of antibiotic synergy among a large collection of clinical UTI isolates. A consistent synergy, neutral and antagonistic interaction was discovered with significant strain-to-strain variation.

The CombiANT™ protocol was specifically designed for simplicity and clinical implementation. In the inactive state, it can be stored refrigerated, in large amounts, according to the regular shelf-life of antibiotic agar plates. That makes it feasible for hospitals and laboratories to pre-load culture container inserts with antibiotics of interest and then quickly implement them when needed. Starting with the activation step, the handling of CombiANT™ plates is identical to that of regular agar plates and, thus, compatible with the existing clinical pipelines for the mass-handling of agar plates, including automated pouring of agar for large-scale production.

To allow for the easiest use of CombiANT™ both by clinics and by academic labs, we designed two different protocols, a resistance breakpoint-based protocol for clinical use (Table 2 and Table 3, and as applied for the UTI screen in FIGS. 20A to 20M), and a higher-sensitivity MIC-based protocol for research applications (Table 1, as applied for FIGS. 18A to 18D). The analysis of CombiANT™ can be fully automated, and merely requires a digital picture as input. The non-requirement of dedicated machinery makes CombiANT™ suitable also for low-resource environments.

An important design principle of CombiANT™ was that antibiotic synergy is quantified at high, clinically relevant, concentrations. Synergy is measured from the edge of inhibition zones, meaning the MIC-equipotency line of combination space, using the FICi. Other methods, such as those based on growth rates, measure synergy at lower inhibition levels. In these experiments, synergy is measured at medium inhibition ranges by deviation from an additive model (Bliss independence or Loewe additivity). It has been shown that interaction profile of a particular antibiotic combination can be dose-dependent, occasionally complicating synergy quantification from checkerboards. These biologically interesting cases indicate complex physiological effects. Synergy measurements by FICi are robust (or blind) to such variation, as they are performed at a set high inhibition level (MIC), which is more clinically relevant. Another technical difference of the plate-based CombiANT™ assay compared to broth microdilution methods refers to the phenotypic effects of antibiotics on cell shape. Many antibiotics induce changes in cell shape, as part of their mechanism of action. For example, beta-lactam antibiotics induce extensive cell elongation prior to cell death. Such elongation can lead to an overestimation of viable cell numbers by optical density measurements, leading for example to a disagreement of MIC values called by broth and agar methods.

The results obtained in the technical dataset agree with those in the literature. CombiANT™ replicated the previously reported synergies between AMP-GEN, TMP-MEC, and TMP-NIT; the strong antagonism between MEC-NIT, and additivity between beta-lactams and CIP in *E. coli* K12-MG1655. However, the additive combination GEN-CIP was previously classified as synergistic using the low-inhibition growth rate methodology. Only few antibiotic interactions in *P. aeruginosa* PA14 strain and the *S. aureus* ATCC29213 were previously characterized, limiting comparisons. AMP-CIP additivity was previously reported for *S. aureus*, and interactions of CIP with beta-lactams and the aminoglycoside GEN are known to be antagonistic in *P. aeruginosa*. CombiANT™ replicated these observations. In conclusion, the observed high agreement of our measurements with the literature supports the accuracy and utility of CombiANT™.

As the above synergy screening of clinical UTI isolates iterates, there are cases, such as the interaction between TMP-MEC were combining two antibiotics seems to have a consistent antagonistic effect across most strains. Cases such as these, with antagonistic behavior across the board, illustrate the need for clear guidance when designing combination therapies, even empirically. Identifying such combinations of antibiotics that should be avoided, will require large scale systematic synergy screenings. With the current methods that quantify antibiotic synergy, a systematic screening of such a scale is unfeasible. However, CombiANT™ presents a new, less labor-costly method, that is still capable of quantifiable results. Using our new approach to interaction studies, makes such large-scale synergy screens attainable.

The screening for the interactions between TMP-NIT, TMP-MEC, MEC-NIT, AMP-GEN, AMP-CTX, and GEN-CTX revealed an important result, namely that the same two antibiotics might not have a consistent synergy profile across different isolates of the same species. If antibiotics can be synergistic against one strain but additive or antagonistic for another, then synergy screens should become a part of standard testing in microbiology labs. Such behavior illustrates further, the need for an assay, such as CombiANT™. An assay that is quantitative, but simple enough so as not to be reserved for difficult or chronic cases, but to be part of the standard screening, all cases receive in a microbiology lab.

Aside from the clinical applicability, CombiANT™ has high potential as a tool for basic research in biology. A mechanistic understanding of most antibiotic interactions is currently lacking. The research field is also far from an evolutionary understanding of antibiotic interactions or antibiotic interactions with other bioactive compounds. These knowledge gaps may partly be explained by the complexity of current synergy measurement methods. In the screen of UTI isolates the majority of antibiotic interactions were additive. The variable synergy profiles that were observed with MEC-TMP and AMP-GEN, indicated interesting biological strain-to-strain variation. Furthermore, the highly-antagonistic interaction between MEC-NIT may potentially indicate an evolutionary conservation of this drug interaction, implying a functional constraint between cellular functional modules. The antagonism could potentially be explained by an overlap in the cellular drug and stress responses to the component drugs. It has been shown that both beta-lactams and NIT individually induce expression of the cellular SOS response for DNA repair, potentially explaining the antagonism through a coordinated stronger defense response. Yet, the antibiotics also induce other response systems, i.e., the RpoS-mediated stress response for beta-lactams, and oxidative stress response in the case of NIT. The antagonism could therefore alternatively be explained by potential pleiotropy of these further responses. Altogether different explanations are reduced antibiotic uptake mechanisms, or increased detoxification. These and other hypotheses could be efficiently tested by implementing CombiANT™ for a functional genetics screen.

Example 2—Calibration Protocol

For every antibiotic tested, a suitable reference strain is selected. In this Example all calibrations were performed with *E. coli* strain K12-MG1665. Below are the steps of the calibration protocol:

1. MIC of the antibiotic against the reference strain is determined using a broth microdilution assay (BMD), unless already known.
2. A CombiANT™ assay is prepared in triplicate. The three agent reservoirs are loaded with 10×MIC, 20×MIC and 40×MIC antibiotic concentrations in MH agar.
3. Following the protocol of the CombiANT™ assay, a final layer of agar is poured on the three culture container inserts and after it solidifies, a population of the reference strain is inoculated according to the protocol.
4. After 24 hours, inhibition zones are formed on the outside of the insert as shown on FIG. 9.

The edge of the concentration zones on the outside of the culture container inserts, corresponds to the MIC of the antibiotic in use against the strain. The FEM concertation model's diffusion coefficient, is tuned iteratively until the predicted concentration at the edge of all three inhibition zones matches the experimental value determined by the BMD. Once the tuning of the diffusion coefficient is complete, the model is tested against the two remaining replicates of the tuning assay. If variability in the MIC prediction is less than 10% of the experimental one for both remaining assays, then the calibration is completed. Following the diffusion model calibration, that antibiotic can be used in all experimental assays. The recommended initial antibiotic concentration is calculated as the concentration that would result in an inhibition zone greater than 5 mm, to avoid calculation artifacts.

Example 3—Protocol for CombiANT™ Assay

1. Outside the use pipeline: Prepare the CombiANT™ culture container inserts.
   a. Put a CombiANT™ culture container insert in a sterile petri dish;
   b. Consult Table 1 (MIC-based high-resolution determination) or Table 2 or 3 (breakpoint based determination) for input antibiotic concentrations;
   c. Dilute antibiotic to input concentration in liquid autoclaved MH agar (temperature 50-65° C.);
   d. Add 0.5 ml of antibiotic agar to assigned agent reservoir of the CombiANT™ culture container insert;
   e. Add Petri dish lid and refrigerate on a level surface to allow setting of the agar. At 4° C., the loaded culture container inserts are stable for at least one week.
2. Before use: Grow a dense overnight culture of target strain from a single colony in MH broth.
3. In use: Activate CombiANT™ culture container inserts by overcasting with MH agar. For a standard 90 mm Petri dish, add 25 ml of MH agar.
4. Let the agar set for at least 3 h at room temperature.
5. Dilute the dense bacterial culture to 0.5 McFarland.
6. Using a sterile cotton swan, inoculate plate surface with bacteria to obtain lawn growth, in accordance with EUCAST guidelines for disk diffusion tests v8.0.
7. Incubate plates for 24 h.
8. Take a picture of the plate and identify the CP and IC points.
9. Input the data into the analysis algorithm.

Example 4—CombiANT™ Different Bioactive Compounds

In this example, we extended the utility of the CombiANT™ assay with different bioactive compounds on four different bacterial species.

Materials and Methods

Strains and Media

The strains *Escherichia coli* K12-MG1655 (Eco), *Pseudomonas aeruginosa* PA14 (Pae), *Staphylococcus*

*aureus* ATCC29213 (Sau) and *Vibrio natriegens* ATCC14048 (Vna) were used against four bioactive compounds: aspirin (ASP), benzoic acid (BA), ibuprofen (IBU), and tea tree oil (TTO). Bacteria were cultured on Mueller Hinton agar and in Mueller Hinton broth (Becton Dickinson, Sparks, MD; Refs. 275730, 225250) with incubations at 37° C. overnight. Overnight cultures were prepared from single colonies in 1 ml and 190 rpm orbital shaking. For *Vibrio natriegens*, culture media was supplemented with v2 salts comprising of 204 mM NaCl, 4.2 mM KCl, and 23.14 mM $MgCl_2$ [10]. Bioactive compound stocks were prepared according to manufacturer's recommendations and stored at −20° C. in aliquots for single use: aspirin 400 mg/ml in 50% DMSO (Sigma-Aldrich, Ref. A2093-100G), benzoic acid 400 mg/ml in DMSO (Sigma-Aldrich, Ref. 242381-25G), and ibuprofen 664 mg/ml in water (Sigma, Ref. 11892-100G). Tea tree oil was stored at room temperature as the 100% oil received from the manufacturer until required (Sigma-Aldrich, Ref. W390208-SAMPLE-K).

Broth Microdilution

The MIC values for the bioactive compounds were determined individually, using standard broth microdilution methodology in agreement with EUCAST guidelines. Two-fold serial dilutions of each bioactive compound in Mueller Hinton broth for Eco, Pae and Sau strains were prepared in 96-well microtiter plates. The plates were then inoculated with approximately $3\times10^5$ cells from a dense overnight culture (1:1000 dilution, 180 μl final volume), sealed and incubated without shaking at 37° C. for 24 h. MIC was called at the lowest concentration that yielded a visual growth signal of non-inoculated control wells. Measurements were performed with three biological replicates and their average was designated MIC. For determination of MIC of the Vna strain, the media was supplemented with v2 salts which is required for the growth of this bacterial species.

Input Concentrations

To determine self-interaction using the CombiANT™ assay, the insert concentrations were determined based on the MIC of the bioactive compound against the four strains used (Table 6).

TABLE 6 bioactive compound input concentrations

| Compound | Abbreviation | Insert concentrations | Species |
|---|---|---|---|
| Aspirin | ASP | 6, 12, 24 mg/ml | Eco, Pae, Sau |
| Aspirin | ASP | 12, 24, 36 mg/ml | Vna |
| Benzoic Acid | BA | 15, 30, 45 mg/ml | Eco, Pae, Sau |
| Benzoic Acid | BA | 3.75, 7.5, 15 mg/ml | Vna |
| Ibuprofen | IBU | 250, 325, 375 mg/ml | Eco |
| Ibuprofen | IBU | 150, 250, 500 mg/ml | Pae |
| Ibuprofen | IBU | 10.5, 17.5, 35 mg/ml | Sau |
| Ibuprofen | IBU | 57, 95, 190 mg/ml | Vna |
| Tea tree oil | TTO | 24, 27, 30% | Eco |
| Tea tree oil | TTO | 19, 28.5, 47.5% | Pae |
| Tea tree oil | TTO | 13, 19.5, 26% | Sau |
| Tea tree oil | TTO | 12, 18, 30% | Vna |

Results and Discussion

Figure 21:
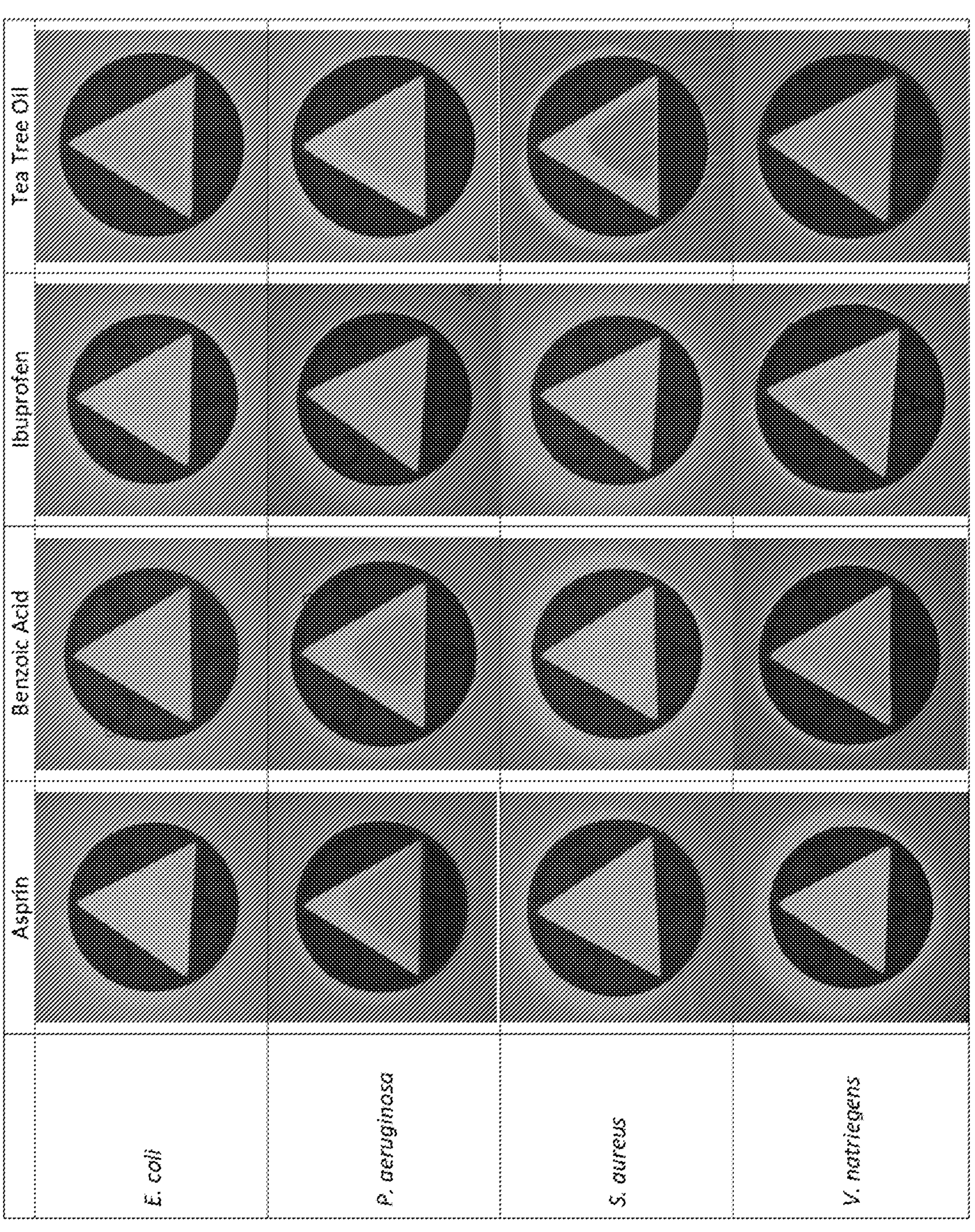
FIG. 21 illustrates the usage of CombiANT™ for the analysis of bioactive compounds other than antibiotics.

This Example demonstrated that CombiANT™ also can be used to evaluate bioactive compounds besides antibiotics (FIG. 21). These compounds readily diffuse within the agar growth medium. Increasing concentrations of the compounds were placed in the inserts resulting in observed differences in inhibition zone sizes, which can be quantified as discussed previously for FIGS. 9-10.

Thus, CombiANT™ is not restricted to the study of drug interactions between antibiotics. In principle, the individual and combined activity of any bioactive compound can be studied with CombiANT™. CombiANT™ may therefore be used to, for example, study the effects of chemotherapeutic compounds on cells such as human and animal cells, and also be used for applications in environmental microbiology. A potential diversity of applications is supported by the high flexibility of CombiANT™, which can be easily implemented with different culture media and different culturing conditions (such as running CombiANT™ at different temperatures). CombiANT™ could also be applied to characterize biological activities, in dependence of several inducers and repressors, provided the activity can be optically tracked, e.g., fluorescence, colorimetry, etc. The spread of antibiotic resistance increasingly makes combination therapy attractive, but high pathogen diversity indicates an added value of personalized treatment, which optimally requires validation and optimization of treatment based on results from the CombiANT™ assay. CombiANT™ may facilitate the identification of combination treatment possibilities for isolates that (by other analysis methods) appear broadly resistant.

Example 5—CombiANT™ Mixed Bacterial Samples

In this example, we extended the utility of the CombiANT™ assay to handle mixed bacterial samples and to extrapolate two different sets of FICi within one test when the two component bacteria are differentiated by distinct fluorescent markers.

Materials and Methods

Strains and Media

The strains MP026 and TB191 are both derivatives of the *Escherichia coli* K12-MG1655 strain. MP026 has been genetically engineered to express a red fluorescent protein (encoded by the mCherry gene). This strain is susceptible to the antibiotic chloramphenicol. The strain MP026 was a kind gift from Dr. Maroš Pleška (Rockefeller University, USA). TB191 has been genetically engineered to express a cyan fluorescent protein (encoded by the cerulean gene) and resistance to the antibiotic chloramphenicol (encoded by the cat gene). TB191 was a kind gift from Dr. Tobias Bergmiller (University of Exeter, U.K.). Bacteria were cultured on Mueller Hinton agar and in Mueller Hinton broth (Becton Dickinson, Sparks, MD; Refs. 275730, 225250) with incubations at 37° C. overnight. Overnight cultures were prepared from single colonies in 1 ml and 190 rpm orbital shaking. Antibiotic stocks were prepared according to manufacturer's recommendations and stored at −20° C. in aliquots for single use: NIT 10 mg/ml in DMSO (Sigma, Ref. N7878-10G), and TMP 10 mg/ml in DMSO (Sigma, Ref. T-7883-5G); CAM 12.5 mg/mL in Ethanol (Sigma, Ref. C0378-5G).

Mixture Test

Diluted overnight cultures of each of MP026 and TB191 strains were used as the inoculum to apply to the CombiANT™ assay as previously described in Example 1. A mixture with a 1:1 ratio of MP026 and TB191 strains was prepared from overnight cultures. The total density of the overnight culture was $2\times10^8$ cfu/mL. This mixture was then used as the inoculum to apply to the CombiANT™ assay as previously described in Example 1. The antibiotic insert concentrations were determined based on the MIC of the MP026 strain against the three antibiotics used (Table 7).

TABLE 7 antibiotic input concentrations for mixture study

| Compound | Abbreviation | Insert concentrations |
|---|---|---|
| Chloramphenicol | CAM | 40 mg/L |
| Nitrofurantoin | NIT | 80 mg/L |
| Trimethoprim | TMP | 3.2 mg/L |

Results and Discussion

Figure 22:
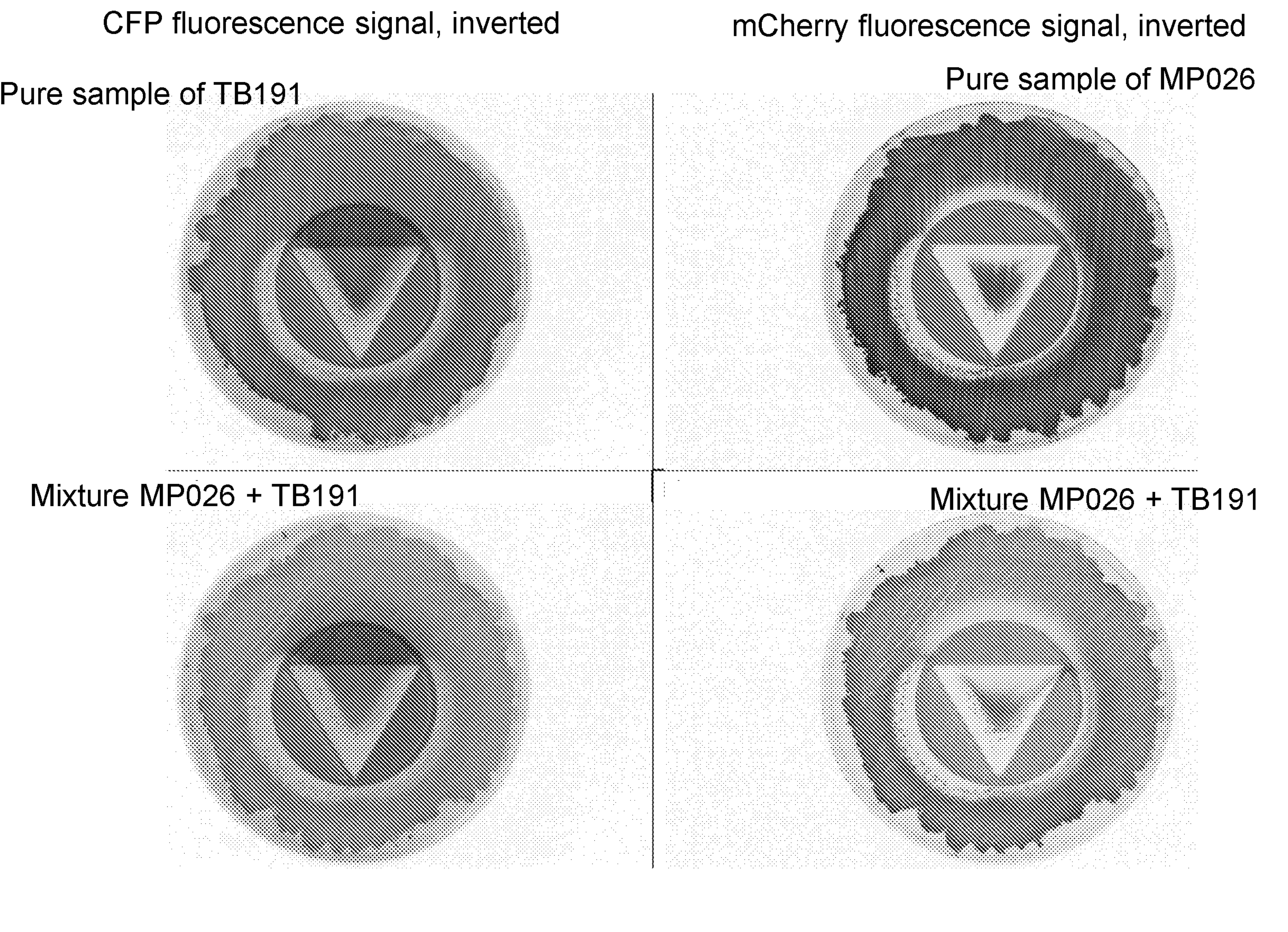
FIG. 22 illustrates usage of CombiANT™ for the analysis of mixed bacterial samples expressing different fluorescent proteins.

We demonstrated that CombiANT™ can be utilized with samples of mixed bacteria. When the component bacteria of the mixture can be differentiated by fluorescence (FIG. 22) or color, their individual FICi values can be determined in a single CombiANT™ assay. Table 8 shows FICi values for MP026 and TB191.

TABLE 8

FICis from mixture of bacteria applied in one CombiANT assay

| Component strain in 1:1 mixture | Compounds used | FICi of NIT-TMP combination |
|---|---|---|
| MP026 | CAM, NIT, TMP | 0.28 |
| TB191 | CAM, NIT, TMP | 0.16 |

High pathogen diversity is observed in majority of bacterial infections and CombiANT™ can be applied with unpurified mixed samples. Omitting the strain purification step decreases the total assay time for determining which antibiotic combination is effective to use for treatment. It is anticipated that the CombiANT™ assay will be of great value for diagnostics and to formulate and validate personalized treatments. When CombiANT™ is applied to samples that can be differentiated by, for example, fluorescence or color, multiple FICis of different bacteria in the same sample can be obtained.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible.

REFERENCES

[1] Brochado, et al. Species-specific activity of antibacterial drug combinations. *Nature* 2018; 559: 259-263

[2] WO 2015/028983 A1

[3] Drieux, et al. Phenotypic detection of extended-spectrum beta-lactamase production in Enterobacteriaceae: review and bench guide. *Clin Microbiol Infect* 2008; 14 Suppl 1: 90-103

[4] US 2012/0149055 A1

[5] U.S. Pat. No. 4,778,758 A

[6] White, et al. Comparison of three different in vitro methods of detecting synergy: time-kill, checkerboard, and E test. *Antimicrob Agents Chemother* 1996; 40: 1914-1918

[7] U.S. Pat. No. 4,324,859 A

[8] Russ et al. Additivity of inhibitory effects in multidrug combinations. *Nat Microbiol.* 2018; 3: 1339-1345

[9] Bliss. The Toxicity of Poisons Applied Jointly. *Annals of Applied Biology.* 1939; 26: 585-615.

[10] Weinstock, et al. *Vibrio natriegens* as a fast-growing host for molecular biology. *Nat Methods.* 2016; 13: 849-851

The invention claimed is:

1. A method for determining agent interaction effects on a cell population, the method comprising:

adding a cell culture substrate into a culture container comprising N agent reservoirs at predefined positions relative to each other, wherein each agent reservoir of the N agent reservoirs comprises an agent, the N agent reservoirs enclose combination areas and N is an integer equal to or larger than three;

placing a cell population on and/or in the cell culture substrate and culturing the cell population on and/or in the cell culture substrate for a predefined period of time while the agents in the N agent reservoirs diffuse through the cell culture substrate and form at least partly overlapping agent concentration gradients in the cell culture substrate within the combination areas and substantially non-overlapping agent concentration gradients in the cell culture substrate peripheral to an outer boundary of the N agent reservoirs;

determining, for each agent reservoir of at least two adjacent agent reservoirs of the N agent reservoirs, an inhibition end point of an inhibition zone substantially lacking any growth of the cell population, the inhibition end point being positioned peripherally to the outer boundary of the agent reservoir;

determining, for the at least two adjacent agent reservoirs, a growth end point of a growth zone comprising growth of the cell population within a combination area with at least partly overlapping agent concentration gradients of the agents contained in the at least two adjacent agent reservoirs; and determining an agent interaction effect between the agents contained in the at least two adjacent agent reservoirs based on the inhibition end points and the growth end point.

2. The method according to claim 1, wherein adding the cell culture substrate comprises adding a cell culture substrate gel into the culture container and allowing the cell culture substrate gel to solidify into the cell culture substrate.

3. The method according to claim 1, further comprising:

determining, for each agent reservoir of the at least two adjacent agent reservoirs, a minimum inhibitor concentration (MIC) of the agent contained in the agent reservoir with regard to the cell population based on the inhibition end point; and determining, for each agent reservoir of the at least two adjacent agent reservoirs, a MIC of the agent contained in the agent reservoir in a mixture of the agents contained in the at least two adjacent agent reservoirs based on the growth end point, wherein determining the agent interaction effect comprises determining a fractional inhibitory concentration index (FICi) based on the MICs.

4. The method according to claim 3, wherein determining the MIC comprises determining, for each agent reservoir of the at least two adjacent agent reservoirs, the MIC of the agent contained in the agent reservoir based on a diffusion coefficient of the agent contained in the agent reservoir with regard to the cell culture substrate and the inhibition end point; and determining the MIC in the mixture comprises determining, for each agent reservoir of the at least two adjacent agent reservoirs, the MIC of the agent contained in the agent reservoir in the mixture of the agents contained in the at least two adjacent agent reservoirs based on the diffusion coefficient and the growth end point.

5. The method according to claim 4, further comprising determining the diffusion coefficient of an agent by:

adding the cell culture substrate gel into the culture container comprising the N agent reservoirs comprising the agent at respective, different concentrations and allowing the cell culture substrate gel to solidify into the cell culture substrate;

placing a test cell population on and/or in the cell culture substrate and culturing the test cell population on and/or in the cell culture substrate for the predefined period of time while the agent in the N agent reservoirs diffuse through the cell culture substrate, wherein the test cell population has a known MIC of the agent;

determining, for at least one agent reservoir of the N agent reservoirs, an inhibition end point of an inhibition zone substantially lacking any growth of the test cell population, the inhibition end point being positioned peripherally to the outer boundary of the agent reservoir; and determining the diffusion coefficient of the agent with regard to the cell culture substrate based on the inhibition end point and the MIC of the agent with regard to the test cell population.

6. The method according to claim 1, further comprising adding, into each agent reservoir of the N agent reservoirs, the agent mixed with a gel and allowing the gel to solidify into an agent comprising plug.

7. The method according to claim 1, wherein each agent reservoir of the N agent reservoirs comprises an agent in lyophilized or dried form; and the method further comprising adding, into each agent reservoir of the N agent reservoirs, a gel, into which the agent is dissolved or dispersed, and allowing the gel to solidify into an agent comprising plug.

8. The method according to claim 1, wherein the N agent reservoirs are arranged at predefined positions relative to each other along a circumference of a circle; and the inhibition end point is positioned along an axis passing through the center of the circle and the agent reservoir and at a position along the axis peripheral to the outer boundary of the agent reservoir.

9. The method according to claim 8, wherein

N is three;

each agent reservoir is enclosed between a circumferential wall aligned with the circumference of the circle and by a chord wall; and the three chord walls enclose a triangle.

10. The method according to claim 9, wherein the three chord walls enclose an equilateral triangle.

11. The method according to claim 1, wherein Nis three.

12. The method according to claim 1, wherein the cell population is a bacterial population from a body sample from a subject suffering from a bacterial infection; and each agent reservoir of the N agent reservoirs comprises an antimicrobial agent, the method further comprising:

identifying a combination of antimicrobial agents that are effective in inhibiting growth of the bacterial population; and administering the identified combination of antimicrobial agents to the subject in order to combat the bacterial infection.

* * * * *